United States Patent
O'Halloran et al.

(10) Patent No.: US 10,285,741 B2
(45) Date of Patent: *May 14, 2019

(54) METHODS AND APPARATUS FOR TREATING VERTEBRAL FRACTURES

(71) Applicant: GLOBUS MEDICAL, INC., Audubon, PA (US)

(72) Inventors: Damien O'Halloran, Conshohocken, PA (US); Sean Suh, Morganville, NJ (US)

(73) Assignee: Globus Medical, Inc., Audubon, PA (US)

( * ) Notice: Subject to any disclaimer, the term of this patent is extended or adjusted under 35 U.S.C. 154(b) by 385 days.

This patent is subject to a terminal disclaimer.

(21) Appl. No.: 15/146,973

(22) Filed: May 5, 2016

(65) Prior Publication Data
US 2016/0242828 A1 Aug. 25, 2016

Related U.S. Application Data

(60) Continuation of application No. 13/668,512, filed on Nov. 5, 2012, now Pat. No. 9,358,058, and a continuation-in-part of application No. 15/084,546, filed on Mar. 30, 2016, which is a division of application No. 13/184,170, filed on Jul. 15, 2011, now Pat. No. 9,326,799, which is a continuation-in-part of application No. 12/823,622, filed on Jun. 25, 2010, now Pat. No. 9,295,509, which is a continuation-in-part of application No. 12/632,325, filed on Dec. 7, 2009, now Pat. No. 8,734,458.

(60) Provisional application No. 61/383,243, filed on Sep. 15, 2010, provisional application No. 61/383,235, filed on Sep. 15, 2010.

(51) Int. Cl.
 A61B 17/70 (2006.01)
 A61B 17/88 (2006.01)
 A61B 17/16 (2006.01)

(52) U.S. Cl.
 CPC ...... *A61B 17/7097* (2013.01); *A61B 17/1617* (2013.01); *A61B 17/8805* (2013.01); *A61B 17/1642* (2013.01)

(58) Field of Classification Search
 CPC .............. A61B 17/1671; A61B 17/7097
 See application file for complete search history.

(56) References Cited

U.S. PATENT DOCUMENTS

| | | |
|---|---|---|
| 4,969,888 A | 11/1990 | Scholten |
| 5,445,639 A | 8/1995 | Kuslich |
| 5,549,679 A | 8/1996 | Kuslich |

(Continued)

FOREIGN PATENT DOCUMENTS

WO 9902214 A1 1/1999

*Primary Examiner* — Zade Coley

(57) ABSTRACT

Methods and apparatus for treating bones, including, in one or more embodiments, methods and apparatus for treatment of vertebral fractures that include a containment assembly for cement containment and/or a balloon assembly for maintaining vertebral height. A containment assembly comprising a containment jacket adapted to be deployed inside bone; and a dividing wall that separates the interior of the containment jacket into a proximal region and a distal region, the dividing wall having an opening for providing access to the distal region from the proximal region.

20 Claims, 54 Drawing Sheets

(56) References Cited

U.S. PATENT DOCUMENTS

| | | | |
|---|---|---|---|
| 6,063,112 A * | 5/2000 | Sgro | A61F 2/07 623/1.12 |
| 6,248,110 B1 * | 6/2001 | Reiley | A61B 10/025 606/192 |
| 6,440,138 B1 | 8/2002 | Reiley | |
| 7,175,628 B2 * | 2/2007 | Lin | A61D 7/00 604/500 |
| 7,226,481 B2 | 6/2007 | Kuslich | |
| 7,909,827 B2 | 3/2011 | Reiley | |
| 2002/0082600 A1 * | 6/2002 | Shaolian | A61B 17/1671 606/262 |
| 2002/0156482 A1 * | 10/2002 | Scribner | A61B 17/7097 606/92 |
| 2002/0161373 A1 * | 10/2002 | Osorio | A61B 17/1604 606/86 R |
| 2002/0183758 A1 * | 12/2002 | Middleton | A61B 17/1617 606/79 |
| 2002/0198526 A1 * | 12/2002 | Shaolian | A61B 17/1671 606/254 |
| 2003/0050644 A1 | 3/2003 | Beucher | |
| 2003/0088249 A1 * | 5/2003 | Furderer | A61B 17/7097 623/17.12 |
| 2003/0130664 A1 * | 7/2003 | Boucher | A61B 17/1631 606/86 R |
| 2004/0098015 A1 * | 5/2004 | Weikel | A61B 17/025 606/192 |
| 2004/0230309 A1 | 11/2004 | Dimauro | |
| 2006/0100706 A1 * | 5/2006 | Shadduck | A61B 17/1617 623/17.11 |
| 2006/0155296 A1 * | 7/2006 | Richter | A61B 17/7097 606/94 |
| 2007/0055201 A1 * | 3/2007 | Seto | A61B 17/1617 604/96.01 |
| 2007/0055276 A1 * | 3/2007 | Edidin | A61B 17/8855 606/92 |
| 2007/0225705 A1 | 9/2007 | Osorio | |
| 2007/0276491 A1 * | 11/2007 | Ahrens | A61F 2/441 623/17.11 |
| 2008/0046082 A1 | 2/2008 | Lee | |
| 2008/0249604 A1 * | 10/2008 | Donovan | A61B 17/8811 606/249 |
| 2008/0269754 A1 * | 10/2008 | Lutz | A61B 17/1624 606/79 |
| 2009/0187249 A1 | 7/2009 | Osman | |
| 2009/0299374 A1 * | 12/2009 | Tilson | A61B 17/8816 606/94 |
| 2009/0299401 A1 | 12/2009 | Tilson | |
| 2009/0312807 A1 * | 12/2009 | Boudreault | A61B 17/025 606/86 R |
| 2010/0262240 A1 * | 10/2010 | Chavatte | A61B 17/7098 623/17.11 |
| 2011/0137317 A1 | 6/2011 | O'Halloran et al. | |
| 2011/0202064 A1 * | 8/2011 | O'Halloran | A61B 17/1671 606/94 |

* cited by examiner

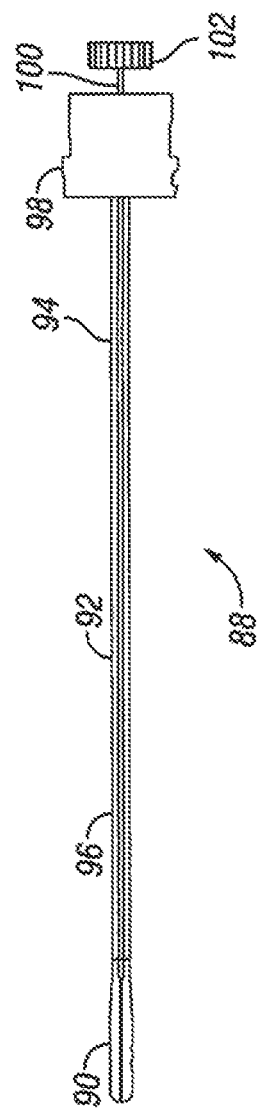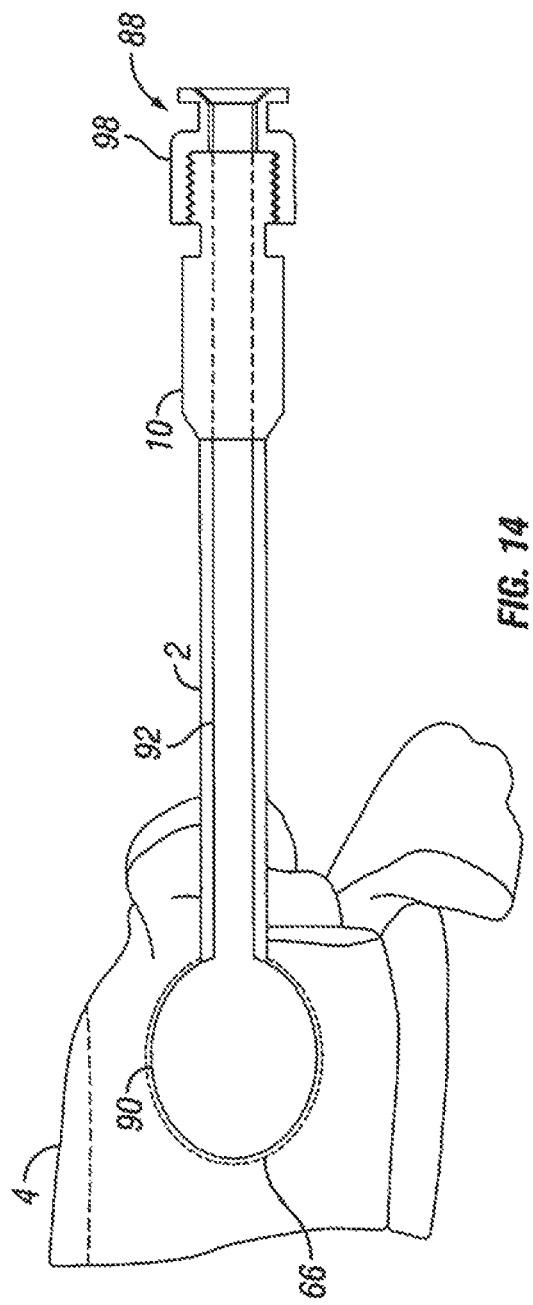

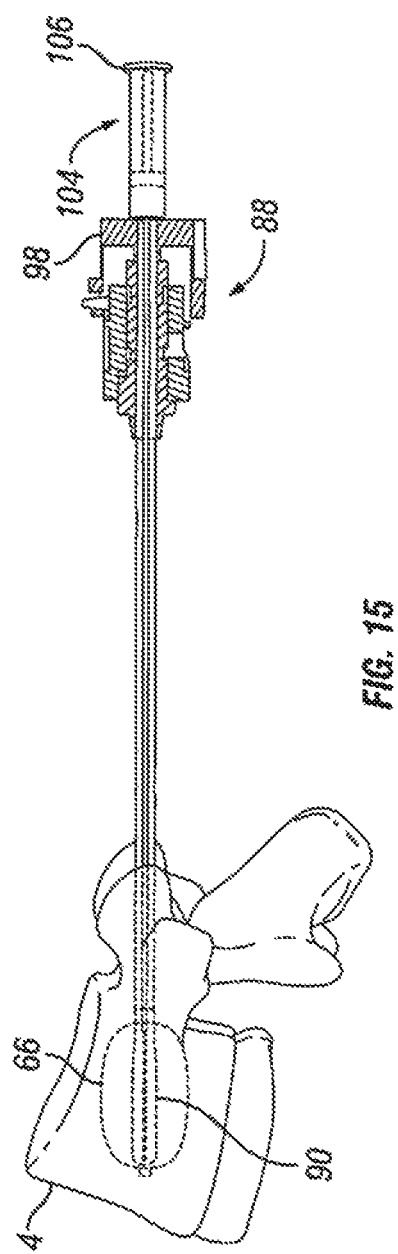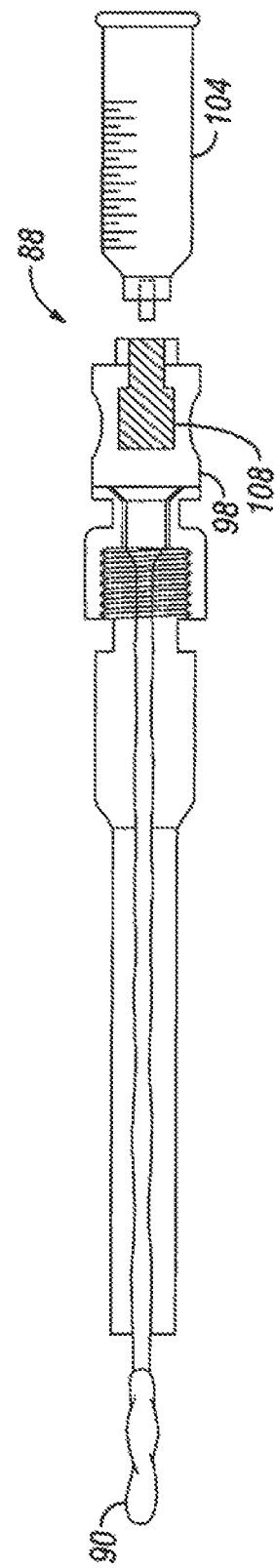

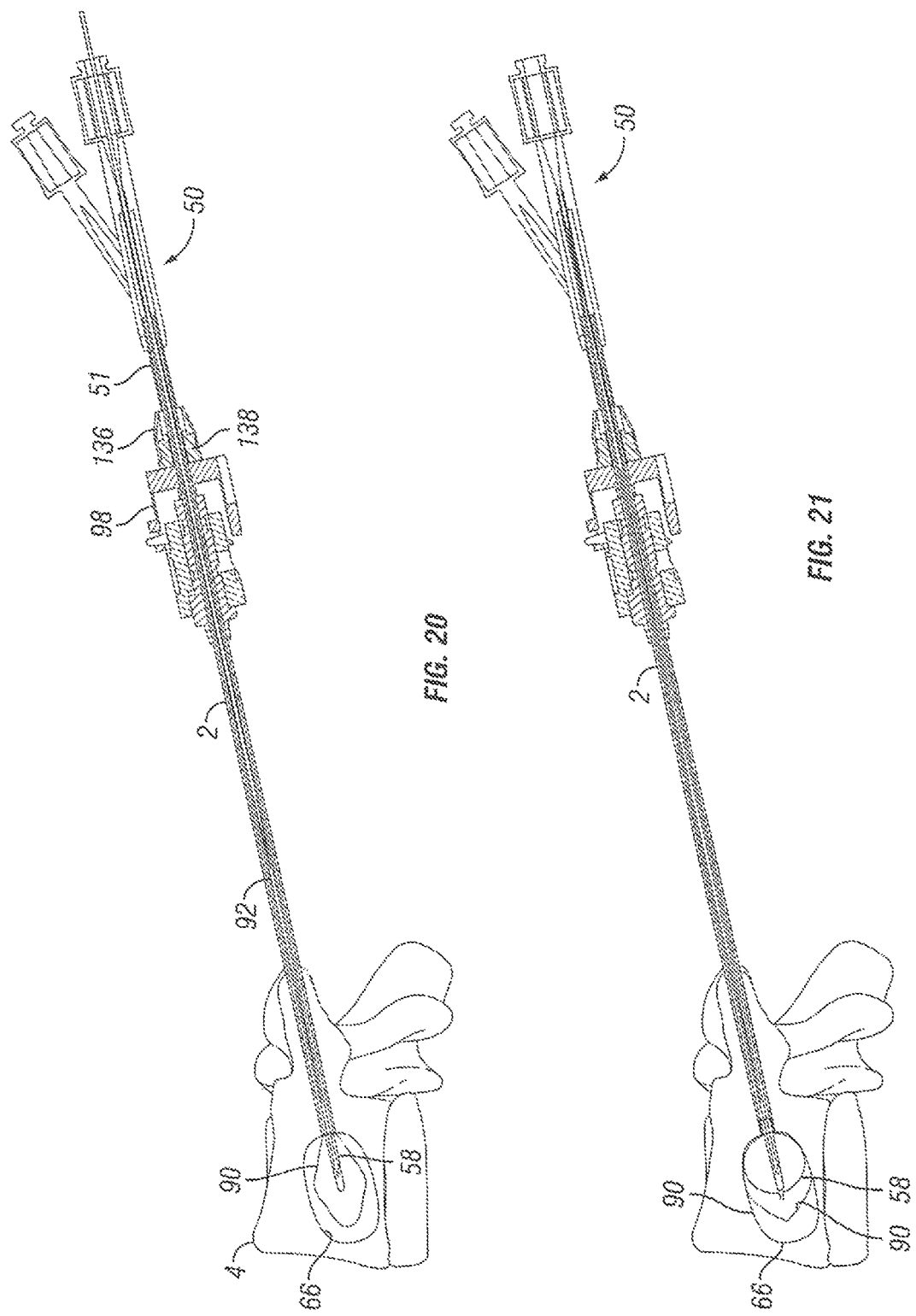

METHODS AND APPARATUS FOR TREATING VERTEBRAL FRACTURES

CROSS-REFERENCE TO RELATED APPLICATIONS

The present application is a continuation of U.S. application Ser. No. 13/668,512, filed Nov. 5, 2012. The present application is also a continuation-in-part of U.S. application Ser. No. 15/084,546, filed Mar. 30, 2016, which is a divisional of U.S. application Ser. No. 13/184,170, filed Jul. 15, 2011, now U.S. Pat. No. 9,326,799, which is a continuation-in-part of U.S. application Ser. No. 12/823,622, filed on Jun. 25, 2010, now U.S. Pat. No. 9,295,509, which is a continuation of U.S. application Ser. No. 12/632,325, filed on Dec. 7, 2009, now U.S. Pat. No. 8,734,458. U.S. application Ser. No. 13/184,170 also claims priority to Provisional Application No. 61/383,243, filed on Sep. 15, 2010, and No. 61/383,235, filed on Sep. 15, 2010. The disclosures of all of which are incorporated by reference herein in their entireties for all purposes.

FIELD OF THE INVENTION

The present disclosure generally relates to treatment of bones. In particular, in one or more embodiments, the present disclosure relates to methods and apparatus for treatment of vertebral fractures that include a containment assembly for cement containment and/or a balloon assembly for maintaining vertebral height.

BACKGROUND

Bones and bony structures are susceptible to a variety of weaknesses that can affect their ability to provide support and structure, Weaknesses in bony structures may have many causes, including degenerative diseases, tumors, fractures, and dislocations. By way of example, weaknesses in vertebrae can lead to compression fractures that involve the collapse of one or more vertebrae in the spine. These vertebral compression fractures may be caused by a number of conditions including osteoporosis, trauma, and tumors. Advances in medicine and engineering have provided doctors with a plurality of devices and techniques for alleviating or curing these weaknesses.

One technique for treating vertebral fractures is vertebroplasty. In vertebroplasty, a physician may use a needle to inject bone cement into a fractured vertebral body to stabilize the fracture. Kyphoplasty is another technique for treating vertebra fractures that involves insertion of a balloon into the fractured vertebra to restore the height of the vertebra. The balloon may then be removed followed by injection of bone cement into the vertebral body to stabilize the fracture. Leakage of the bone cement in both vertebroplasty and kyphoplasty is a common problem that can lead to complications. Another problem associated with these techniques is the potential for inadequate height restoration to the fractured vertebral body.

Thus, there is a need for methods and apparatus that can provide stabilization to a fractured vertebra.

SUMMARY

The present disclosure generally relates to treatment of bones. In particular, in one or more embodiments, the present disclosure relates to methods and apparatus for treatment of vertebral fractures that include a containment assembly for cement containment and/or a balloon assembly for maintaining vertebral height.

An embodiment of the present invention provides a containment assembly for treating bone, the containment assembly comprising: a containment jacket adapted to be deployed inside bone; and a dividing wall that separates the interior of the containment jacket into a proximal region and a distal region, the dividing wall having an opening for providing access to the distal region from the proximal region.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of the present invention and should not be used to limit or define the invention.

FIG. 13 illustrates a containment assembly with a containment jacket in a wrapped/deflated state in accordance with one embodiment of the present invention.

FIG. 14 illustrates a containment jacket disposed in a vertebral body in accordance with one embodiment of the present invention.

FIGS. 15-16 illustrate removal of fluid from a containment jacket placed in a vertebral body in accordance with embodiments of the present invention.

FIG. 20 illustrates insertion of a balloon into a containment jacket placed in a vertebral body in accordance with one embodiment of the present invention.

FIG. 21 illustrates inflation of a balloon in a containment jacket placed within a vertebral body in accordance with one embodiment of the present invention.

DETAILED DESCRIPTION OF THE ILLUSTRATED EMBODIMENTS

Creation of Access Channel into a Vertebral Body

Figure 1:
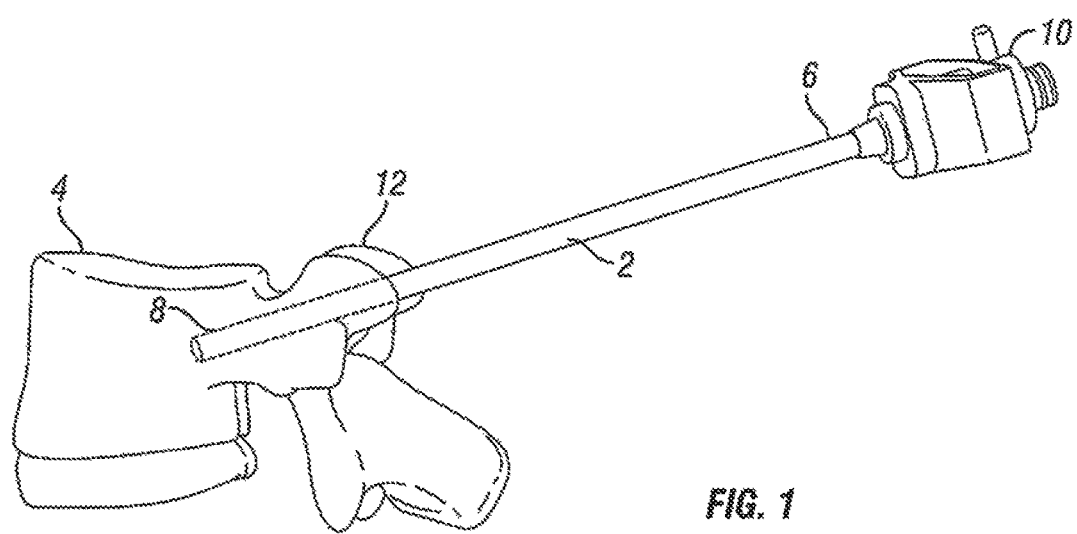
FIG. 1 illustrates a cannula inserted into a vertebral body in accordance with one embodiment of the present invention.

Embodiments of the present technique for treating vertebral fractures may include creating an access channel into a vertebral body. In some embodiments, creating the access channel may include placement of a cannula into the vertebral body. FIG. 1 illustrates a cannula 2 that has been inserted into a vertebral body 4 to provide access to the vertebral body 4 in accordance with one embodiment of the present invention. As will be appreciated, the cannula 2 can be configured to allow passage of various instruments and materials into the vertebral body 4 in accordance with present embodiments. As illustrated, the cannula 2 may have a proximal end 6 and a distal end 8 extending into the vertebral body 4. In the illustrated embodiment, a cannula hub 10 is disposed on the proximal end 6 of the cannula 2. In an embodiment, the cannula 2 may be inserted into the vertebral body 4 through a pedicle 12. In an embodiment (not illustrated), the cannula assembly 2 is not inserted through the pedicle 12. While not illustrated, in an embodiment, the cannula 2 may be a trocar-tipped cannula. By way of example, the cannula 2 may be a diamond, scoop, bevel, trocar tipped cannula.

Figure 2:
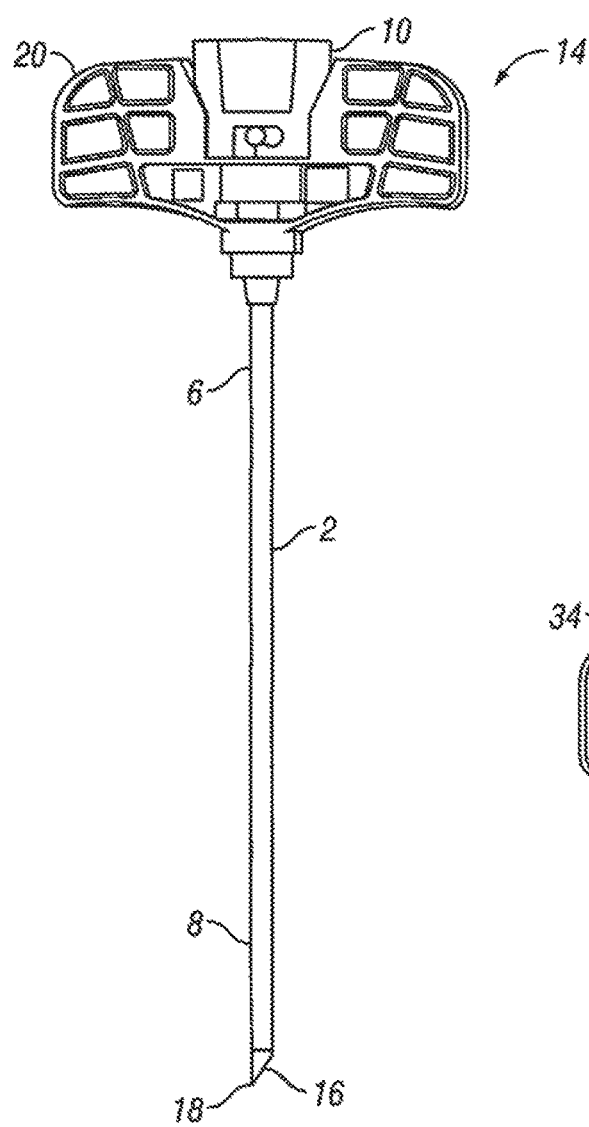
FIG. 2 illustrates a cannula assembly having a tapered cannula in accordance with one embodiment of the present invention.

FIG. 2 illustrates a cannula assembly 14 that may be used for introduction of the cannula 2 into the vertebral body 4 (e.g., FIG. 1), in accordance with one embodiment. As illustrated, the cannula assembly 14 includes cannula 2 having a cannula hub 10 disposed on the proximal end 6. In the illustrated embodiment, the cannula assembly 14 further may include a stylet 16 removably disposed in the cannula 2. As illustrated, the stylet 16 may have a pointed end 18 that extends beyond the distal end 8 of the cannula 2. In an embodiment, the cannula assembly 14 may further comprise a handle 20 disposed at the proximal end 6 of the cannula 2.

With reference now to FIGS. 1 and 2, to place the cannula 2 into the vertebral body 4, the physician may make an incision in the patient's back (not illustrated), for example. The distal end 8 of the cannula 2 may be inserted into the incision. The physician may then apply longitudinal force to the cannula assembly 14 while rotating the handle 20 to advance the cannula 2 through the patient's tissue and into the vertebral body 4. In other embodiments, the handle 20 may use other mechanisms to advance the cannula 2 through the patient's tissue, such as a ratcheting system. Once the cannula 2 has been inserted into the vertebral body 4, the stylet 16 and handle 20 may be removed, leaving the cannula 2 in the vertebral body 4, as shown in FIG. 2. In this manner, the cannula 2 may be inserted into the vertebral body 4, thus creating an access channel to the vertebral body 4.

While the cannula assembly 14 may be suited for creation of an access channel in all regions of the vertebral column, the cannula assembly 14 may be particularly suited for access in the middle of the thoracic region and lower. If access is desired from the middle of the thoracic region and above, a device having a tapered cannula (not illustrated) may be used, in accordance with one embodiment. While the tapered cannula, it should be understood that the tapered cannula may also be used to create an access channel to vertebral bodies in all regions of the vertebral column.

Figure 3:
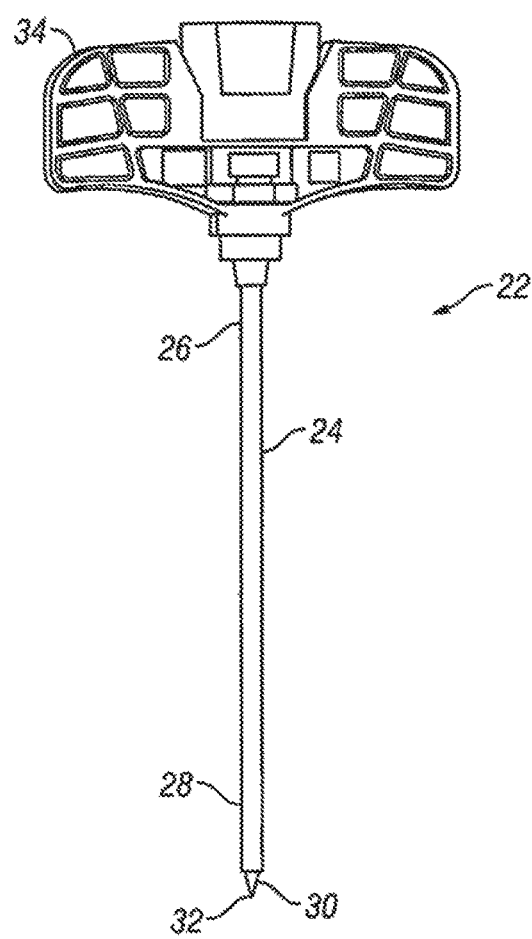
FIG. 3 illustrates a needle assembly in accordance with one embodiment of the present invention.
Figure 4:
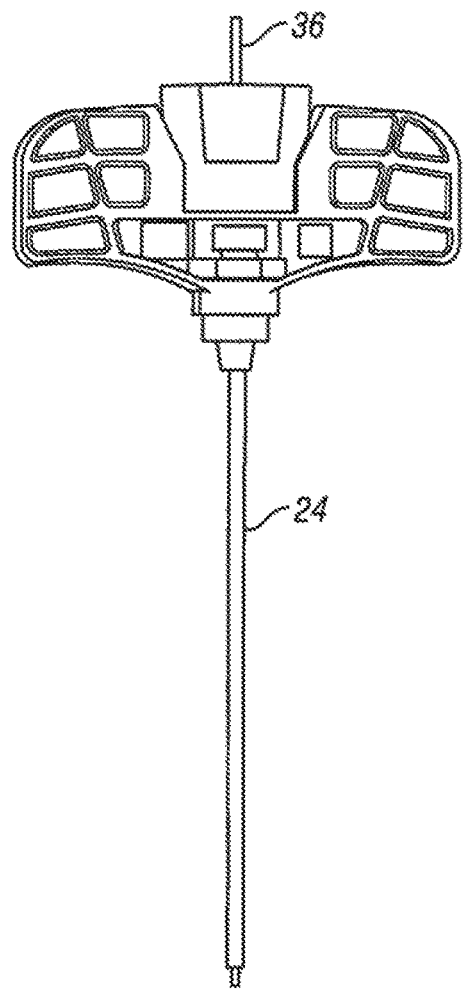
FIG. 4 illustrates a needle assembly having a guide wire disposed therethrough in accordance with one embodiment of the present invention.
Figure 5:
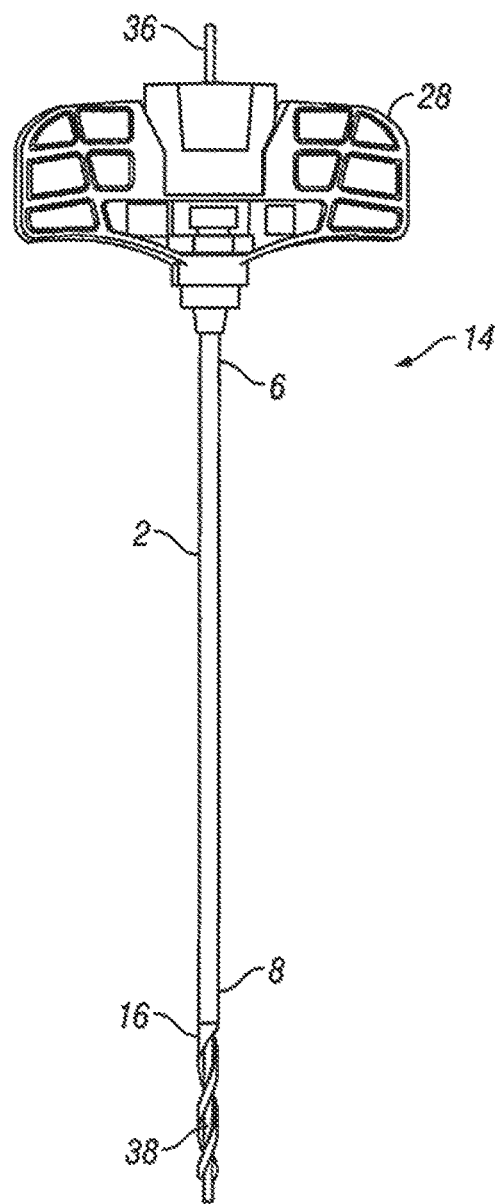
FIG. 5 illustrates a cannula assembly disposed over a guide wire and having a drill-tip stylet in accordance with one embodiment of the present invention.

While FIG. 1-2 describe use of a cannula assembly 14 having a cannula 2 with a stylet 16 that is sharp and pointed disposed in the cannula 2 for creation of the access channel into the vertebral body 4, it should be understood that a variety of different devices and techniques may be used for creation of the access channel into the vertebral body 4 in accordance with embodiment of the present invention. Referring now to FIGS. 3-5, an alternative technique for creating an access channel into the vertebral body 4 (e.g., FIG. 1) is illustrated in accordance with one embodiment of the present invention.

FIG. 3 illustrates a needle assembly 22 that may be used in creation of an access channel through a patient's tissue to a vertebral body 4 (e.g., FIG. 1) in accordance with an embodiment of the present invention. In the illustrated embodiment, the needle assembly 22 comprises a needle 24 having a proximal end 26 and a distal end 28. The needle assembly 22 further may include a stylet 30 removably disposed in the needle 24. As illustrated, the stylet 30 may have a pointed end 32 that extends beyond the distal end 28 of the needle 24. As illustrated, the needle assembly 22 may further comprise a handle 34 disposed on the proximal end 26 of the needle 22. In an embodiment, the needle assembly 22 include a Jamshidi needle, such as a diamond, bevel-tipped Jamshidi needle.

The needle assembly 22 of FIG. 3 may be inserted into the vertebral body 4 (e.g., FIG. 1) in a similar manner to the cannula assembly 14 of FIG. 2. By way of example, the distal end 28 of the needle 24 may be inserted into an incision in the patient's back (not illustrated). To advance the needle 24 into the vertebral body 4, longitudinal force may then be applied to the needle assembly 24 while rotating the handle 34. The stylet 30 and handle 34 may then be removed, leaving the needle 24. As illustrated by FIG. 4, a guide wire 36 (e.g., a k-wire) may be disposed through the needle 24 and into the vertebral body 4. With the guide wire 36 in place, the needle 24 may be removed.

As illustrated by FIG. 5, after removal of the needle 24, a cannula 14 may be inserted over the guide wire 36 and into the vertebral body 4 (e.g., FIG. 1). In the illustrated embodiment, the cannula assembly 14 includes a cannula 2 having a handle 20 disposed on the proximal end 6. In an embodiment, a stylet 16 having a drill-shaped end 38 may be disposed in the cannula 2. As illustrated, the drill-shaped end 38 of the stylet 16 may extend out from the distal end 8 of the cannula 2. While not illustrated, the stylet 16 may have a conically shaped end in an alternative embodiment. To advance the cannula assembly 14 over the guide wire 36 and through the patient's tissue (not illustrated), the physician may apply longitudinal force to the cannula assembly 14 while rotating the handle 20. Once the cannula 2 has been inserted into the vertebral body 4, the stylet 16, handle 20, and guide wire 36 may be removed, leaving the cannula 2 in the vertebral body 4.

Embodiments of the present technique may include a gripping feature (not illustrated) at the distal end 8 of the cannula 2 that can, for example, thread into bone (e.g., pedicle 12) during insertion there through. In this manner, movement and/or slippage of the cannula 2 can be reduced or even prevented. Non-limiting examples of gripping features that can be used include knurling or threading. In alternative embodiments, the gripping feature may be created by grit blasting or laser ablating a portion of the distal end 8 of the cannula 2.

While not illustrated, embodiments of the present technique may also include flaring or tapering at the distal end 8 of the cannula 2. The flaring/tapering may, for example, facilitate withdrawal of balloon(s) from the cannula 2. For example, folding of a balloon 58 (e.g., FIG. 7) during withdrawal may be improved with the flaring/tapering at the distal end 8.

Figure 6:
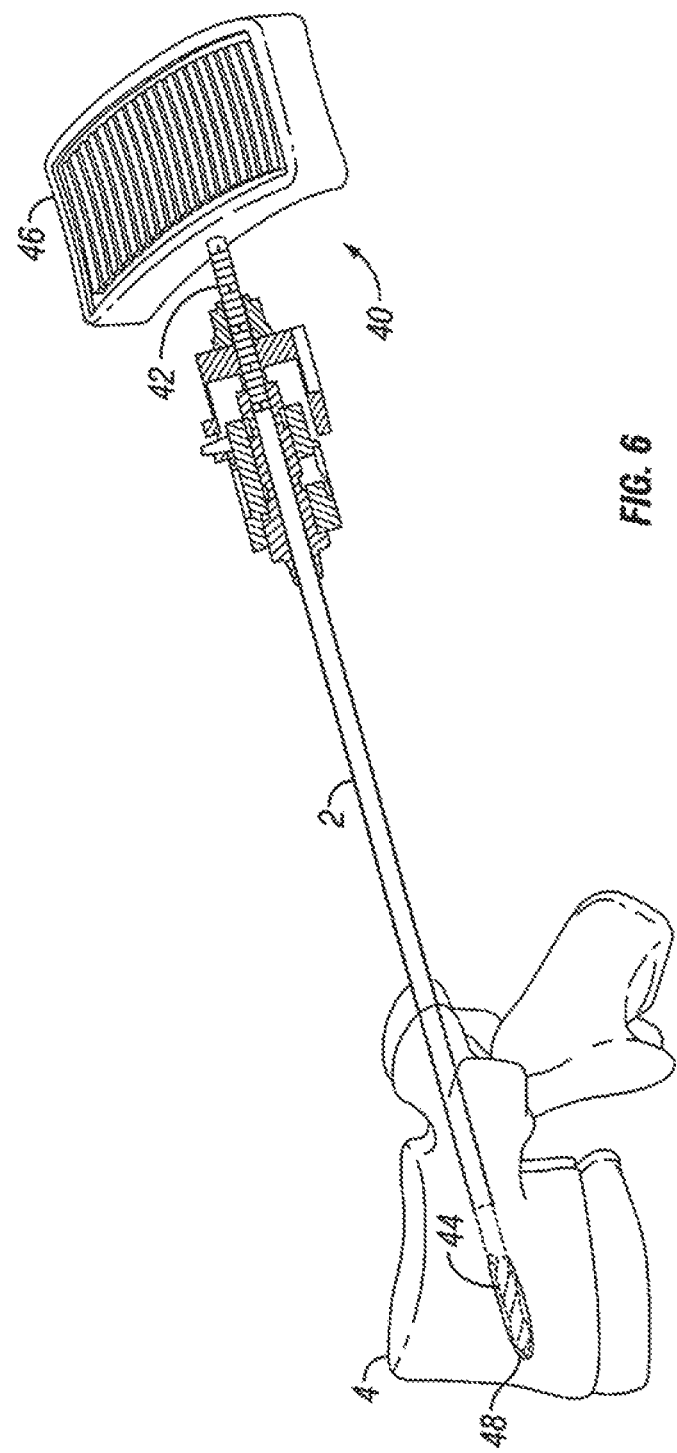
FIG. 6 illustrates insertion of a drill through the cannula assembly to create a channel in a vertebral body in accordance with one embodiment of the present invention.

Referring now to FIG. 6, creating an access channel into the vertebral body 4 may further include using drill 40 to advance further into the vertebral body 4. In the illustrated embodiment, the drill 40 comprises a shaft 42 having a bit 44 disposed at one end thereof. A handle 46 may be disposed on the other end of the shaft 42. As illustrated by FIG. 6, the drill 40 may be used to create a channel 48 in the vertebral body 4. By way of example, the physician may insert the drill 40 through the cannula 2 until the bit 44 contacts bone (e.g., cancellous bone) within the vertebral body 4. The channel 48 in the vertebral body 4 may then be created by application of longitudinal forces to the drill 40 while rotating the handle 46. The drill 40 may then be removed from the cannula 2 with the cannula 2 remaining in place providing access to the channel 48 within the vertebral body 4.

Creation of a Cavity in the Vertebral Body

Figure 7:
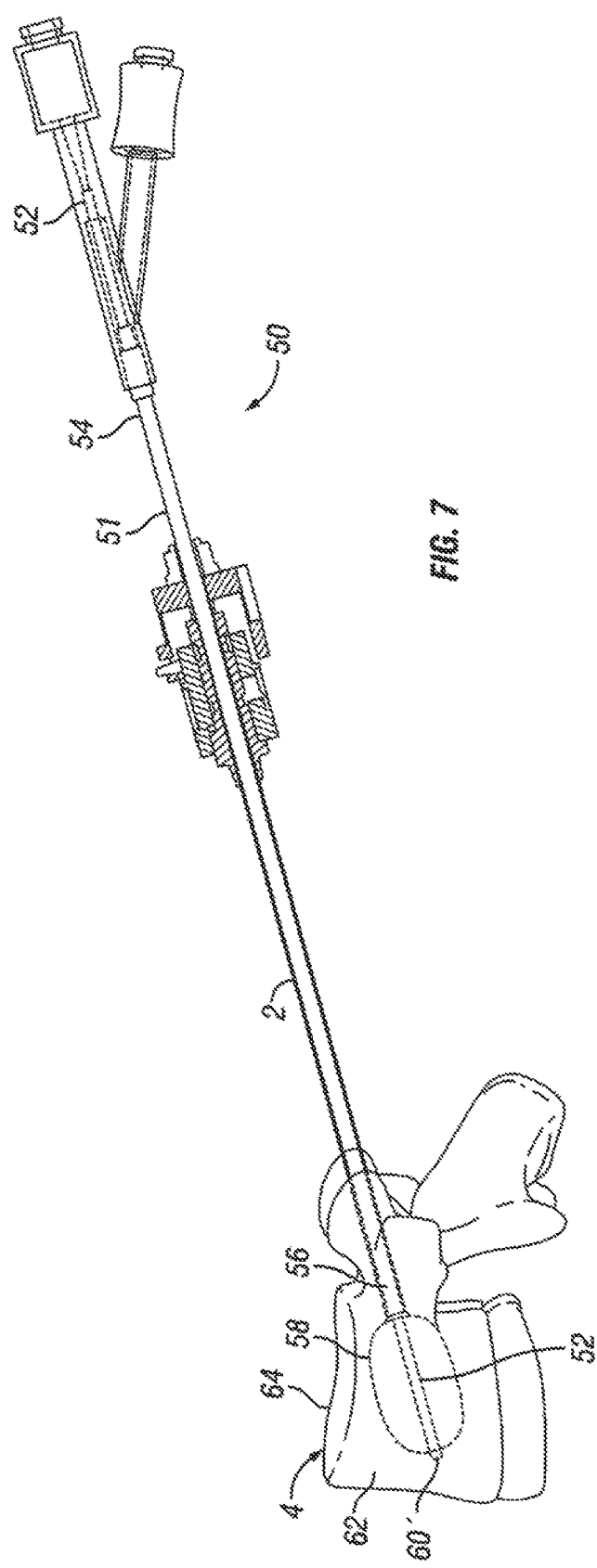
FIG. 7 illustrates insertion of a balloon into a vertebral body for cavity creation in accordance with one embodiment of the present invention.
Figure 8:
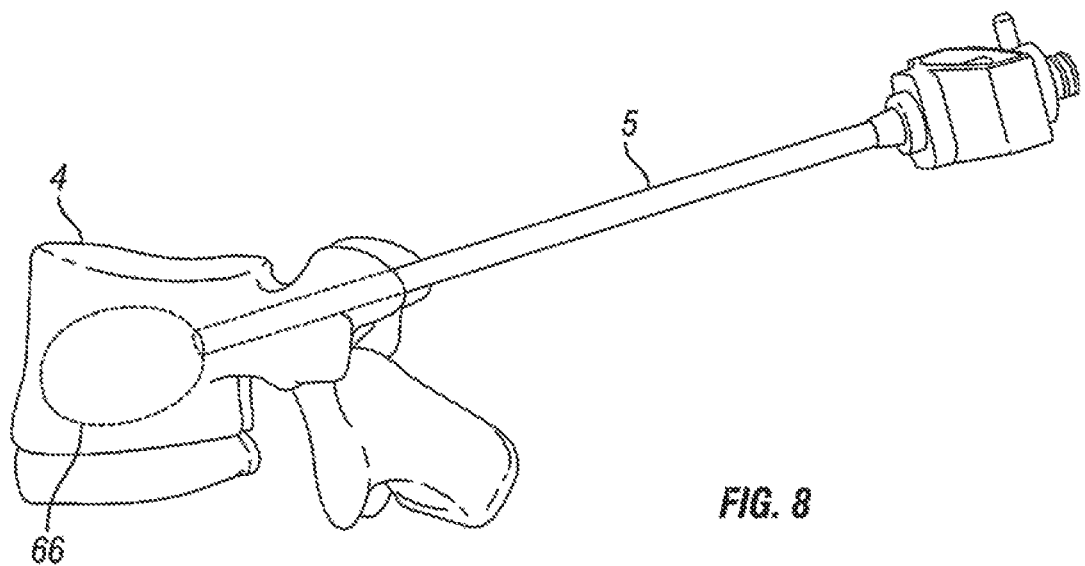
FIG. 8 illustrates a cavity that has been created in a vertebral body in accordance with one embodiment of the present invention.

Embodiments of the present technique for treating vertebral fractures may further include creating a cavity in the vertebral body 4. Any of a variety of different techniques may be used for creation of the cavity in the vertebral body 4. FIGS. 7 and 8 illustrate creation of a cavity 66 in vertebral body 4 with a balloon assembly 50 in accordance with one embodiment of the present invention. As illustrated, cannula 2 has been inserted into the vertebral body 4 with the cannula 2 providing access into the vertebral body 4. With reference now to FIG. 7, to create the cavity, balloon assembly 50 may be inserted into the previously created channel 48 (e.g., FIG. 6) in the vertebral body 4 through the cannula 2. In certain embodiments, the balloon assembly 50 may be an inflatable bone tamp. In the illustrated embodiment, the balloon assembly 50 includes a catheter 51. As illustrated, an inner lumen 52 may be disposed within the catheter. The catheter 51 may have a proximal end 54 and a distal end 56. A balloon 58 may be attached to the distal end 56 of the catheter 51. While FIG. 7 illustrates the balloon 58 in an expanded configuration, it should be understood that the balloon 58 should be inserted into the vertebral body 4 in a deflated state. The balloon 58 used to create the cavity may include any of a variety of different balloons suitable for use in medical procedures. Examples of suitable balloons include those commonly used in kyphoplasty, including those comprising plastics, composite materials, polyethylene, rubber, polyurethane, or any other suitable material. As illustrated, the inner lumen 52 may have an exit port 60 at its distal end 56, for example, that extends beyond the balloon 58.

As illustrated by FIG. 7, the balloon 58 may be inflated, for example, to compact the cancellous bone 62 in the interior portion of the vertebral body 4 enlarging the channel 48 (e.g., FIG. 6) to create a cavity 66 (e.g., FIG. 8) within the vertebral body 4. In addition to creation of the cavity 66, the balloon 58 may also, for example, force apart the compact bone 64, restoring height to the vertebral body 4. After cavity creation, the balloon 58 may be deflated and removed from the vertebral body 4. As best seen in FIG. 8, cavity 66 should remain in vertebral body 4 after removal of the balloon 58.

Figure 9:
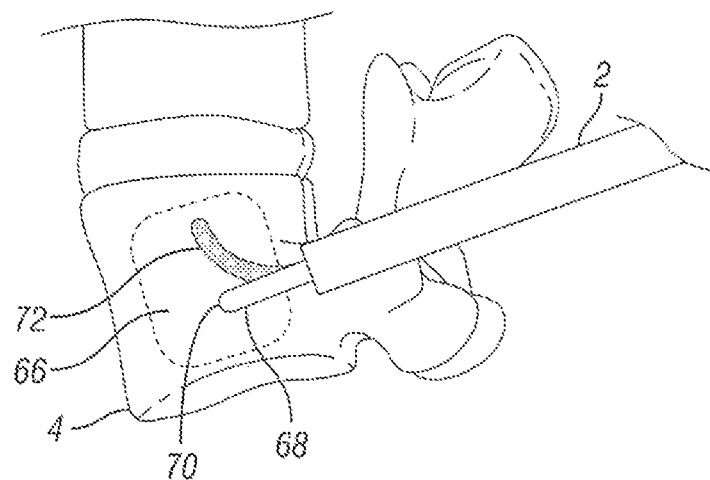
FIG. 9 illustrates creation of a cavity using a mechanical device in accordance with one embodiment of the present invention.

While FIGS. 7-8 illustrate the use of the balloon assembly 50 for creation of the cavity 66 in the vertebral body 4, those of ordinary skill in the art will appreciate that other suitable techniques may also be used for creation of the cavity 66. By way of example, an expandable jack or other suitable mechanical device may be used to create the cavity in the vertebral body 4. FIG. 9 illustrates use of a mechanical device 68 for creation of cavity 66 in the vertebral body 4 in accordance with one embodiment of the present invention. In the illustrated embodiment, the mechanical device 68 includes an outer sleeve 70 that has been inserted into the cannula 2 with one end of the outer sleeve 70 extending beyond the cannula 2 and into the vertebral body 4. As illustrated, the mechanical device 68 further includes a curved tip 72 that extends from the outer sleeve 70. In one embodiment, the curved tip 72 can have sharp edges, for example, for cutting through cancellous bone. The curved tip 72 may be manipulated within the vertebral body 4 to create the cavity 66. While not illustrated, the mechanical device 68 has an initial position for insertion through the cannula 2. In the initial position, the curved tip 72 is in a retracted state so that it is disposed within the outer sleeve 70 or does not extend too far beyond the outer sleeve 70. At a desired time, the curved tip 72 can then be extended from the outer sleeve 70.

Figure 10:
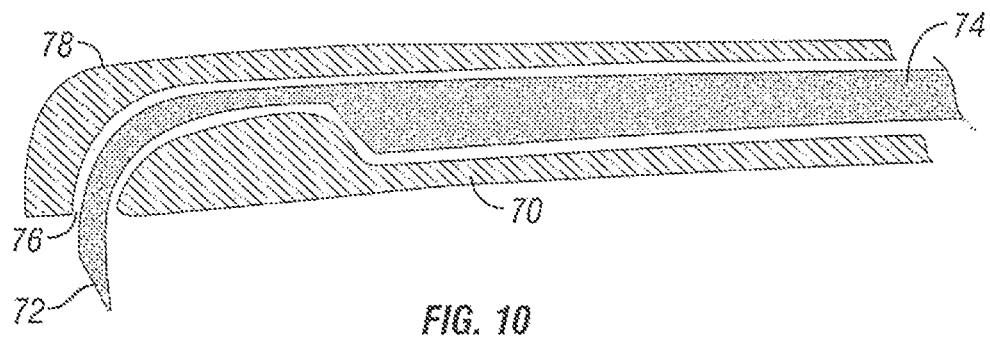
FIG. 10 illustrates a mechanical device that can be used to create a cavity in a vertebral body in accordance with one embodiment of the present invention.

FIG. 10 illustrates one embodiment of a mechanical device 68 that may be used to create the cavity 66 (e.g., FIG. 9) in accordance with one embodiment of the present invention. In the illustrated embodiment, the mechanical device 68 includes an outer sleeve 70 having an inner shaft 74 disposed therein. As illustrated, the inner shaft 74 may have a curved tip 72 at its distal end. In one embodiment, the curved tip 72 comprises nitinol or other suitable memory alloy. In some embodiments, the curved tip 72 can be extended to extend through an opening 76 at the distal end 78 of the outer sleeve 70.

Figure 11:
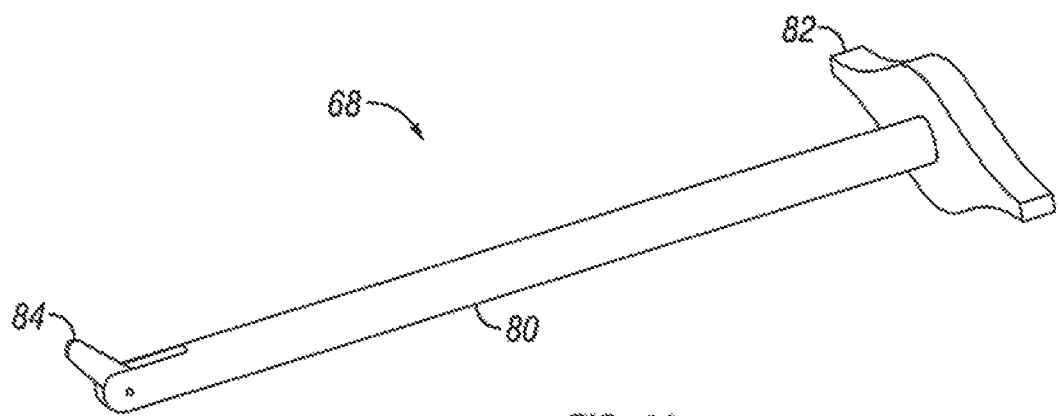
FIG. 11 illustrates a mechanical device having a single-arm cutting mechanism that can be used to create a cavity in a vertebral body in accordance with one embodiment of the present invention.
Figure 12:
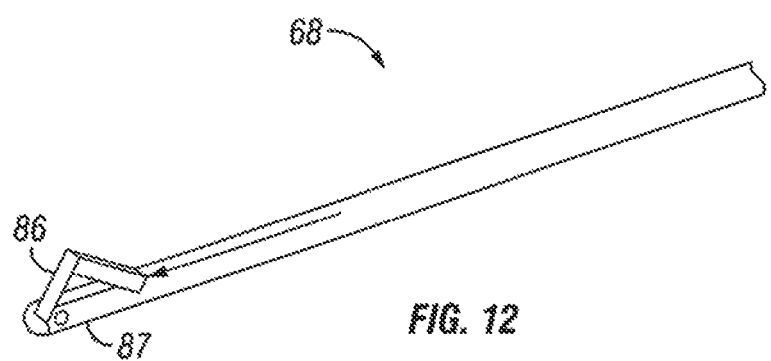
FIG. 12 illustrates a mechanical device having a double-arm cutting mechanism that can be used to create a cavity in a vertebral body in accordance with one embodiment of the present invention.

FIG. 11 illustrates another embodiment of a mechanical device 68 that may be used to create the cavity 66 (e.g., FIG. 9) in accordance with one embodiment of the present invention. In the illustrated embodiment, the mechanical device 68 includes a shaft 80 having a handle assembly 82 at one end and a single-arm cutting mechanism 84 at its other end. Alternatively, as illustrated by FIG. 12, the mechanical device 68 may include a double-arm cutting mechanism 86 at its distal end 87.

Accordingly, embodiments of the present invention may include creation of cavity 66 in the vertebral body 4, as illustrate by FIG. 7. As previously discussed, the cavity 66 may be formed using any of a variety of different technique, including, for example, using an inflatable balloon, a mechanical device, or a combination of both. As illustrated, the cannula 2 should extend into the cavity 66, providing access to the cavity 66. While not illustrated, embodiments of the present invention further may include coating the wall of the cavity 66 with a bone growing agent.

Treatment of Vertebral Body

In accordance with embodiments of the present invention, a filler material may be introduced into the cavity 66, for example, to stabilize a fracture in the vertebral body 4. However, prior to insertion of the filler material, embodiments of the present technique further may include inserting a containment enclosure (e.g., jacket, housing, covering, container, vessel, receptacle, sleeve, etc.) into the cavity 66 in the vertebral body 4. The containment enclosure or jacket may be employed to contain the filler material (e.g., cement) introduced into the cavity 66, for example, to prevent undesirable leakage. In this manner, problems associated with leakage of the filler material from the cavity 66 may be reduced.

FIG. 13 illustrates a containment assembly 88 having a containment jacket 90 that may be inserted into the cavity 66 (e.g., FIG. 7) in accordance with one embodiment of the present invention. As illustrated, the containment assembly 88 comprises a tubular member 92 (e.g., a cannula) having a proximal end 94 and a distal end 96. The tubular member 92 may be configured to allow passage of various instruments and materials into a vertebral body. The containment jacket 90 may be disposed on the distal end 96 of the tubular member 92. In the illustrated embodiment, the containment jacket 90 is in a deflated state. In an embodiment, the containment jacket 90 is impermeable, e.g., to the filler material. In some embodiments, the containment jacket 90 may be non-expandable. For the purposes herein, the containment jacket 90 is considered non-expandable if it does not expand at pressures that will be typically encountered during the procedures described herein. More particularly, the containment jacket 90 is considered to be non-expandable if the volume contained by the containment jacket 90 expands by less than its nominal volume. In implementation in certain embodiments, the containment jacket 90 is not expanded beyond its nominal volume. In other words, the containment jacket 90 is not stretched or increased in its surface area.

The containment jacket 90 may be constructed from any of a variety of suitable materials, including, for example, polyethylenes, polyethylene terephthalate, polyurethanes, thermoplastic elastomers (e.g., Pebax® resins, Bionate® PCU, Texin® TPU, Carbothane® TPU, Pellethane® TPE, Tecothane® TPU, Elastathane® TPU, Chronothane® TPU, Estane® TPU), polyvinyl chloride, silicon, polyamides, polyesters (e.g., polycaprolactone, polylactic acid) and nylon. In one embodiment, the containment jacket 90 may include Bionate® 90A PCU. It should be understood that the containment jacket 90 may be constructed from a material that bioresorbable or non-resorbable material in certain embodiments. In some embodiments, the containment jacket 90 may have a wall thickness of less than about 20 millimeters and, alternatively, less than about 10 millimeters. In some embodiments, the containment jacket 90 may have a shore hardness of less than about 200 A, alternatively, less than about 100 A. In one particular embodiment, the containment jacket 90 may have a shore hardness of about 25 Å to about 100 Å.

As illustrated, a hub 98 may be disposed on the proximal end 94 of the tubular member 92. The hub 98 may allow, for example, connection of the containment assembly 88 to other devices that may be used in a medical procedure. A guide wire or obturator 100 (e.g., a K-wire) may be disposed through the tubular member 92. As illustrated, the guide wire 100 may extend into the proximal end 94 of the tubular member 92 and out from the distal end 96 of the tubular member 92. In an embodiment, the containment jacket 90 is disposed on the portion of the guide wire 100 extending from the distal end 96 of the tubular member 92. For example, the containment jacket 90 may be wrapped around the portion of the guide wire 100 extending through the distal end 96 of the tubular member 92. In this manner, the guide wire 100 may facilitate insertion of the containment jacket 90 through the cannula 2 (e.g., FIG. 1). In the illustrated embodiment, a cap 102 is disposed on the end of the guide wire 100 extending from the proximal end 94 of the tubular member 92.

As illustrated by FIG. 14, the containment jacket 90 may be inserted through the cannula 2 and into the cavity 66 within the vertebral body 4. In an embodiment (not illustrated), the containment jacket 90 may be in a wrapped/deflated state when it is inserted into the cavity 66. After insertion, the containment jacket 90 may be unwrapped/inflated, as illustrated by FIG. 14. The containment jacket 90 may be inserted by sliding the tubular member 92 with the containment jacket 90 disposed thereon through the cannula 2 disposed in the vertebral body 4. In an embodiment, the hub 98 on the containment assembly 88 may be coupled to the cannula hub 10 disposed on the cannula 2. As illustrated, the hub 98 of the containment assembly 88 may threadedly engage the cannula hub 10. Once the containment jacket 90 has been placed, the guide wire 100 (e.g., FIG. 13) may be removed from the containment assembly 88, leaving the containment jacket 90 in place. The cap 102 (e.g., FIG. 13) may be used to facilitate removal of the guide wire 100.

Embodiments of the present technique for treating vertebral fractures may further include removing fluid (e.g., air) from within the containment jacket 90 that has been placed into the vertebral body 4. Any of a variety of different techniques may be used to remove air from within the containment jacket 90. In an embodiment, a syringe may be used remove the air. An example of a suitable syringe includes a VacLok™ syringe. As illustrated by FIG. 15, a syringe 104 may be coupled to the hub 98 of the containment assembly 88. The plunger 106 of the syringe 104 may then be withdrawn to create a partial vacuum so that air from within the containment jacket 90 flows into the syringe 104. Accordingly, the fluid in the containment jacket 90 may be removed. To maintain the vacuum on the containment jacket 90, for example, a valve 108 (e.g., a one-way valve) may be included in the hub 98, as illustrated by FIG. 16. In an embodiment, the valve 108 may hold at least about 30 psi of pressure. The valve 108 may be, for example, threaded into the hub 98. The syringe 104 may then be used to create a partial vacuum to remove air from the containment jacket 90. FIG. 16 illustrates a containment jacket 90 in a deflated state from which the air has been removed.

Figure 17:
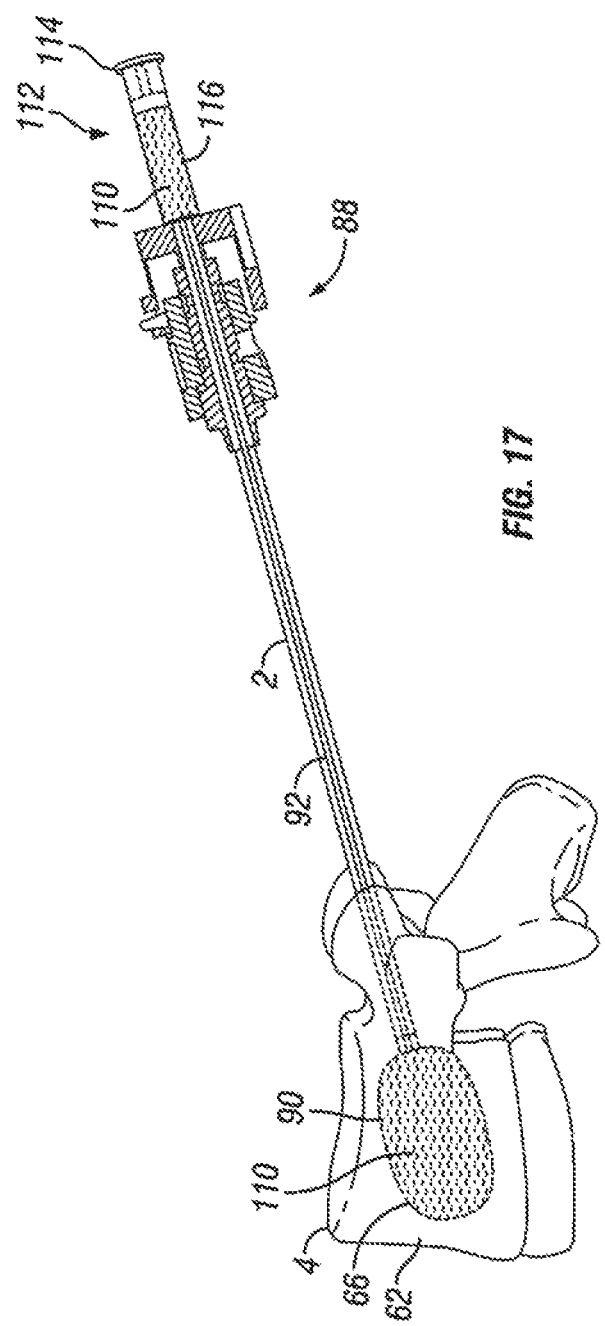
FIG. 17 illustrates use of a syringe-type device to introduce filler material into a containment jacket placed in a vertebral body in accordance with one embodiment of the present invention.

As previously mentioned, embodiments of the present invention may further include introduction of a filler material into the cavity 66. In an embodiment, the filler material may be introduced directly into the containment jacket 90 that has been placed within the cavity 66. FIG. 17 illustrates introduction of a filler material 110 into the containment jacket 90 in accordance with one embodiment of the present invention. As illustrated, the filler material 110 may be introduced into the containment jacket 90 using a syringe-type device 112. As illustrated, plunger 114 of the syringe-type device 112 may be depressed to force filler material 110 from the body 116 of the syringe-type device 112, through the tubular member 92 of the containment assembly 88, and into the containment jacket 90. In an embodiment, introduction of the filler material 110 into the containment jacket 90 should expand the containment jacket 90. In another embodiment, the containment jacket 90 does not expand. In some embodiments, the filler material 110 may be introduced into the containment jacket 90 until the containment jacket 90 at least partially fills the cavity 66 in the vertebral body 4. In some embodiments, the filler material 110 may be introduced at low pressure. In alternative embodiments, the filler material 110 should exert pressure to prevent (or reduce) loss of vertebral height. As illustrated, the containment jacket 90 may generally conform to the shape of the cavity 66. It may be desirable, in certain embodiments, for the containment jacket 90 to be a compliant balloon (e.g., polyurethane, collagen, silicone) that can contain the filler material 110 to prevent leakage. In some embodiments, the containment jacket 90 may permit interdigitation of the filler material 110 with the cancellous bone 62 while being contained within the containment jacket 90.

Figure 18:
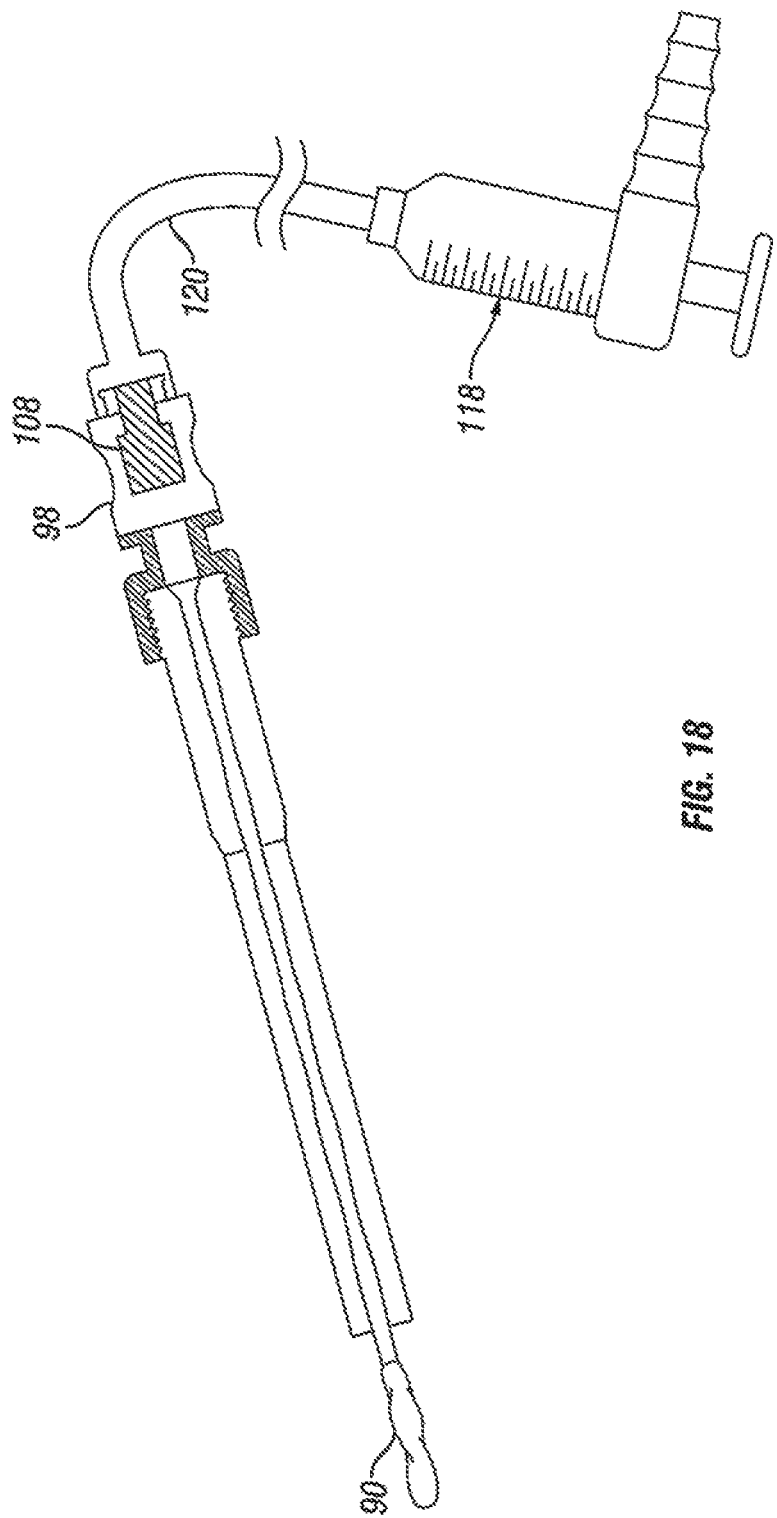
FIG. 18 illustrates use of a cement gun to introduce filler material into a containment jacket placed in a vertebral body in accordance with one embodiment of the present invention.
Figure 19:
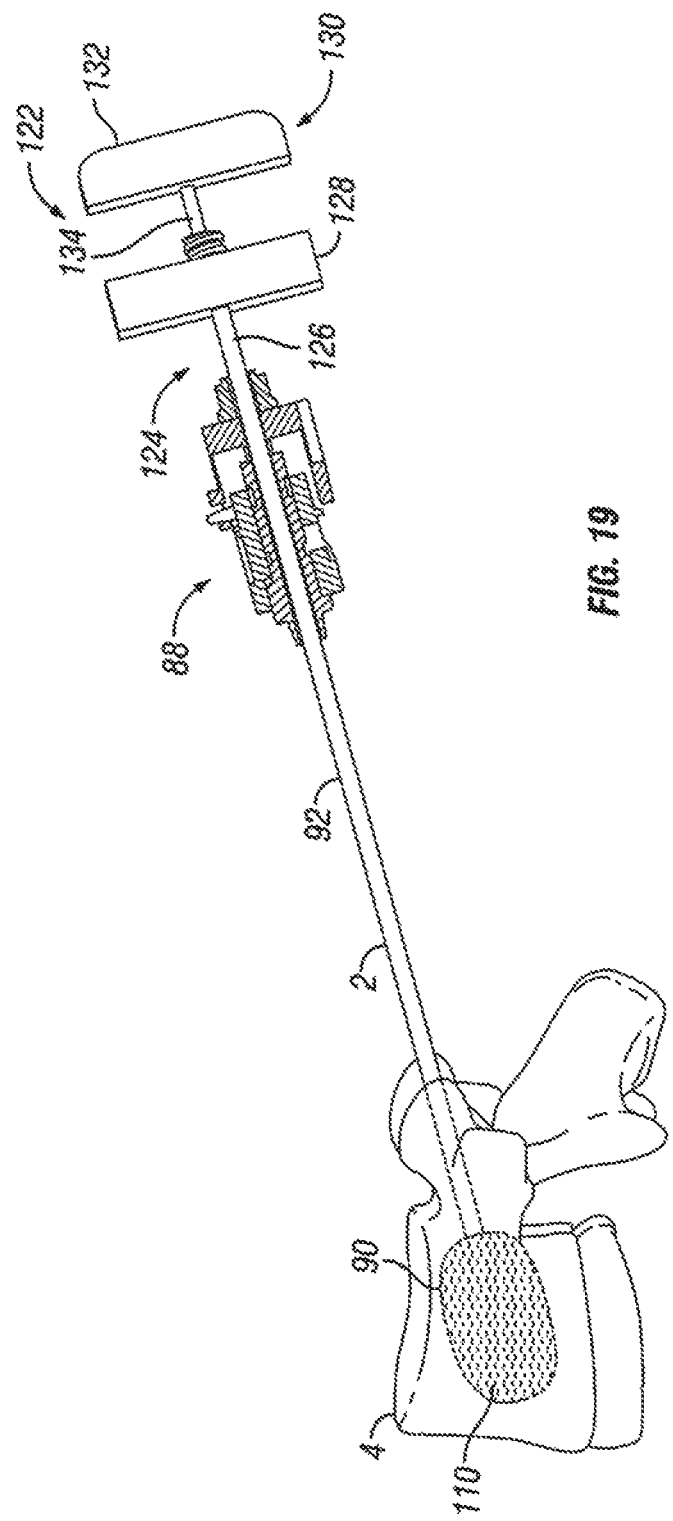
FIG. 19 illustrates use of a needle-type device to introduce filler material into a containment jacket placed in a vertebral body in accordance with one embodiment of the present invention.

While FIG. 17 illustrates use of syringe-type device 112 for introduction of the filler material 110, it should be understood that other suitable devices may be used to introduce the filler material 110 into containment jacket 90 within the vertebral body 4. For example, FIG. 18 illustrates a cement gun 118 that can be used for the injection into the containment jacket 90. In the illustrated embodiment, extension tube 120 couples the cement gun 118 to the valve 108 in the hub 98. By way of further example, FIG. 19 illustrates a needle-type device 122 that may be used to introduce the filler material 110. As illustrated, the body 124 of the needle-type device 122 may comprise a hollow tube 126 having a through passageway and a stop 128 at one end. The needle-type device 122 further may comprise a plunger 130 having a depression mechanism 132 and a needle 134 for insertion into the hollow tube 126, thereby driving the filler material 110 from the hollow tube 126 and into the containment jacket 90. In an embodiment, the body 124 of the needle-type device 122 may be inserted into the tubular member 92 of the containment assembly 88. Plunger 130 may then be depressed to force the filler material 110 from the body 124 of the needle-type device 122 and into the containment jacket 90.

In addition to introducing the filler material 110 directly into the containment jacket 90 as illustrated by FIGS. 17-19, alternative embodiments of the present invention may utilize a balloon assembly 50 while introducing the filler material 110 into the containment jacket 90. The balloon assembly 50 may be used, for example, to maintain and/or restore vertebral height while introducing the filler material 110.

FIG. 20 illustrates insertion of a balloon 58 through the cannula 2 and into a containment jacket 90 disposed within vertebral body 4 in accordance with one embodiment of the present invention. As previously discussed, embodiments include insertion of cannula 2 into the vertebral body 4 with the cannula 2 providing access into the vertebral body 4. As further discussed, embodiments also include insertion of the containment jacket 90 into the cavity 66 that was created in the vertebral body 4. In accordance with embodiments of the present invention, the balloon assembly 50 may be inserted into vertebral body 4. As illustrated, the balloon 58 may be inserted into the containment jacket 90 through the tubular member 92 of the containment assembly 88. In an embodiment, the balloon 58 may be in a deflated stated when inserted through the tubular member 92. The balloon 58 may be inserted by sliding the catheter 51 with the balloon 58 disposed thereon through the tubular member 92 of the containment assembly 88. Once the balloon 58 has been placed, the balloon assembly 50 may be coupled to the containment assembly 88. By way of example, cap 136 disposed on the catheter 51 of the balloon assembly 50 may thread onto a luer fitting 138 on the hub 98 of the containment assembly 88. In an alternative embodiment, the balloon assembly 50 may comprise luer cap (not illustrated) that may be configured to freely spin on catheter 51 of the balloon assembly 50, in certain embodiments. In an embodiment, the luer cap (not illustrated) may engage with the hub 98 of the containment assembly 88 to prevent movement of the balloon assembly 50 with respect to the containment assembly 88. In this manner, the balloon 58 can be precisely positioned within the vertebral body 4, for example.

After insertion of the balloon 58, fluid (e.g., air) may be removed from the containment jacket 90. The fluid may be removed, for example, in accordance with the previously discussed embodiments for removal of fluid from the containment jacket 90.

FIG. 21 illustrates inflation of balloon 58 after it has been inserted into the containment jacket 90 in accordance with one embodiment of the present invention. In general, inflation of the balloon 58 should provide pressure on the walls of the cavity 66 to prevent (or reduce) loss of vertebral height. It may be desirable, in certain embodiments, for expansion of the balloon 58 to further increase the height of the vertebral body 4. In certain embodiments, inflation of the balloon 58 may restore some vertebral height lost after the cavity 66 was initially created. As illustrated, the balloon 58 generally may be enclosed within the containment jacket 90. The volume of the balloon 58, when inflated, generally may be smaller than the volume of the containment jacket 90, in accordance with embodiments of the present invention. Furthermore, when inflated, the balloon 58 generally may not occupy the entire volume of the containment jacket 90. By way of example, the balloon 58 may occupy from about 25% to about 90% by volume of the containment jacket 90. In one embodiment, the balloon 58 may occupy from about 25% to about 60% by volume of the containment jacket 90.

Figure 22:
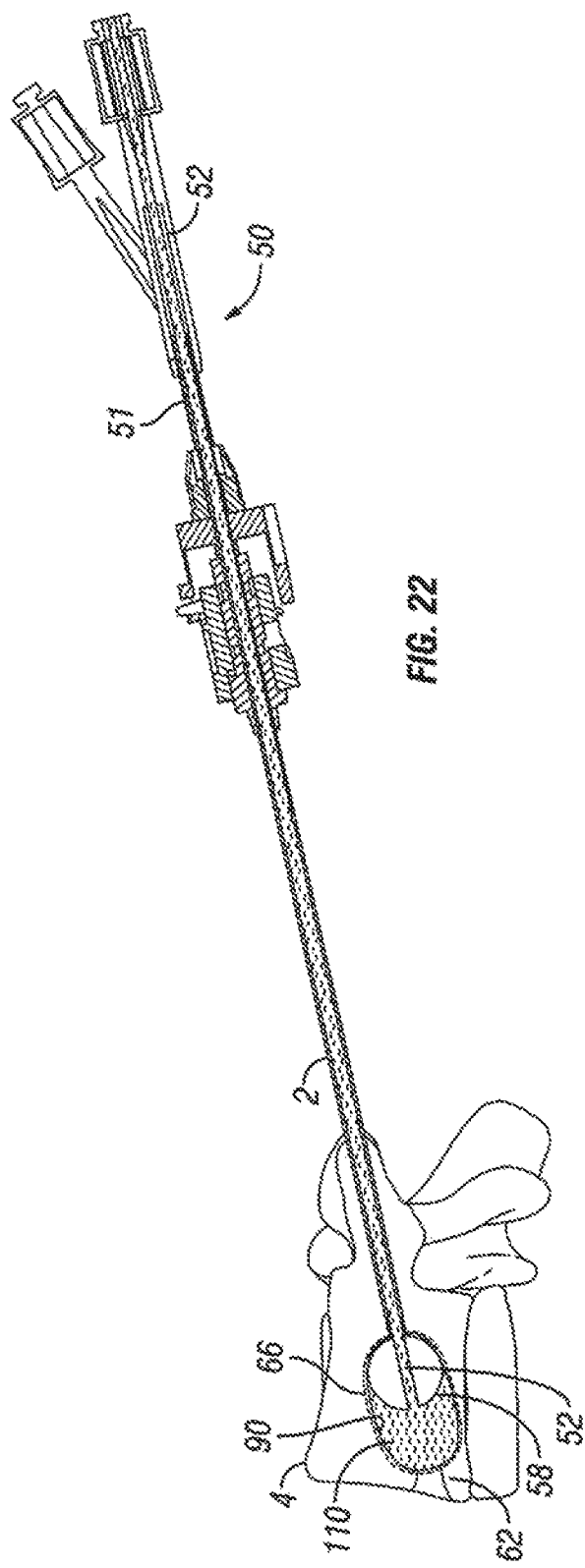
FIG. 22 illustrates introduction of a filler material into a vertebral body while using a balloon in accordance with one embodiment of the present invention.

FIG. 22 illustrates introduction of filler material 110 into the containment jacket 90 while balloon 58 is inflated therein, in accordance with one embodiment of the present invention. As illustrated, the filler material 110 may be introduced into the containment jacket 90 through the inner lumen 52 of the balloon assembly 50. While not illustrated by FIG. 22, any of a variety of suitable devices may be used for introduction of the filler material 110, including the devices illustrated by FIGS. 17-19, for example. In general, the filler material 110 may be introduced into the portion of the containment jacket 90 that is not occupied by the balloon 58. In an embodiment, the filler material 110 may fill the portion of the containment jacket 90 that is not occupied by the balloon 58. The containment jacket 90 may expand with the introduction of the filler material 110. In another embodiment, the containment jacket 90 does not expand upon introduction of the filler material 110. The filler material 110 may then be allowed to cure in the containment jacket 90. In an embodiment, the filler material 110 may exert pressure to prevent (or reduce) loss of vertebral height. It may be desirable, in certain embodiments, for the filler material 110 to exert pressure that further increases height of the vertebral body 4. As illustrated, the containment jacket 90 may generally conform to the shape of the cavity 66. It may be desirable, in certain embodiments, for the containment jacket 90 to be a complaint balloon (e.g., polyurethane) that can contain the filler material 110 to prevent leakage while permitting interdigitation of the filler material 110 with the cancellous bone 62.

Figure 23:
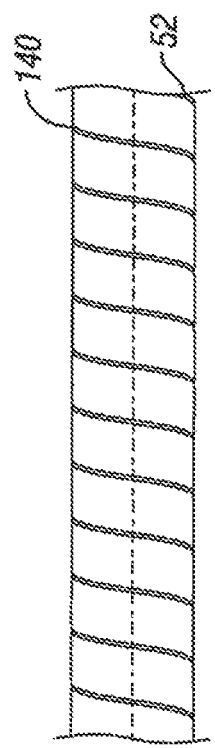
FIG. 23 illustrates reinforcement of an inner lumen of a balloon assembly in accordance with one embodiment of the present invention.

Those of ordinary skill in the art will appreciate that the inner lumen 52 of the balloon assembly 50 may be exposed to high pressures, in some embodiments, when the balloon 58 is inflated. This may be particularly true for the portion of the inner lumen 52 that extends into the balloon, as best seen on FIG. 22. Due to the high pressures, the inner lumen 52 may deform and even potentially collapsed during inflation. However, if the inner catheter is deformed, such deformation may undesirably interfere with introduction of the filler material 110 through the inner lumen 52. Accordingly, to prevent collapse of the inner lumen 52, the inner lumen 52 may be reinforced in accordance with embodiments of the present invention. FIG. 23 illustrates an inner lumen 52 that has been reinforced with a coil 140, for example, to reduce the tendency for the inner lumen 52 to undesirably deform at high pressures. In an embodiment, the coil 140 may be a metal coil, such a stainless steel coil.

Filler material 110 generally comes into contact with the balloon 58 when the filler material 110 is introduced into the containment jacket 90 in accordance with embodiments of the present invention. For example, when the filler material 110 is introduced through the inner lumen 52 of the balloon assembly 50, the filler material 110 may accumulate, for example, on the distal face of the balloon 58. It should be understood that the balloon 58 may burst when it is under stress from inflation and comes into contact with the filler material 110.

Embodiments of the present invention may include a number of different techniques to reduce or potentially even prevent the potential bursting of the balloon 58 when the filler material 110 is introduced. For example, properties of the balloon 58 may be modified to increase its resistance to the filler material 110. In an embodiment, the shore hardness of the balloon 58 may be increased. For example, the shore hardness may be increased from a range of about 80 A to about 90 A to at least about 100 A (e.g., about 100 A to about 120 A). In another embodiment, the wall thickness of the balloon 58 may be increased. The wall thickness may be increased, for example, from a range of about 0.1 mm to about 0.15 mm to a range of about 0.175 mm to about 0.2 mm. An additional technique may include applying a protective barrier (e.g., silicone, a hydrophobic material, Parylene poly(p-xylylene) polymers, etc). Another technique may include cross-linking the balloon material, for example, via gamma sterilization.

Figure 24:
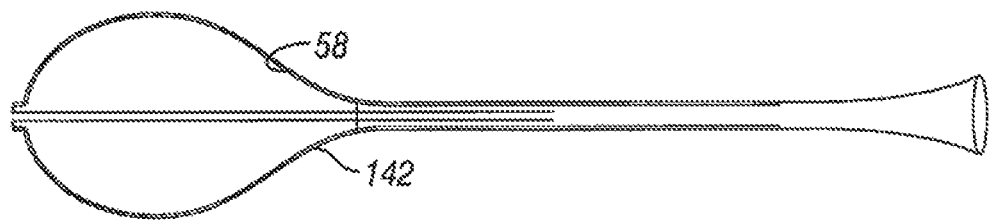
FIGS. 24-28 illustrate isolation of the balloon from the filler material in accordance with embodiments of the present invention.
Figure 25:
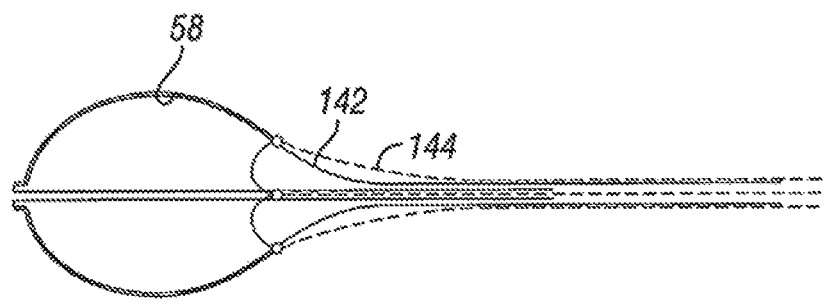
Figure 26:
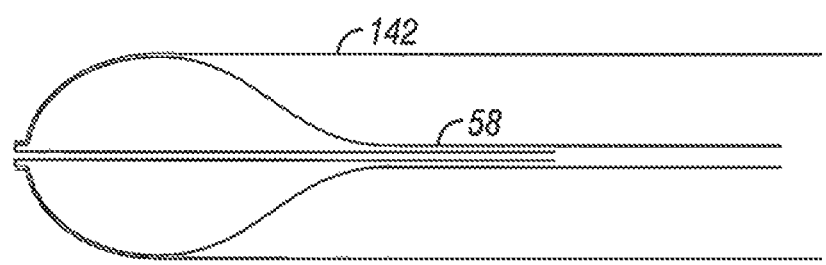
Figure 27:
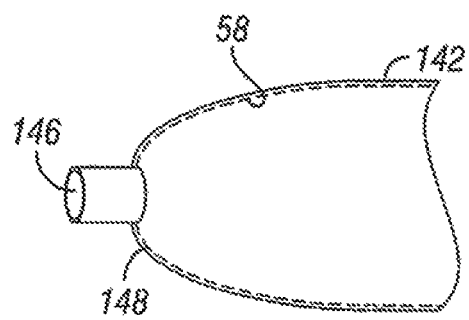
Figure 28:
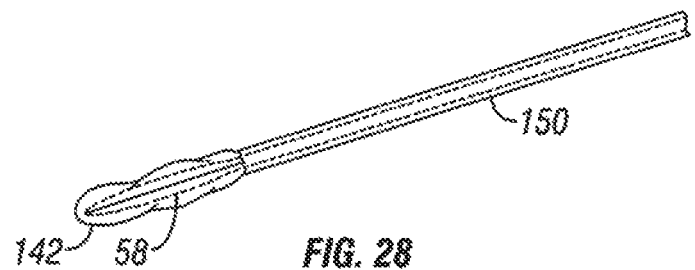

Additional techniques may include isolating the balloon 58 from the filler material 110 introduced into the containment jacket 90. FIGS. 24-28 illustrate a protective enclosure 142 disposed over the balloon 58 to prevent contact with the filler material 110 in accordance with various embodiments of the present invention. In an embodiment, the enclosure 142 may be fabricated with a material with high resistant to bone cement (e.g., polymethyl methacrylate). The material may also have a lower moisture vapor transmission rate, in certain embodiments. By way of example, the moisture vapor transmission rate may be less than about 1 g/100 in$^2$/day. As illustrated by FIG. 24, enclosure 142 may be placed over the balloon 58. As illustrated, the enclosure 142 may have a profile generally corresponding to the profile of the balloon 58. However, the enclosure 142 should generally be unstressed when the balloon 58 is inflated in accordance with certain embodiments. FIG. 25 illustrates an embodiment of the enclosure 142 having threads 144 holding the enclosure 142 in place over the balloon 58. In an embodiment (not illustrated), the threads 144 may be stitched to the balloon 58. FIGS. 26-28 illustrate alternate embodiments for placement of the enclosure 142 over the balloon 58. As illustrated by FIG. 26, embodiments may include an enclosure 142 that loosely fits over the balloon 58. As illustrated by FIG. 27, embodiments may include the nose 146 of the enclosure 142 fitting tightly over the nipple 148 of the balloon 58. In an embodiment (not illustrated), a bonding agent may be used to bond the nipple 148 of the balloon 58 to the nose 146 of the enclosure 144. FIG. 28 illustrates an embodiment with the enclosure 142 disposed on one end of a tube 150. In an embodiment, the enclosure 142 may be stitched onto the end of the tube 150. As illustrated, the balloon 58 may be placed inside the enclosure 142.

Figure 29:
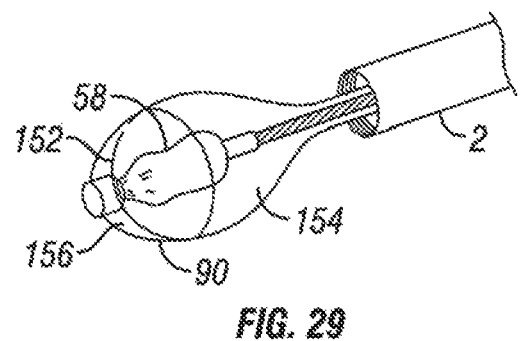
FIGS. 29-30 illustration a containment jacket with a dividing wall for isolation of a balloon from filler material in accordance with one embodiment of the present invention.
Figure 30:
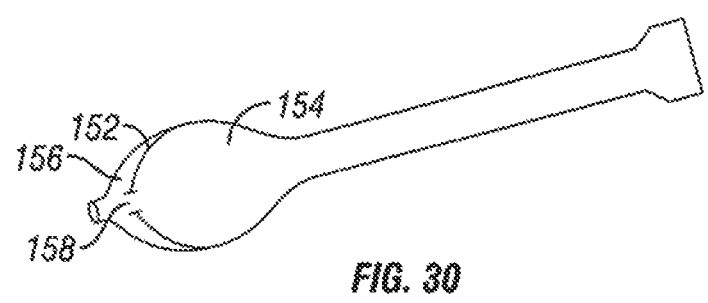

FIGS. 29 and 30 illustrate yet one technique for isolating the balloon 58 from the filler material 110 in accordance with one embodiment of the present invention. In the illustrated embodiment, the containment jacket 90 includes a dividing wall 152 that separates the containment jacket 90 into a proximal region 154 and a distal region 156. As illustrated, the dividing wall 152 may include an opening 158 for providing access to the region 156 from the proximal region 158. As illustrated, the balloon 58 may be inserted into the proximal region 158 of the containment jacket 90. While not illustrated, filler material 110 may then be introduced into the distal region 156 with the dividing wall 152 isolating the balloon 58 from the filler material 110. In an embodiment (not illustrated), the balloon 58 may be inflated in the proximal region 158, and then the filler material 110 may be introduced into the distal region 156. In an alternative embodiment (not illustrated), the balloon 58 may first be inflated in the distal region 156. The balloon 58, for example, may be threaded through the opening 158 and into the distal region 156. FIGS. 68-75 below illustrate construction and use of a containment jacket 90 with a dividing wall 152 in more detail in accordance with embodiments of the present invention.

Figure 31:
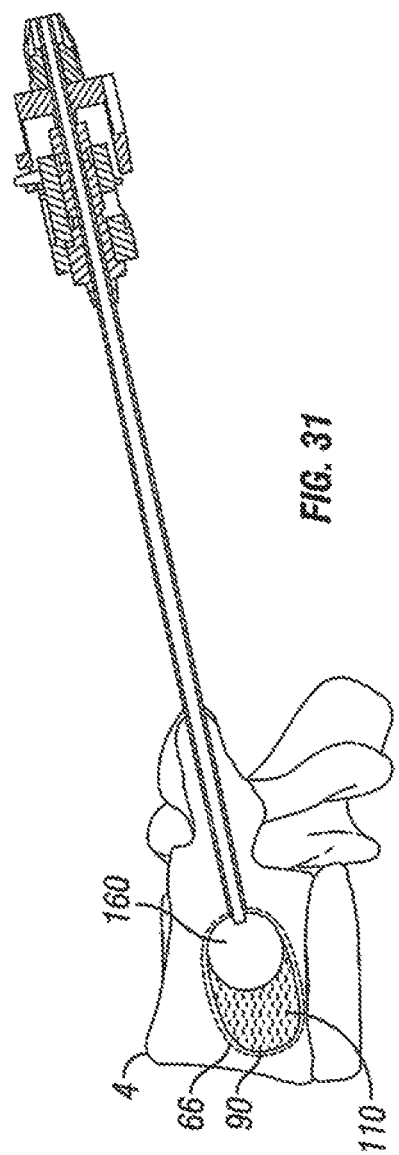
FIG. 31 illustrates a containment jacket placed within a vertebral body that has been partially filled in accordance with one embodiment of the present invention.

As illustrated by FIG. 31, after the filler material 110 has been allowed to cure, the balloon assembly 56 (e.g., FIG. 22) may be removed from the containment jacket 90 in the vertebral body 4. With removal of the balloon 58, a portion of the containment jacket 90 is not occupied. This unoccupied portion of the containment jacket 90 is represented on FIG. 66 by reference number 160.

Figure 32:
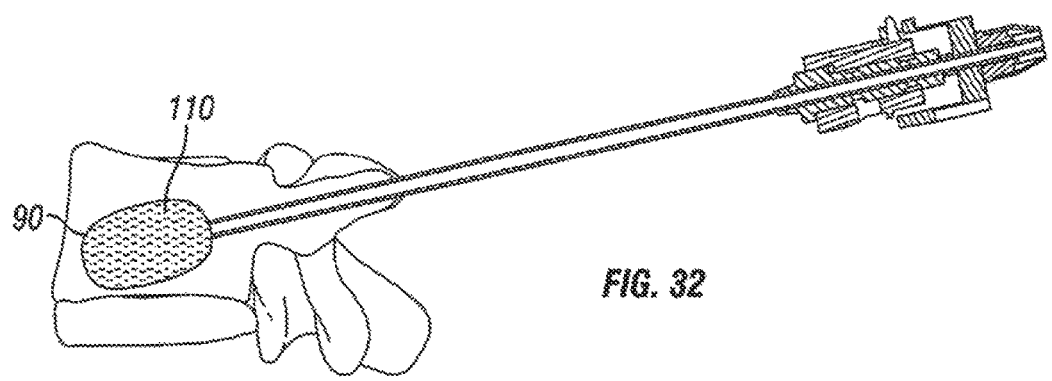
FIG. 32 illustrates introduction of filler material to fill the remainder of a containment jacket placed within a vertebral body in accordance with one embodiment of the present invention.

FIG. 32 illustrates introduction of an additional volume of the filler material 110 into the containment jacket 90. The additional volume of the fill material may generally fill the unoccupied portion 160 (e.g., FIG. 31) of the containment jacket 90 so that the containment jacket 90 is filled with the filler material 110, for example. While not illustrated by FIG. 32, any of a variety of suitable devices may be used for introduction of the additional volume of the filler material 110 including the devices illustrated by FIGS. 17-19. The additional volume of the filler material 110 may then be allowed to cure in the containment jacket 90.

Figure 33:
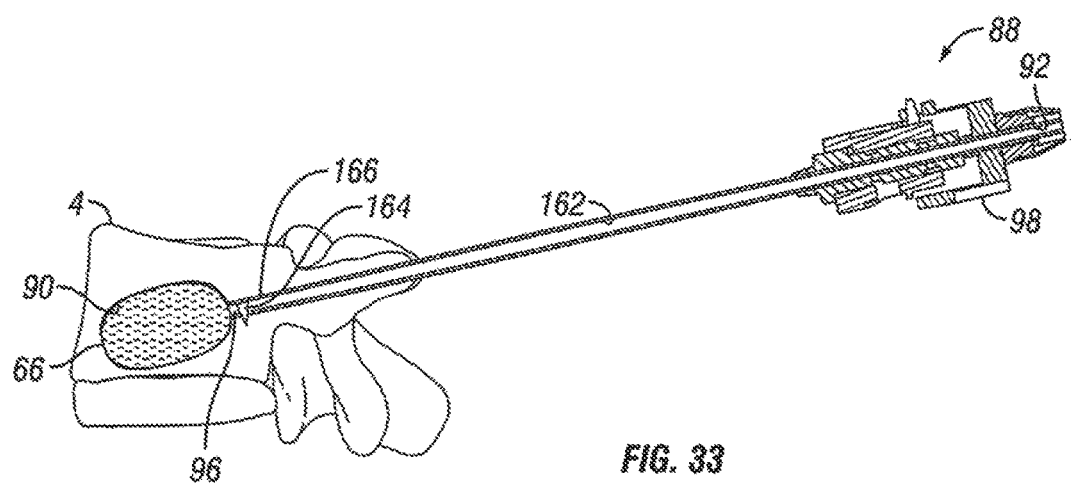
FIG. 33 illustrates detachment of the containment jacket from a containment assembly in accordance with one embodiment of the present invention.

Embodiments of the present invention further may include detaching the containment jacket 90 from the containment assembly 88. FIG. 33 illustrates removal of the containment jacket 90 in accordance with one embodiment of the present invention. As previously mentioned, the containment jacket 90 may be attached to the distal end 96 of the tubular member 92. As illustrated, a cutting device 162 having a cutting mechanism (e.g., cutting tips 164) in its distal end 166 may be inserted into the tubular member 92. In an embodiment, the cutting tips 164 include one or more blades. The cutting device 162 may then be used to detach the containment jacket 90, leaving the containment jacket 90 within the vertebral body 4. Once the containment jacket 90 has been detached, the containment assembly 88 and the cannula assembly 10 may be removed, leaving the containment jacket 90 in the vertebral body 4. Accordingly, the containment jacket 90 containing the filler material 110 may be left within the vertebral body 4.

While the preceding discussion describes the use of cutting device 162 to detach the containment jacket 90, it should be understood that other suitable techniques may be used for detachment. In an alternative embodiment, the containment jacket 90 has perforations (not illustrated) on the neck wherein twisting the hub 98 of the containment assembly 88 detaches the containment jacket 90 at the perforations. Another embodiment may include a thread (not illustrated), that secures the containment jacket 90 to the tubular member 92 of the containment assembly 88. While not illustrated, a cord may extend from the thread that can be pulled to unravel the thread, detaching the containment jacket 90 from the tubular member 92.

Figure 34:
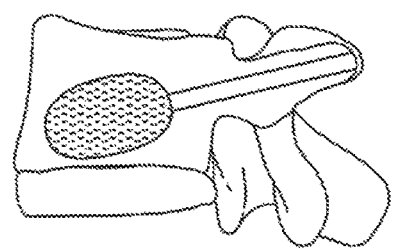
FIG. 34 illustrates a containment jacket placed within a vertebral body, the containment jacket containing a filler material, in accordance with one embodiment of the present invention.

FIG. 34 illustrates a containment jacket 90 that has been placed into a vertebral body 4 and filled with filler material 110 in accordance with one embodiment of the present invention. As previously mentioned, the filler material 110 may be introduced directly into the containment jacket 90 in accordance with embodiments of the present invention. As further discussed, a balloon assembly 50 (FIGS. 20-22) may be used while introducing the filler material 110 into the containment jacket 90 in accordance with alternative embodiments of the present invention. In an embodiment, the filler material 110 may be introduced at low pressure. In an alternative embodiment, the filler material 110 may exert pressure to prevent (or reduce) loss of vertebral height.

Figure 35:
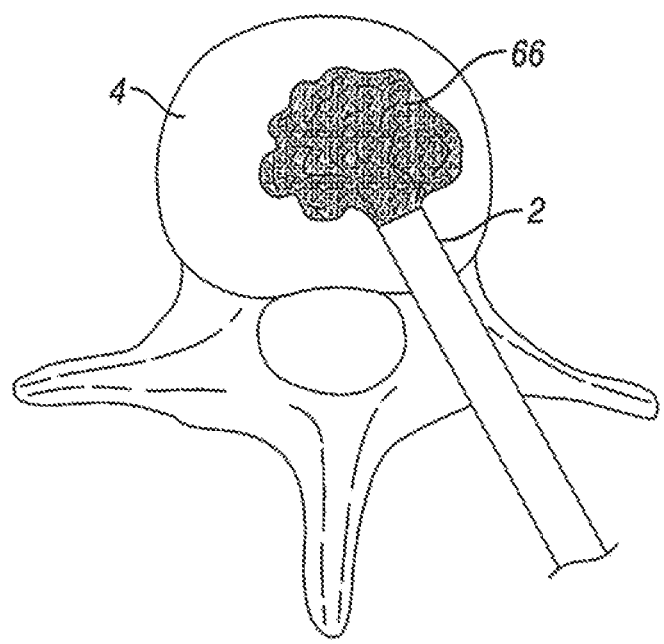
FIGS. 35-38 illustrate treatment of a vertebral fracture in accordance with another embodiment of the present technique.
Figure 36:
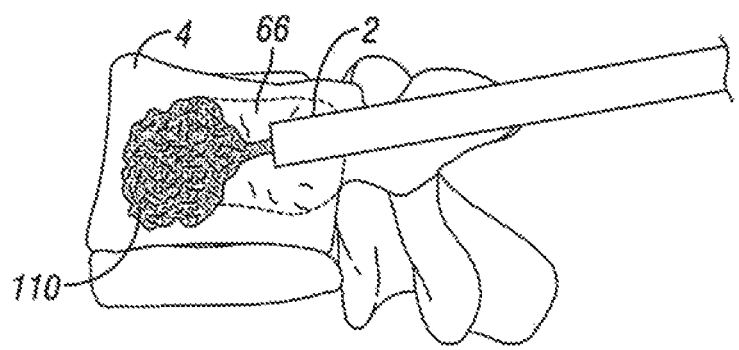

FIGS. 35-38 illustrate another technique for treating a fracture in vertebral body 4 in accordance with embodiments of the present invention. In contrast to the techniques discussed above, the embodiment illustrated by FIGS. 35-38 does not use a containment jacket 90 (e.g., FIG. 13). As illustrated by FIG. 35, cavity 66 may created in the vertebral body 4. As previously discussed, the cavity 66 may be formed using any of a variety of different techniques, including, for example, using an inflatable balloon 58 (e.g., FIG. 7), a mechanical device 68 (e.g., FIG. 9), or a combination of both. As illustrated, cannula 2 should extend into the cavity 66, providing access to the cavity 66. After creation of the cavity 66, a first portion of bone filler 110 may be inserted into the cavity 66, as best seen in FIG. 36. As illustrated, the first portion of the bone filler 110 may be inserted into an anterior portion of the cavity 66. While not illustrated by FIG. 35, any of a variety of different devices may be used for introduction of the filler material 110 including the devices illustrated by FIGS. 17-19.

Figure 37:
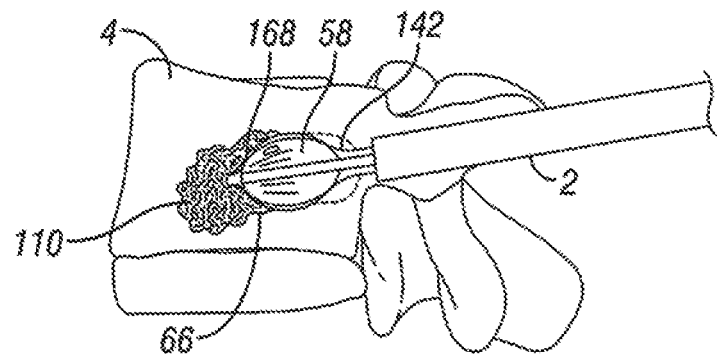
Figure 38:
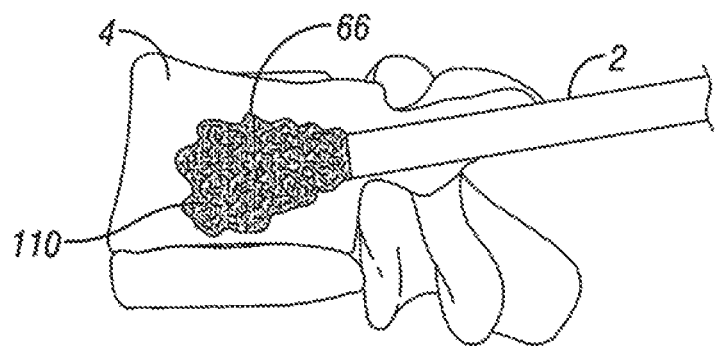

As illustrated by FIG. 37, before the filler material 110 has substantially cured, e.g., formed into a hardened mass, a balloon 58 may be inserted into the cavity 66 and inflated. By inflating the balloon 58 in the cavity 66 while the filler material 110 is curing, vertebral height may be maintained during curing. In this manner, loss of vertebral height may be prevented, which could occur during curing of the filler material 110 without inflation of the balloon 58. In the illustrated embodiment, the balloon 58 is disposed within container 142. Techniques for disposing the balloon 58 in the container 142 are discussed in more detail above with respect to FIGS. 24-28. As previously discussed, the container 142 should isolate the balloon 58 from the filler material 110 to reduce the potential for its bursting when contacted by the filler material 110. The first volume of the filler material 110 should pack around the anterior face 168 of the container 142. In an embodiment, the filler material 110 may then be allowed to cure, followed by deflation of the balloon 58 and removal of the balloon 58 and container 142 from the vertebral body 4. As illustrated by FIG. 38, an additional volume of filler material 110 may then be inserted into the remaining volume of the cavity 66.

Treatment of Vertebral Body—Bi-Pedicular Approaches

Those of ordinary skill in the art, with the benefit of this disclosure, should approach that it may be desired, in some embodiments, to employ a bi-pedicular approach for treatment of a fracturing in the vertebral body 4. For example, if a bi-pedicular approach is desired, the steps discussed above may be repeated on the alternate side of the vertebral body 4 after the vertebral body 4 has been treated from the other side.

Figure 39:
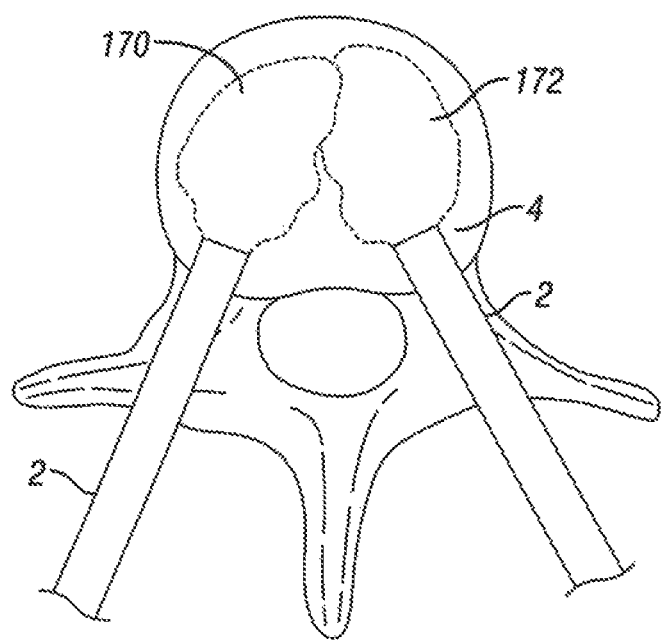
FIGS. 39-42 illustrate a bi-pedicular technique for treating a vertebral fracture in accordance with one embodiment of the present invention.

FIGS. 39-42 illustrate a bi-pedicular approach for treating a fracture in vertebral body 4 in accordance with embodiments of the present invention. In a similar manner to the embodiment described with respect to FIGS. 35-38, the embodiment illustrated by FIGS. 39-42 does not use a containment jacket 90 (e.g., FIG. 13). As illustrated by FIG. 39, cavities 170, 172 may be created in the left and right regions of the vertebral body 4. In an embodiment, the cavities 170, 172 may be created in a serial fashion, for example, first in the left cavity 170 and then in the right cavity 172 or, alternatively, first in the right cavity 172 and then in the left cavity 170. The cavities 170, 172 may be formed using any of a variety of different techniques, including, for example, using an inflatable balloon 58 (e.g., FIG. 7), a mechanical device 68 (e.g., FIG. 9), or a combination of both. As illustrated, a cannula 2 should extend into each of the cavities 170, 172 providing access to the cavities 170, 172.

Figure 40:
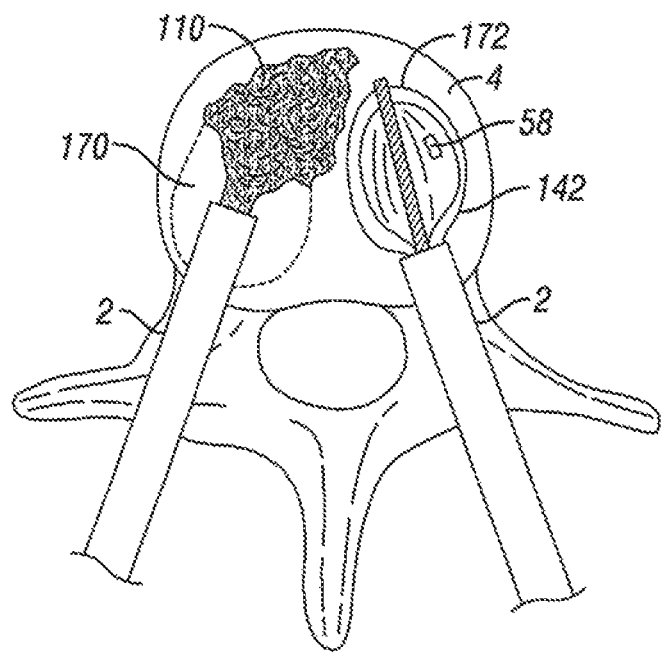

As illustrated by FIG. 40, after creation of the cavities 170, 172, a balloon 58 may be inserted into one of the cavities 170, 172 and inflated in accordance with one embodiment. FIG. 40 illustrates an inflated balloon 58 disposed within the right cavity 172. Alternatively, if inflatable balloons were used for cavity creation, a balloon 58 may be left in the right cavity 172 in the inflated state with deflation and removal of the balloon 58 that was used to create the left cavity 170. Having the balloon 58 in an inflated state in the right cavity 172 should prevent loss of restored vertebral height that would occur if both balloons were deflated and removed from the cavities 170, 172. In an alternative embodiment (not illustrated), a balloon 58 may be left in an inflated state in the left cavity 170 with deflation and removal of the balloon 58 that was used to create the right cavity 172. In the illustrated embodiment, the balloon 58 is disposed within container 142. Techniques for disposing the balloon 58 in the container 142 are discussed in more detail above with respect to FIGS. 24-28. As previously discussed, the container 142 should isolate the balloon 58 from the filler material 110 to reduce the potential for its bursting when contacted by the filler material 110.

Figure 41:
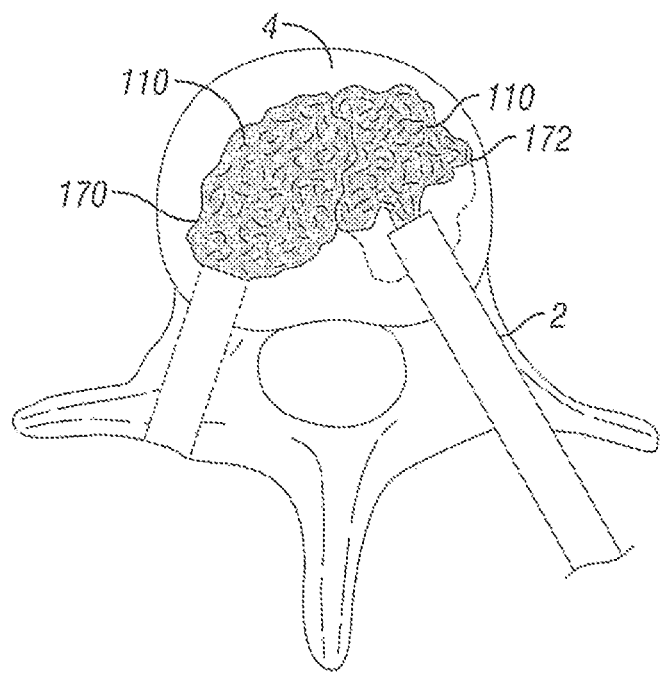
Figure 42:
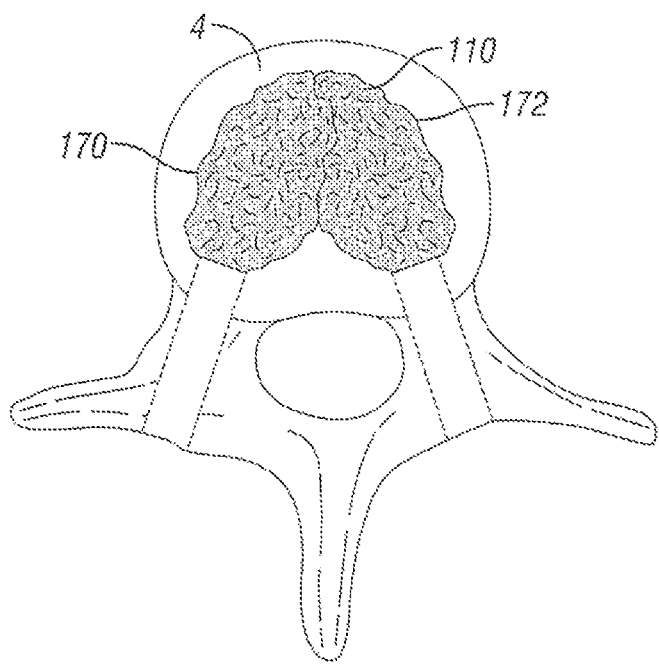

With the balloon 58 inflated in the right cavity 172, filler material 110 may be placed into the left cavity 170, as illustrated by FIG. 40. In an embodiment, the filler material 110 may then be allowed to cure, followed by deflation of the balloon 58 and removal of the balloon 58 and container 142 from the right cavity 172 in the vertebral body 4. As illustrated by FIG. 41, filler material 110 may then be placed into the right cavity 172 that was previously occupied by the balloon 58. While not illustrated by FIGS. 40 and 41, any of a variety of different devices may be used for introduction of the filler material 110 including the devices illustrated by FIGS. 17-19. FIG. 42 illustrates the vertebral body 4 in which filler material 110 has been placed into cavities 170, 172 in accordance with embodiments. While the preceding description describes, placement of filler material 110 into the left cavity 170 first followed by placement of filler material 110 into the right cavity 172, it should be understood that, in some embodiments, the steps may be reversed with the filler material being first placed into the right cavity 172.

Figure 43:
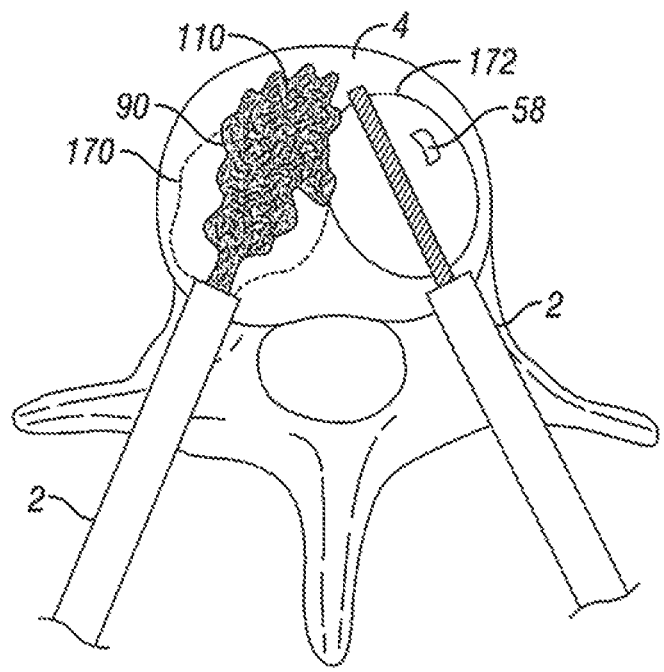
FIGS. 43-45 illustrate a bi-pedicular technique for treating a vertebral fracture in accordance with another embodiment of the present invention.
Figure 44:
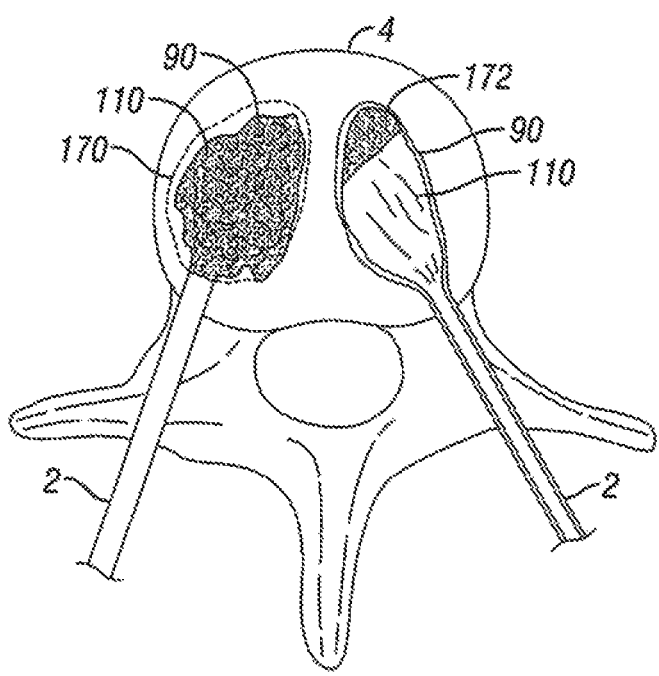
Figure 45:
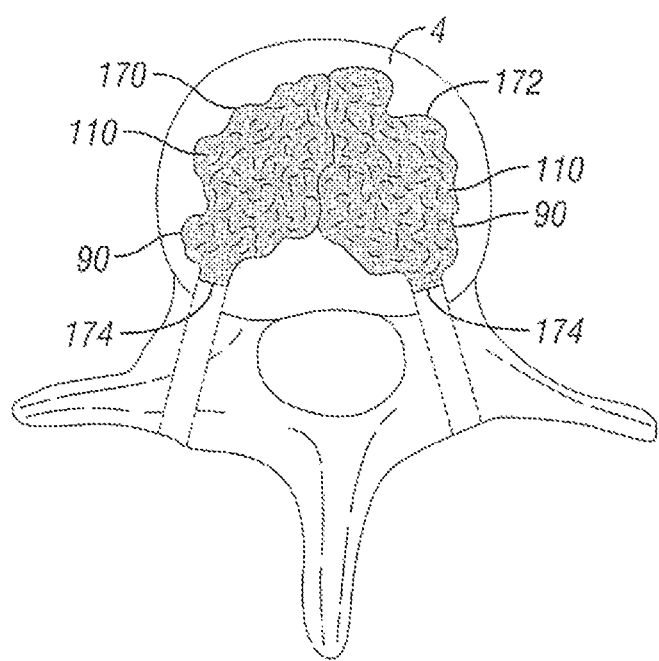

FIGS. 43-45 illustrate another bi-pedicular approach for treating a fracture in vertebral body 4 in accordance with embodiments of the present invention. In contrast to the embodiment described above with respect to FIGS. 39-42, the embodiment shown on FIGS. 43-45 employs a containment jacket 90 (e.g., FIG. 13). As illustrated by FIG. 43, cavities 170, 172 may be created in the left and right regions of the vertebral body 4. In an embodiment, the cavities 170, 172 may be created in a serial fashion, for example, first in the left cavity 170 and then in the right cavity 172 or, alternatively, first in the right cavity 172 and then in the left cavity 170. The cavities 170, 172 may be formed using any of a variety of different techniques, including, for example, using an inflatable balloon 58 (e.g., FIG. 7), a mechanical device 68 (e.g., FIG. 9), or a combination of both. As illustrated, a cannula 2 should extend into each of the cavities 170, 172 providing access to the cavities 170, 172.

As illustrated by FIG. 43, after creation of the cavities 170, 172, a balloon 58 may be inserted into one of the cavities 170, 172 and inflated in accordance with one embodiment. FIG. 43 illustrates an inflated balloon 58 disposed within the right cavity 172. Alternatively, if inflatable balloons were used for cavity creation, the balloon 58 may be left in the right cavity 172 in the inflated state with deflation and removal of the balloon 58 that was used to create the left cavity 170. Having the balloon 58 in an inflated state in the right cavity 172 should prevent loss of restored vertebral height that would occur if each balloon 58 was deflated and removed from the cavities 170, 172. In an alternative embodiment (not illustrated), a balloon 58 may be left in an inflated state in the left cavity 170 with deflation and removal of the balloon 58 that was used to create the right cavity 172. While not illustrated by FIG. 43, the balloon 58 may be disposed in a container 142 (FIGS. 24-28) in one particular embodiment.

With the balloon 58 inflated in the right cavity 172, a containment jacket 90 may be placed into the left cavity 170, as illustrated by FIG. 43. In an embodiment, filler material 110 may then be placed into the containment jacket 90 that is in the left cavity 170. While not illustrated by FIG. 43, any of a variety of different devices may be used for introduction of the filler material 110 including the devices illustrated by FIGS. 17-19. In one particular embodiment, the filler material 110 in the containment jacket 90 may then be allowed to cure, followed by deflation of the balloon 58 and removal of the balloon 58 from the right cavity 172 in the vertebral body 4.

As illustrated by FIG. 44, a containment jacket 90 may then be placed into the right cavity 172 that was previously occupied by the balloon 58. In an embodiment, filler material 110 may then be placed into the containment jacket 90 that is in the right cavity 172. While not illustrated by FIG. 44, any of a variety of different devices may be used for introduction of the filler material 110 including the devices illustrated by FIGS. 17-19. The filler material 110 in the right cavity 172 may then be allowed to cure.

Embodiments may further include detaching the containment jacket 90 in each of the cavities 170, 172 such that the containment jacket 90 containing the filler material 110 remains in each of the cavities 170, 172, as illustrated by FIG. 45. In an embodiment, the containment jackets 90 may be detached in a serial fashion, for example, first in the left cavity 170 and then in the right cavity 172 or, alternatively, first in the right cavity 172 and then in the left cavity 170. In one embodiment, a cutting device 162 (e.g., FIG. 33) may be used to detach each containment jacket 90 at their respective necks 174. While the preceding description describes, placement and filling of the containment jacket 90 in left cavity 170 first followed by placement and filling of the containment jacket 90 in the right cavity 172, it should be understood that, in some embodiments, the steps may be reversed with the containment jacket 90 being first placed and filled in the right cavity 172.

Figure 46:
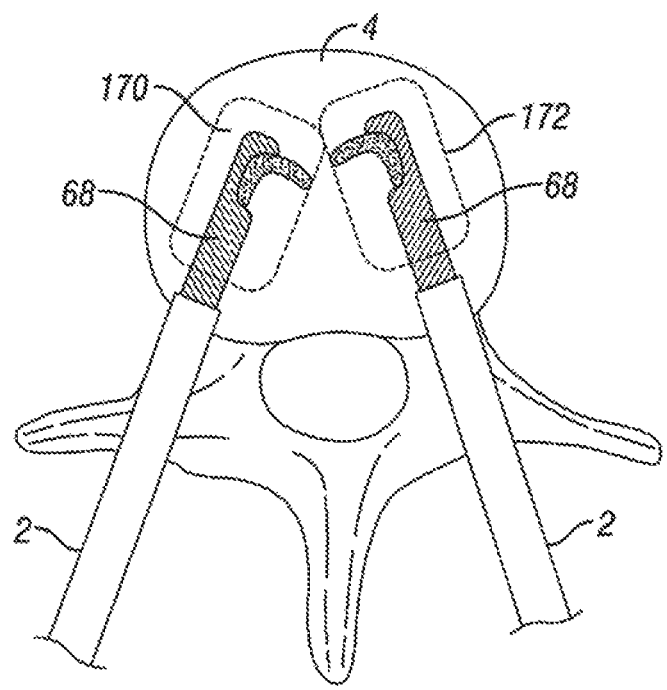
FIGS. 46-49 illustrate a bi-pedicular technique for treating a vertebral fracture in accordance with yet another embodiment of the present invention.

FIGS. 46-49 illustrate another bi-pedicular approach for treating a fracture in vertebral body 4 that employs a containment jacket 90 (e.g., FIG. 13) in accordance with embodiments of the present invention. As illustrated by FIG. 46, embodiments may include creations of cavities 170, 172 in the left and right regions of the vertebral body 4 with a mechanical device 68. In one embodiment, the cavities 170, 172 may be created in a serial fashion, for example, first in the left cavity 170 and then in the right cavity 172 or, alternatively, first in the right cavity 172 and then in the left cavity 170. The cavities 170, 172 may be formed using any of a variety of different techniques, including, for example, using an inflatable balloon 58 (e.g., FIG. 7), a mechanical device 68 (e.g., FIG. 46), or a combination of both. As illustrated, a cannula 2 should extend into each of the cavities 170, 172 providing access to the cavities 170, 172.

Figure 47:
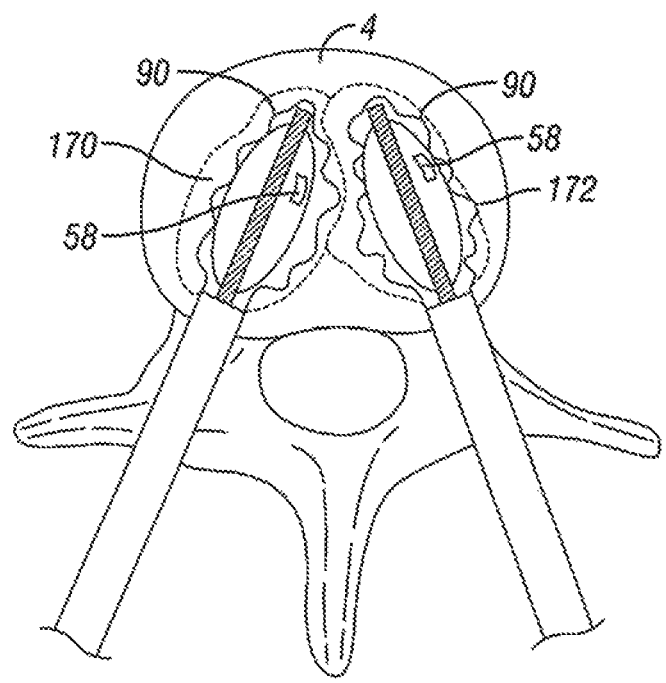

As illustrated by FIG. 47, after creation of the cavities 170, 172, a containment jacket 90 and a balloon 58 may be inserted into each of the cavities 170, 172, in accordance with one embodiment. Embodiments may include inflation of the balloon 58 in each of the cavities 170, 172. In one embodiment, the containment jacket 90 may be inserted followed by insertion of the balloon 58 into the containment jacket 90. In another embodiment, the containment jacket 90 may be inserted with the balloon 58 disposed therein. In one particular embodiment (not illustrated) a containment jacket 90 and balloon 58 may be inserted into only one of the cavities 170, 172 with only a containment jacket 90 inserted into the other one of the cavities 170, 172.

Figure 48:
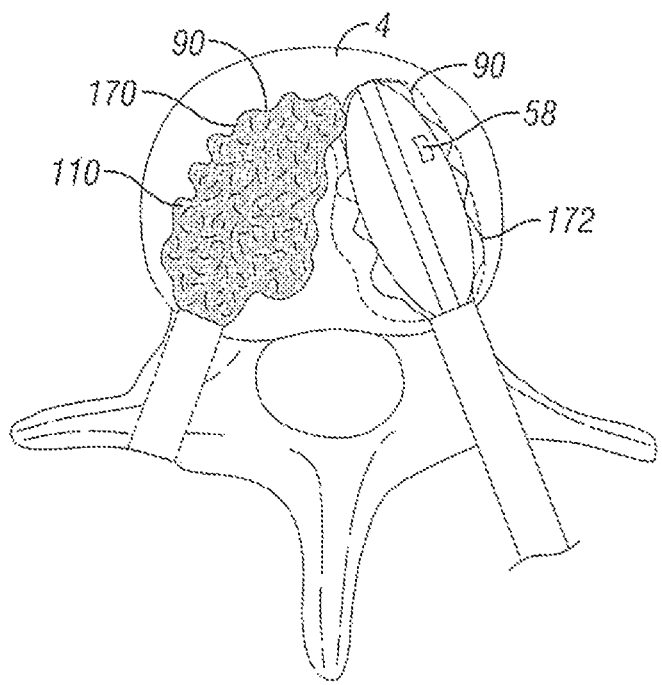

Embodiments may further include deflation and removal of a balloon 58 from one of the cavities 170, 172. FIG. 48 illustrates an embodiment in which the balloon 58 has been deflated and removed from the left cavity 170 leaving the containment jacket 90 in the left cavity 170 and inflated balloon 58 and containment jacket 90 in the right cavity 172. Having the balloon 58 in an inflated state in the right cavity 172 should prevent loss of restored vertebral height that would occur if both balloons were deflated and removed from the cavities 170, 172.

As illustrated by FIG. 48, with the balloon 58 inflated in the right cavity 172, filler material 110 may then be placed into the containment jacket 90 that is in the left cavity 170. In one particular embodiment, the filler material 110 in the containment jacket 90 may then be allowed to cure, followed by deflation and removal of the balloon 58 from the right cavity 172 in the vertebral body 4. In an embodiment, filler material 110 may then be placed into the containment jacket 90 that is in the right cavity 172. While not illustrated by FIGS. 47 and 48, any of a variety of different devices may be used for introduction of the filler material 110 including the devices illustrated by FIGS. 17-19. The filler material 110 in the right cavity 172 may then be allowed to cure. While the preceding description describes, placement and filling of the containment jacket 90 in left cavity 170 first followed by placement and filling of the containment jacket 90 in the right cavity 172, it should be understood that, in some embodiments, the steps may be reversed with the containment jacket 90 being first placed and filled in the right cavity 172.

Figure 49:
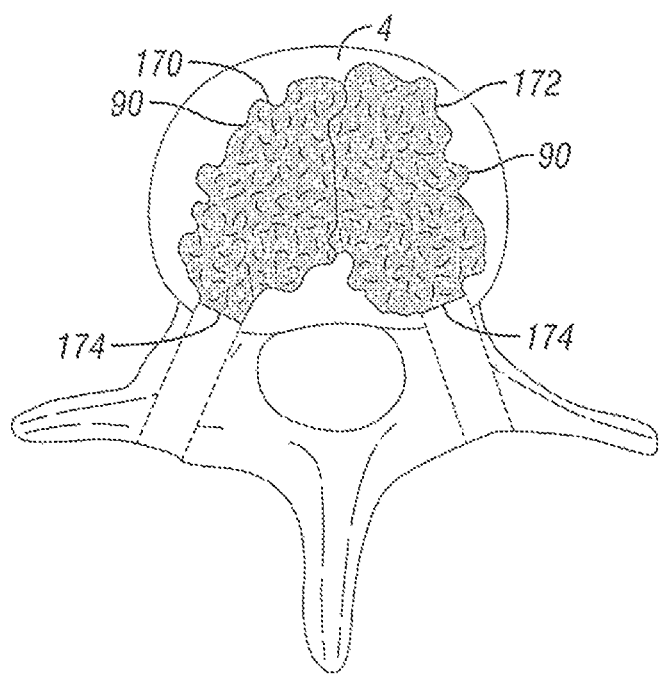

Embodiments may further include detaching the containment jacket 90 in each of the cavities 170, 172 such that the containment jacket 90 containing the filler material 110 remains in each of the cavities 170, 172, as illustrated by FIG. 49. In an embodiment, the containment jackets 90 may be detached in a serial fashion, for example, first in the left cavity 170 and then in the right cavity 172 or, alternatively, first in the right cavity 172 and then in the left cavity. In one embodiment, a cutting device 162 (e.g., FIG. 33) may be used to detach each containment jacket 90 at their respective necks 174.

Figure 50:
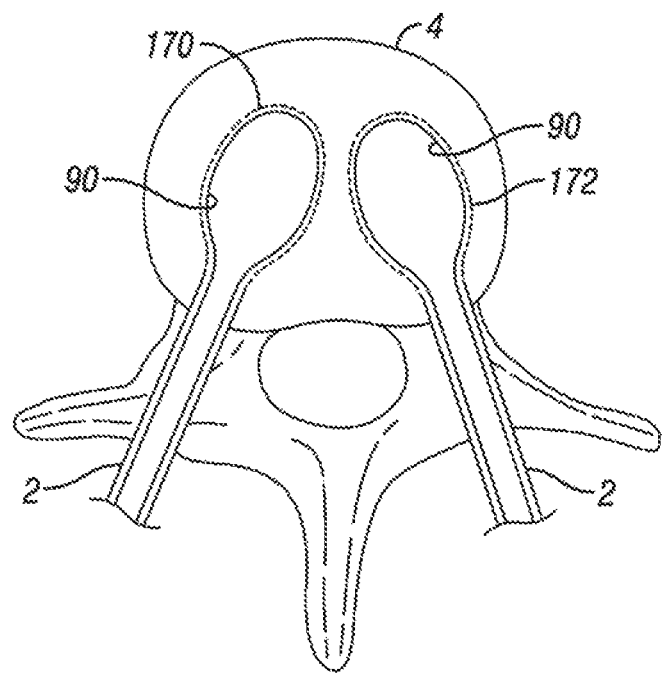
FIGS. 50-53 illustrate a bi-pedicular technique for treating a vertebral fracture in accordance with yet another embodiment of the present invention.

FIGS. 50-53 illustrate another bi-pedicular approach for treating a fracture in vertebral body 4 that employs a containment jacket 90 (e.g., FIG. 13) in accordance with embodiments of the present invention. As illustrated by FIG. 50, embodiments may include creations of cavities 170, 172 in the left and right regions of the vertebral body 4 with a mechanical device 68. In one embodiment, the cavities 170, 172 may be created in a serial fashion, for example, first in the left cavity 170 and then in the right cavity 172 or, alternatively, first in the right cavity 172 and then in the left cavity 170. The cavities 170, 172 may be formed using any of a variety of different techniques, including, for example, using an inflatable balloon 58 (e.g., FIG. 7), a mechanical device 68 (e.g., FIG. 9), or a combination of both. As illustrated, a cannula 2 should extend into each of the cavities 170, 172 providing access to the cavities 170, 172. As further illustrated by FIG. 50, after creation of the cavities 170, 172, a containment jacket 90 may be inserted into each of the cavities 170, 172, in accordance with one embodiment. In one embodiment, the containment jackets 90 may be inserted in a serial fashion, for example, first into the left cavity 170 and then into the right cavity 172.

Figure 51:
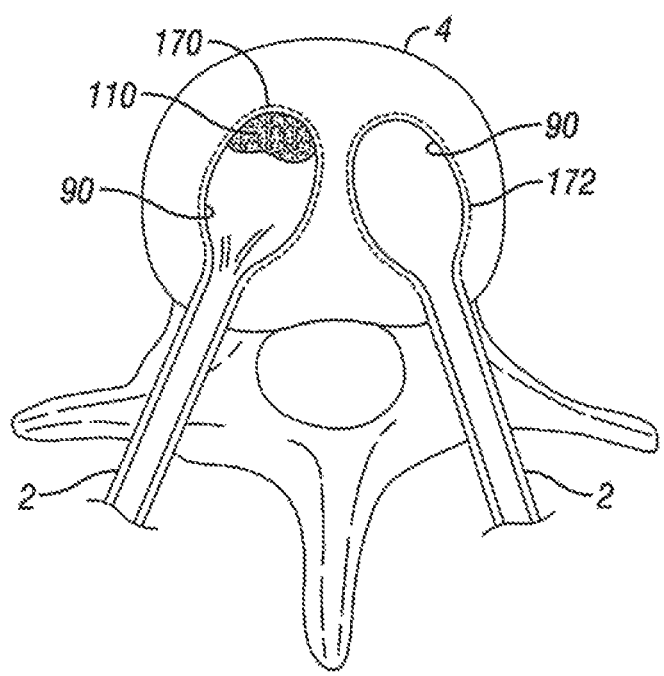
Figure 52:
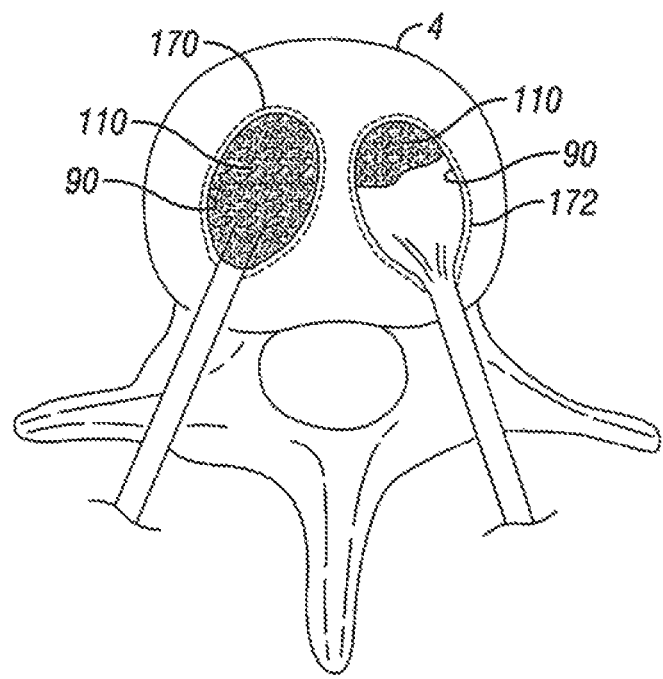

As illustrated by FIG. 51, filler material 110 may then be placed into the containment jacket 90 that is in the left cavity 170. Thereafter, filler material 110 may then be placed into the containment jacket 90 that is in the right cavity 172, as illustrated by FIG. 52. While not illustrated by FIGS. 47 and 48, any of a variety of different devices may be used for introduction of the filler material 110 including the devices illustrated by FIGS. 17-19. While the preceding description describes filling of the containment jacket 90 in left cavity 170 first followed by filling of the containment jacket 90 in the right cavity 172, it should be understood that, in some embodiments, the steps may be reversed with the containment jacket 90 being first filled in the right cavity 172.

Figure 53:
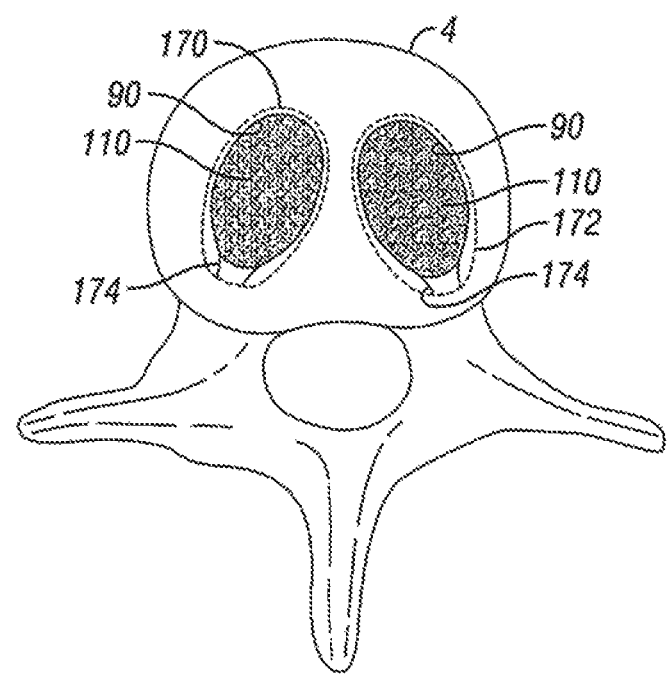

Embodiments may further include detaching the containment jacket 90 in each of the cavities 170, 172 such that the containment jacket 90 containing the filler material 110 remains in each of the cavities 170, 172, as illustrated by FIG. 53. In an embodiment, the containment jackets 90 may be detached in a serial fashion, for example, first in the left cavity 170 and then in the right cavity 172 or, alternatively, first in the right cavity 172 and then in the left cavity. In one embodiment, a cutting device 162 (e.g., FIG. 33) may be used to detach each containment jacket 90 at their respective necks 174.

Constrained Balloon Geometries

As previously discussed, a balloon 58 balloon may be inflated within a vertebral body 4 in accordance with certain embodiments of the present invention, as shown, for example, on FIG. 7. In some embodiments, it may desirable for the inflation of the balloon 58 to be controlled. For example, in some embodiments, the balloon 58 may be configured to have induced asymmetric inflation. In another embodiment, the balloon 58 may be configured such that axial growth may be constrained.

Figure 56:
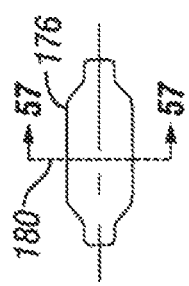
FIGS. 54-59 illustrate a comparison a balloons with symmetric inflation and asymmetric inflation in accordance with embodiments of the present invention.
Figure 59:
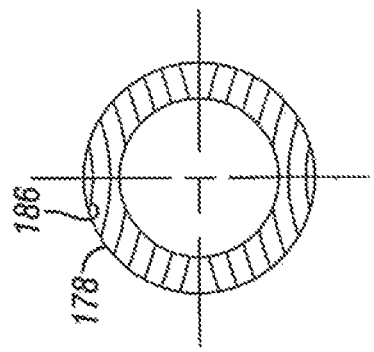
Figure 55:
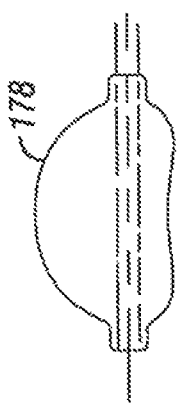
Figure 58:
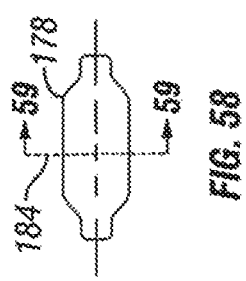
Figure 54:
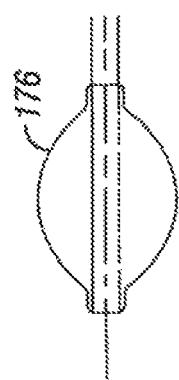
Figure 57:
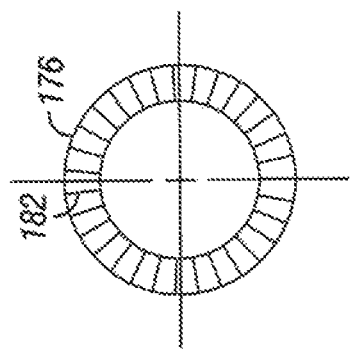

FIGS. 54-55 illustration a comparison of inflation of symmetric balloon 176 with symmetric inflation (e.g., FIG. 54) versus asymmetric balloon 178 with induced asymmetric inflation (e.g., FIG. 55). As illustrated by FIG. 54, the inflation of symmetric balloon 176 without induced asymmetric inflation is symmetrical at the top and bottom. In comparison, the inflation of asymmetric balloon 178 with induced asymmetrical inflation has asymmetric inflation at the top and bottom. FIG. 56 illustrates symmetric balloon 176 in an unstressed/uninflated state. FIG. 57 is a cross-section of symmetric balloon 176 taken along line 180. As illustrated, the symmetric balloon 176 has grain flow 182 that is symmetrical. FIG. 58 illustrates asymmetric balloon 178 in an unstressed/uninflated state. FIG. 59 is a cross-section of asymmetric balloon 178 taken along line 184. As illustrated, the asymmetric balloon 178 has grain flow 186 that is asymmetrical. For example, the grain flow 186 of balloon 178 has been configured to induce asymmetric inflation, as seen in FIG. 55.

Figure 60:
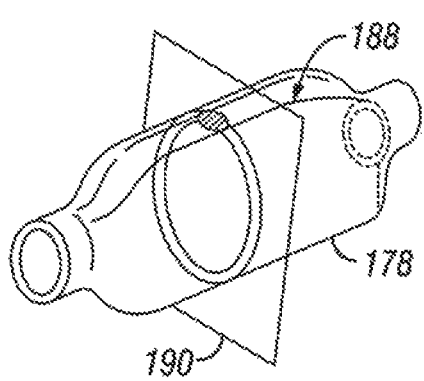
FIGS. 60-64 illustrate a balloon with asymmetric inflation in accordance with one embodiment of the present invention.
Figure 61:
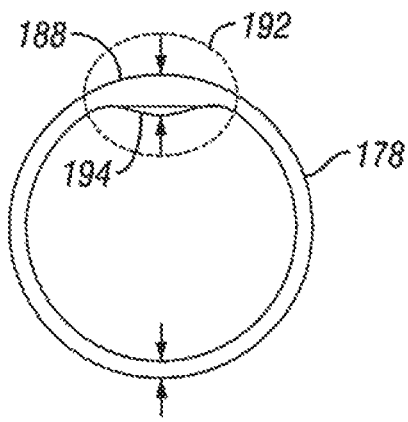
Figure 62:
Figure 63:
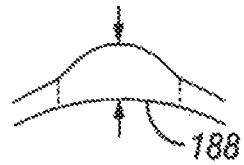
Figure 64:
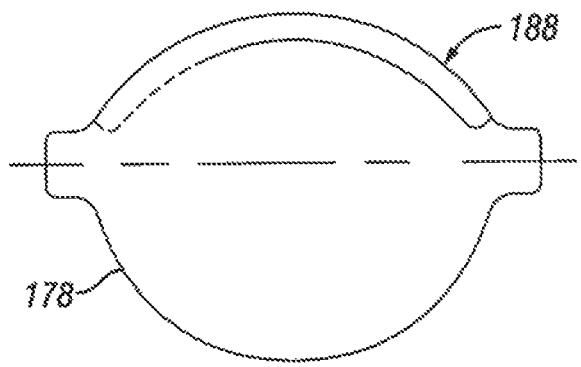

FIGS. 60-64 illustrate an asymmetric balloon 178 with induced asymmetric inflation, in accordance with another embodiment of the present invention. As illustrated by FIG. 60, the asymmetric balloon 178 includes a resistive portion 188. In the illustrated portion, the resistive portion 188 is a longitudinal beam that extends along the longitudinal axis of the balloon 178. For the purposes herein, the resistive portion 188 is more resistive to growth than the remainder of the asymmetric balloon 178. The increased resistivity of the resistive portion 188 may due, for example, to increased balloon thickness or the material used for the resistive portion 188, for example. FIG. 61 is a cross-sectional view of the asymmetric balloon 178 taken along plane 190 of FIG. 60. FIG. 62 is an exploded view taken along circle 192 of FIG. 71. As illustrated by FIGS. 61 and 62, the resistive portion 188 may have increased thickness as compared to the remainder of the balloon 178. In the illustrated embodiment, the increased thickness of the balloon 178 is represented by protruding portion 194, which protrudes from the bottom of the resistive portion 188. FIG. 63 illustrates an alternative embodiment in which the protruding portion 194 protrudes from the top of the resistive portion 188. As illustrated by FIG. 64, the resistive portion 188 constrains of the growth of the asymmetric balloon 178 when inflated resulting in asymmetric inflation.

Figure 65:
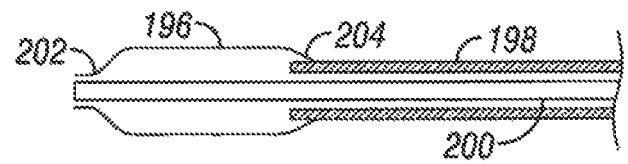
FIGS. 65-66 illustrate an axially constrained balloon in accordance with one embodiment of the present invention.
Figure 66:
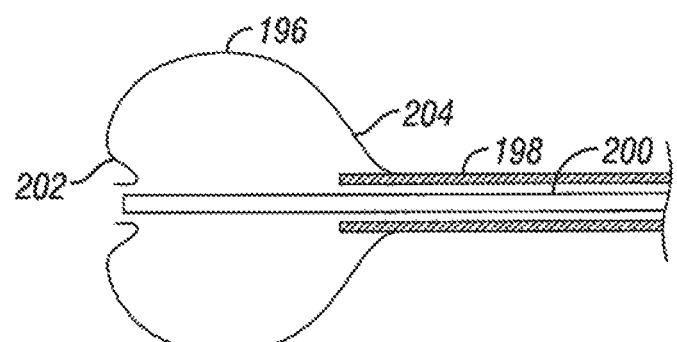
Figure 67:
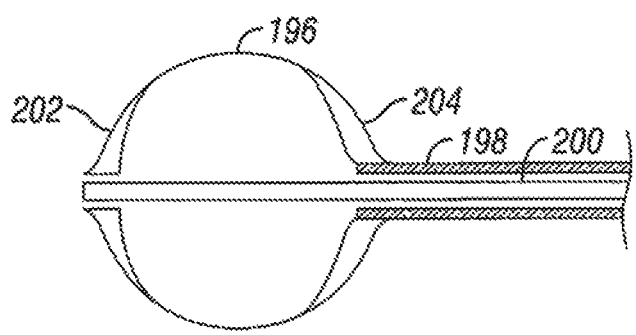
FIG. 67 illustrates an axially constrained balloon in accordance with another embodiment of the present invention.

FIGS. 65 and 66 illustrate an embodiment of an axially constrained balloon 196 in accordance with one embodiment of the present invention. FIG. 65 illustrates the axially constrained balloon 196 in a deflated state. As illustrated, the axially constrained balloon 196 is disposed on a catheter 198 having an inner lumen 200 disposed therein. In the illustrated embodiment, the constrained balloon 196 has a distal end 202 and a proximal end 204. The distal end 202 of the constrained balloon 196 may be attached to the inner lumen 200. In one embodiment, the inner lumen 200 is non-compliant so that expansion at the distal end 202 of the balloon 196 is constrained when the balloon is inflated 196. As illustrated by FIG. 66, the axially constrained balloon 196 expands laterally from the inner lumen 200 while growth of the balloon 196 axially from the inner lumen 200 is constrained. FIG. 67 illustrates an alternate embodiment for constraining the axial growth of the axially constrained balloon 196 when inflated. In the illustrated embodiment, the balloon 196 may have a non-uniform thickness to constrain expansion. As illustrated, the balloon 196 has an increased thickness at the distal end 202 and the proximal end 204, for example, with respect to the remainder of the balloon 196.

Containment Jacket with Dividing Wall

As previously discussed, the balloon 58 that is inserted in the vertebral body 4 may be isolated from the filler material 110 in accordance with embodiments of the present invention. In certain embodiments (FIGS. 24-28), the balloon 58 may be isolated from the filler material 110 with an enclosure 142. In alternative embodiments (FIGS. 29-30), the balloon 58 may be isolated from the filler material 110 with a containment jacket 90 that includes a dividing wall 152. FIGS. 68-72 illustrate one embodiment for constructing the containment jacket 90 with the dividing wall 152. While the following description describes one technique for constructing a containment jacket 90 with a dividing wall 152 it should be understood that other techniques may be used to form a containment jacket 90 with a dividing wall 152 in accordance with embodiments of the present invention. In the illustrated embodiment, the containment jacket 90 with the dividing wall 152 is constructed with film welding. As illustrated, a first layer 206, a second layer 208, a third layer 210, and a fourth layer 212 of material may be provided. The first layer 206 may have an upper face 214 and a lower face (not shown). The second layer 208 may have an upper face 216 and a lower face (not shown). The second layer 208 may also have edges 218. In the illustrated embodiment, the second layer 208 has four edges 218.

Figure 68:
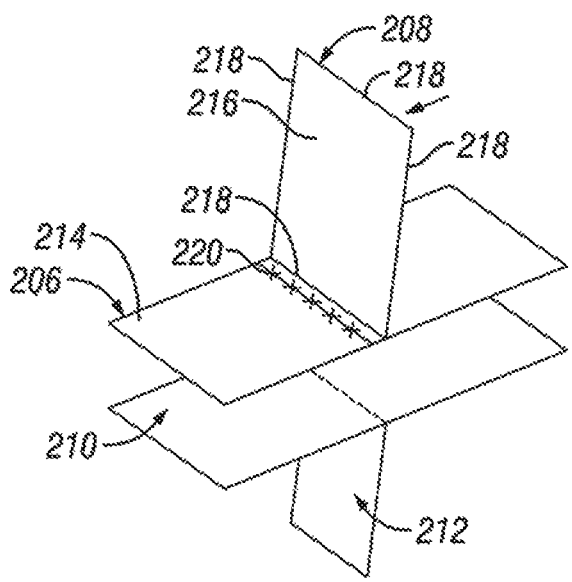
FIGS. 68-72 illustrate techniques for manufacturing a containment jacket with a dividing wall in accordance with one embodiment of the present invention.
Figure 69:
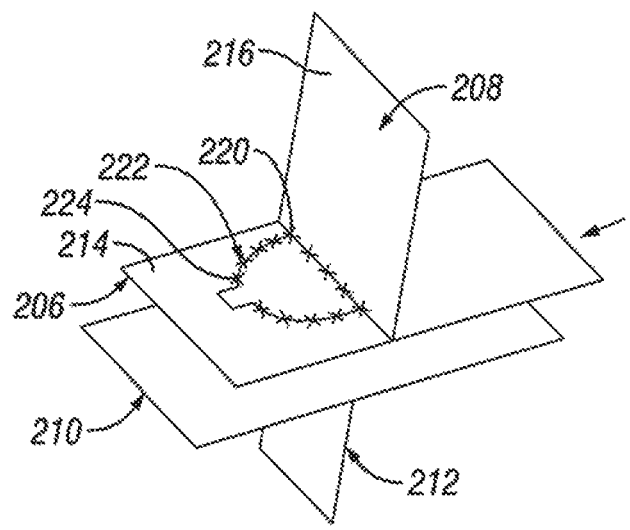
Figure 70:
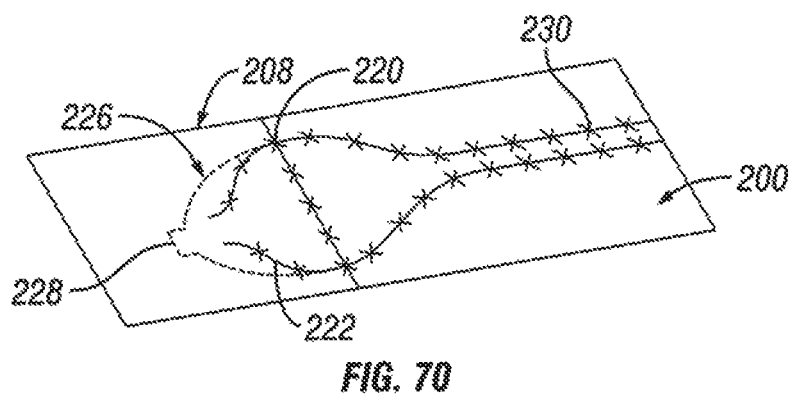

In an embodiment, the first layer 206 and the second layer 208 may be welded together along weld line 214, as best seen in FIG. 68. As illustrated, the weld line 214 may be at one of the edges 218 of the second layer 208 and across the upper face 214 of the first layer 206. While not illustrated, embodiments may include welding the third layer 210 to the fourth layer 212 in a similar manner. As illustrated, the first layer 206 may then be cut along weld/cut line 222 (e.g., FIG. 69) and then welded to the third layer 210. In the illustrated embodiment, the weld/cut line 222 is in the general form of a convex arc that extends from the weld line 220 with a nipple 224 or protrusion at its apex. As illustrated by FIG. 70, the second layer 208 may then be cut along second weld/cut line 226 and then welded to layer 212 (e.g., FIG. 69) at the second weld/cut line 226. In the illustrated embodiment, the second weld/cut line 226 is in the general form of a convex arc that extends from the weld line 222 with a nipple 228 or protrusion at its apex. In an embodiment, the second weld/cut line 226 extends around the weld/cut line 222. As further illustrated by FIG. 70, the first layer 206 may then be cut along third weld/cut line 230 and then welded to the third layer 210 (e.g., FIG. 69) at the third weld cut line 230. In the illustrated embodiment, the third weld/cut line 224 includes two lines, for example, with first portions that converge as they extend away from the weld line 220 and second portions that continue generally parallel as they continue to extend in the same direction. As illustrated, the third weld/cut line 230 extends in the opposite direction of the first and second weld/cut lines 222, 226. While not illustrated, embodiments may include similar welds and cuts to the third and fourth layers 210, 212 that mirror the welds and cuts made to the first and second layers 206, 208.

Figure 71:
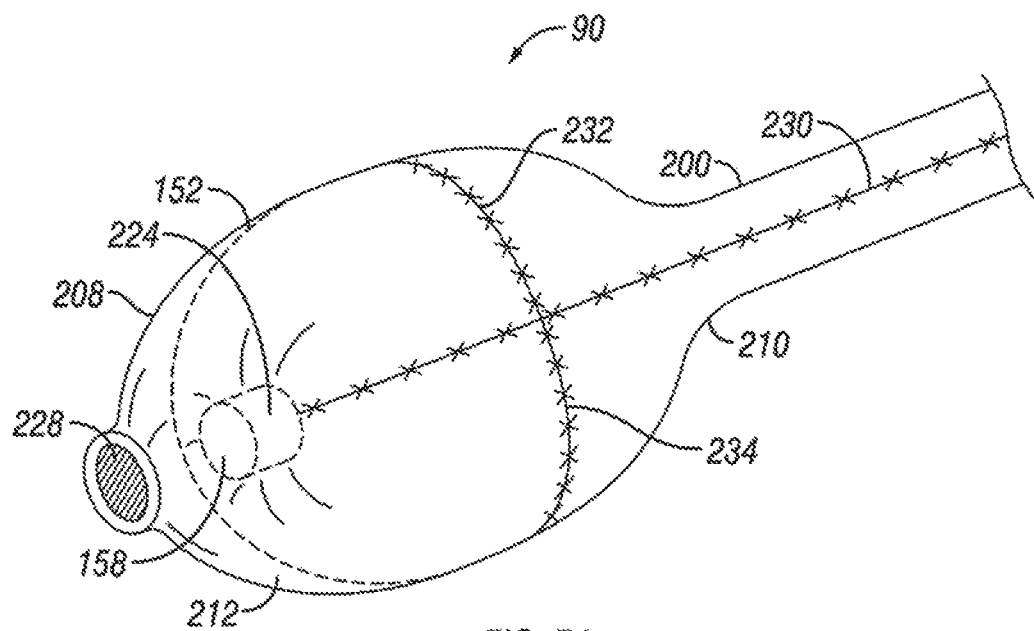
Figure 72:
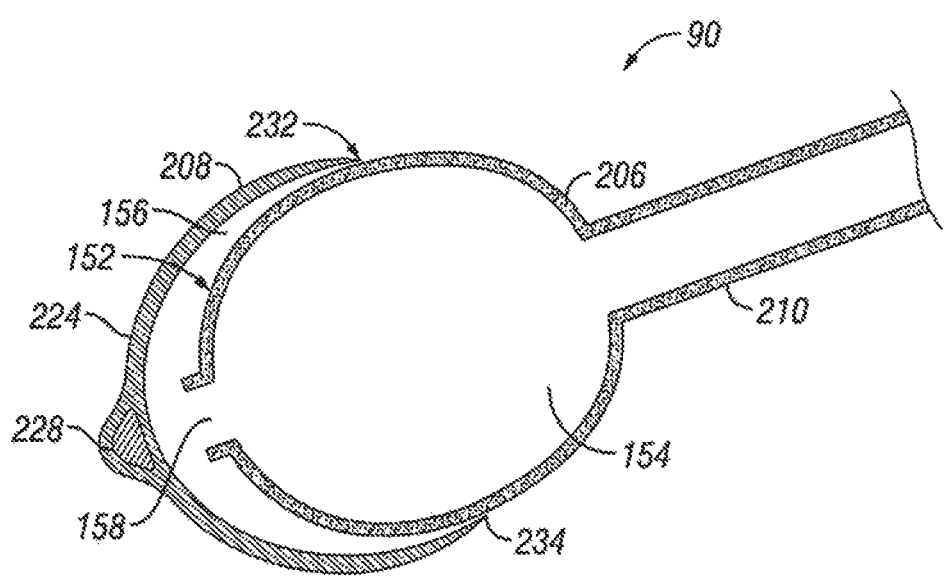

With reference now to FIGS. 71 and 72, a weld may be made at the intersection 232 of the first layer 206 and the second layer 208, and a weld may also be made at the intersection 234 of the third layer 210 and the fourth layer 212. As illustrated, a portion of the first layer 206 and the third layer 210 that extends beyond these welds are disposed within an enclosure created by the second layer 208 and the fourth layer 212. This enclosed portion forms the dividing wall 152 in the containment jacket 90 separating the containment jacket 90 into a proximal region 154 and a distal region 156, as best seen in FIG. 72. As illustrated, the dividing wall 152 may include an opening 158 for providing access to the distal region 156 from the proximal region 158.

Figure 73:
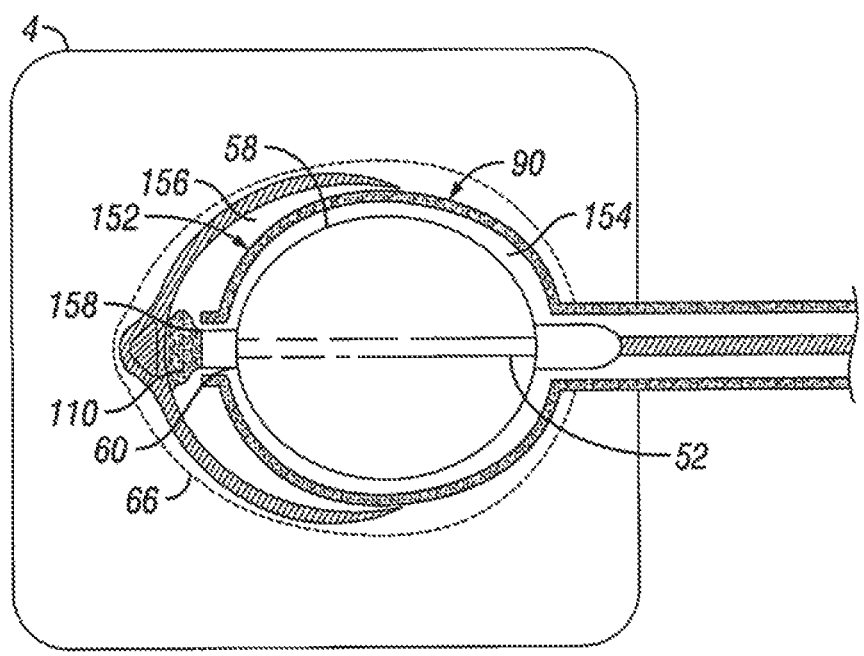
FIGS. 73-75 illustrate a technique for using a balloon with a dividing wall in a vertebral body in accordance with one embodiment of the present invention.
Figure 74:
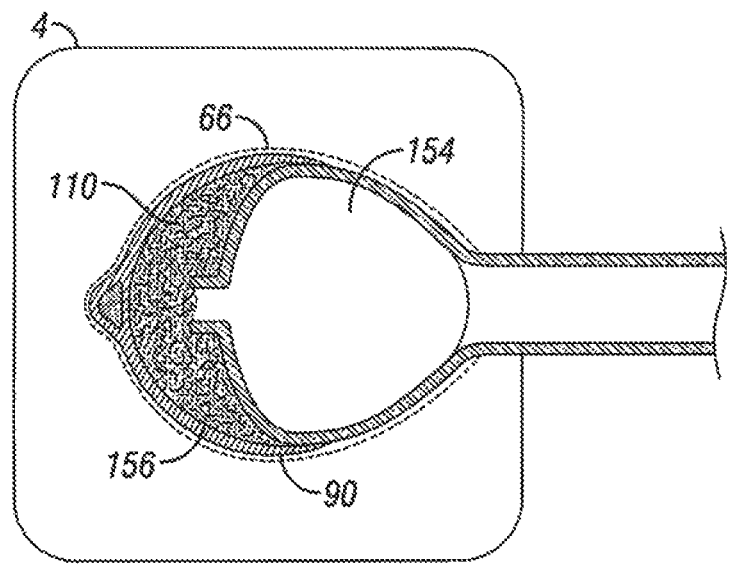
Figure 75:
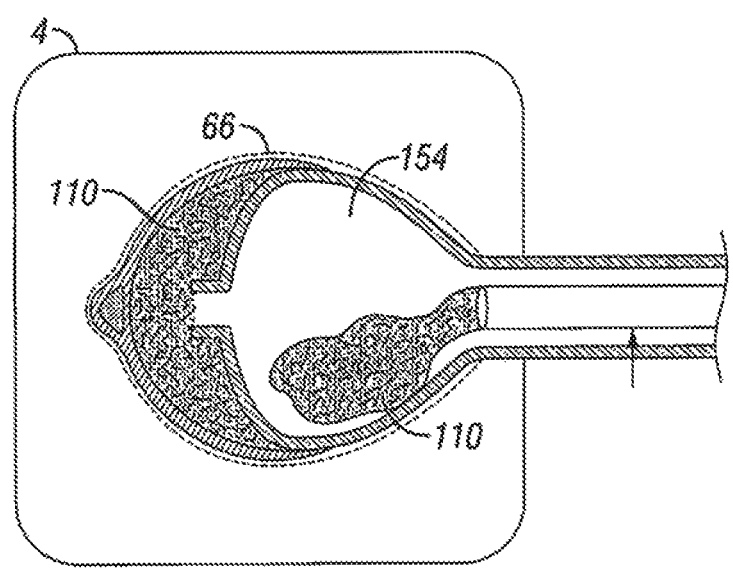

FIGS. 73-75 illustrate a technique for treating a fracture in a vertebral body 4 that employs a containment jacket 90 having a dividing wall 152 in accordance with one embodiment of the present invention. While not illustrated, embodiments may include creation of a cavity 66 in the vertebral body 4 with a mechanical device 68. For example, the cavity 66 may be formed using any of a variety of different techniques, including, for example, using an inflatable balloon 58 (e.g., FIG. 7), a mechanical device 68 (e.g., FIG. 9), or a combination of both. As illustrated by FIG. 73, after creation of the cavity 66 a containment jacket 90 may be inserted into the cavity 66. In the illustrated embodiment, the containment jacket 90 includes a dividing wall 152 that separates the interior of the containment jacket 90 into a proximal region 154 and a distal region 156. As illustrated, the dividing wall 152 includes an opening 158. As further illustrated by FIG. 73, a balloon 58 may be inserted into the proximal region 154 of the containment jacket 90 and inflated. In the illustrated embodiment, an inner lumen 52 is disposed in the balloon that includes an exit port 60 for filler material 110. As illustrated, filler material 110 may then be placed into the distal region 156 with the dividing wall 152 isolating the balloon 58 from the filler material 110. In the illustrated embodiment, the filler material 110 is introduced into the distal region 156 from the exit port 60 of the inner lumen 52. As illustrated, the filler material 110 may be dispensed from the exit port 60 through the opening 158 in the dividing wall 152. The balloon 58 may then be deflated and removed from the proximal region 154, as illustrated by FIG. 74. In one embodiment, the balloon 58 may be deflated and removed after the filler material 110 has been allowed to cure. As illustrated by FIG. 75, filler material 110 may then be introduced into the proximal region 154 that was previously occupied by the balloon 58. While not illustrated by FIGS. 73-75, any of a variety of different devices may be used for introduction of the filler material 110 including the devices illustrated by FIGS. 17-19. The filler material 110 in the proximal region 154 may then be allowed to cure.

Containment Jacket

Alternative Embodiments

Figure 76:
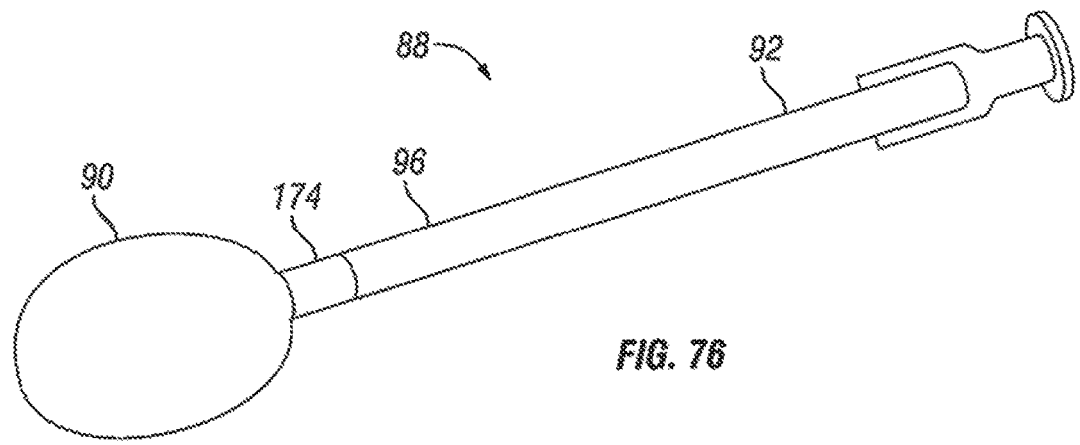
FIGS. 76-82 illustrate techniques for coupling a containment jacket to a tube in accordance with embodiments of the preset invention.
Figure 77:
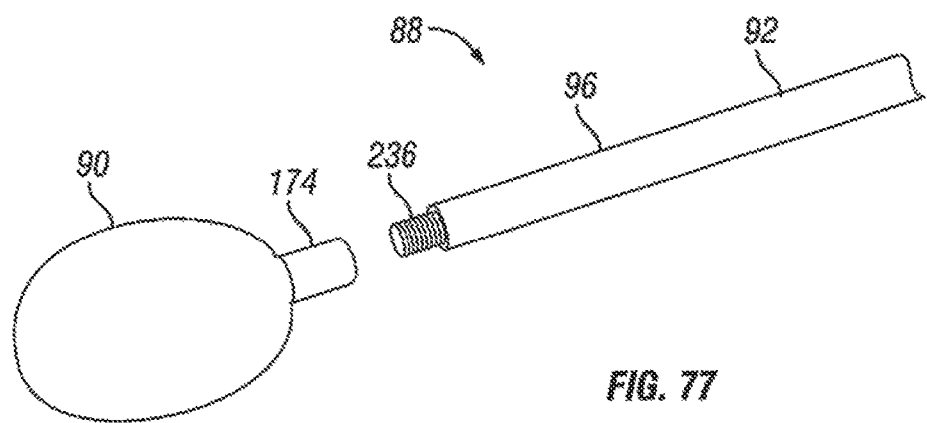

As previously discussed, a containment jacket 90 may be placed into a vertebral body 4 in accordance with embodiments of the present invention, as illustrated, for example, by FIG. 14. As illustrated on FIG. 14, in some embodiments, the containment jacket 90 may be disposed on a tubular member 92. Those of ordinary skill in the art will appreciate that a variety of different techniques may be used in accordance with embodiments of the present technique for attachment of the containment jacket 90 to the tubular member 92. FIGS. 76-77 illustrate an embodiment of the containment assembly 88 that includes containment jacket 90 coupled to a distal end 96 of the tubular member 92. As illustrated, the containment jacket 90 may include a neck 174 placed over the tip 236 of the distal end 96 of the tubular member 92. In an embodiment (not illustrated), an adhesive may be used to couple the neck 174 to the distal end 96. In an alternative embodiment (not illustrated), the neck 174 of the containment jacket 90 may be thermally bonded to the distal end 96 of the tubular member 92. As illustrated by FIG. 77, the tip 236 may be ground to, for example, facilitate flush bonding of the containment jacket 90 with the tubular member 92.

Figure 78:
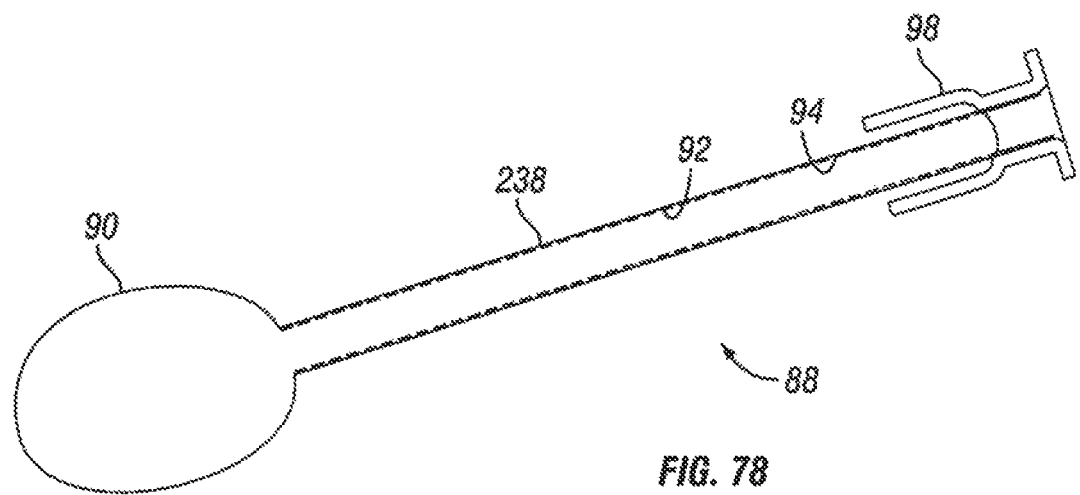
Figure 79:
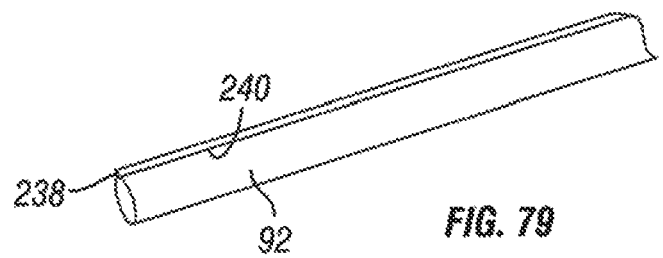
Figure 80:
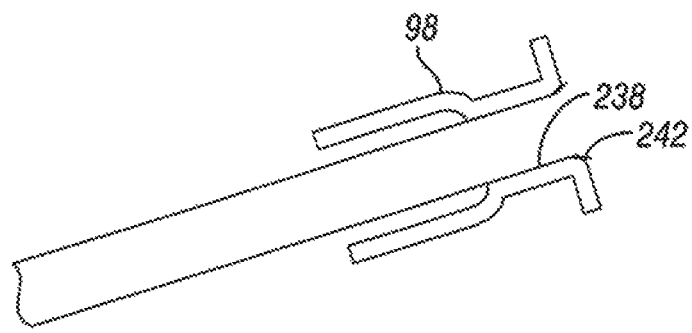

FIGS. 78-80 illustrate another technique for attachment of the containment jacket 90 to the tubular member 92 in accordance with one embodiment of the present invention. As illustrated by FIG. 78, the containment assembly 88 may include containment jacket 90 attached to the tubular member 92. A hub 98 may be disposed on the proximal end 94 of the tubular member 92. In the illustrated embodiment, the containment jacket 90 includes an elongated neck 238. In an embodiment, the elongated neck 238 may be welded to the tubular member 92. Any of a variety of different welding techniques may be suitable, including, for example, radio frequency welding, thermoforming, and ultrasonic welding. As illustrated by FIG. 79, a thin weld line 240 may couple the containment jacket 90 to the tubular member 92. In an embodiment, the containment jacket 90 may be coupled to the hub 98. As illustrated by FIG. 80, the distal end 242 of the elongated neck 472 may be coupled to the hub 98, for example, with an adhesive.

Figure 81:
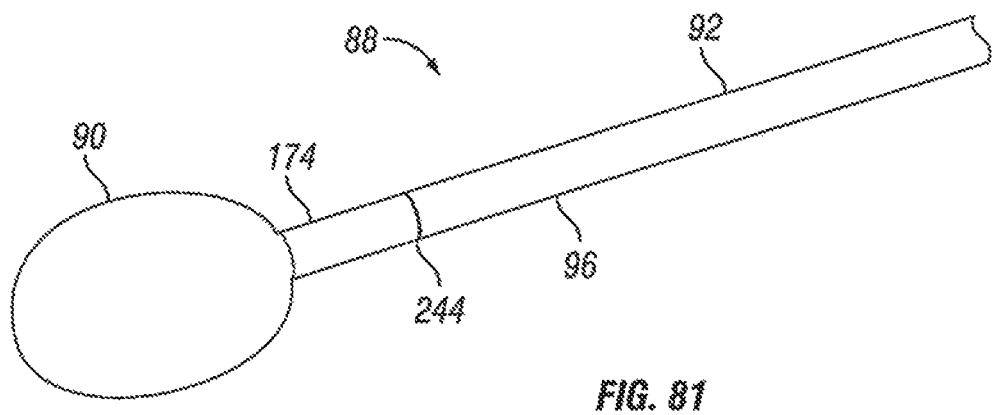

FIG. 81 illustrates yet another technique for attachment of the containment jacket 90 to the tubular member 92 in accordance with one embodiment of the present invention. In the illustrated embodiment, containment assembly 88 includes containment jacket 90 coupled to a distal end 96 of tubular member 92. As illustrated, a butt weld 244 may couple neck 174 of the containment jacket 90 to the distal end 96 of the tubular member 92.

Figure 82:
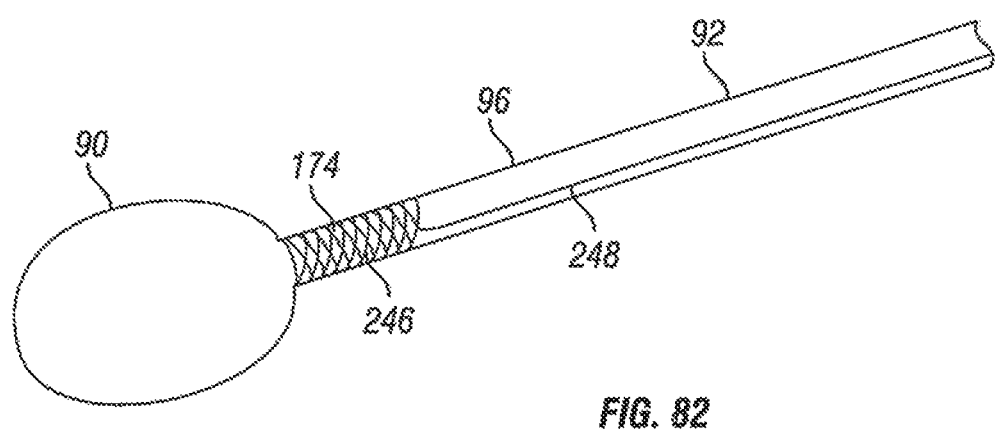

FIG. 82 illustrates yet another technique for attachment of the containment jacket 90 to the tubular member 92 in accordance with one embodiment of the present invention. As illustrated, thread 246 (e.g., suture thread) may be tied over the neck 174 of the containment jacket 90 to secure the containment jacket 90 onto the distal end 96 of the tubular member 92. A cord 248 may extend from the thread 246 that can be pulled to unravel the thread 246 releasing the containment jacket 90 from the tubular member 92.

Figure 83:
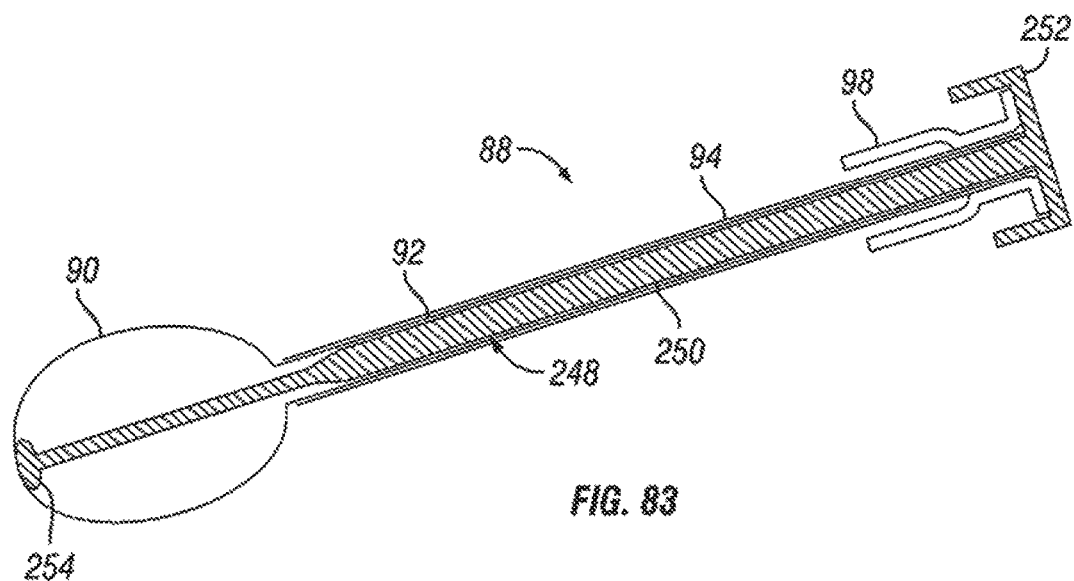
FIGS. 83-84 a containment assembly in accordance with another embodiment of the present invention.
Figure 84:
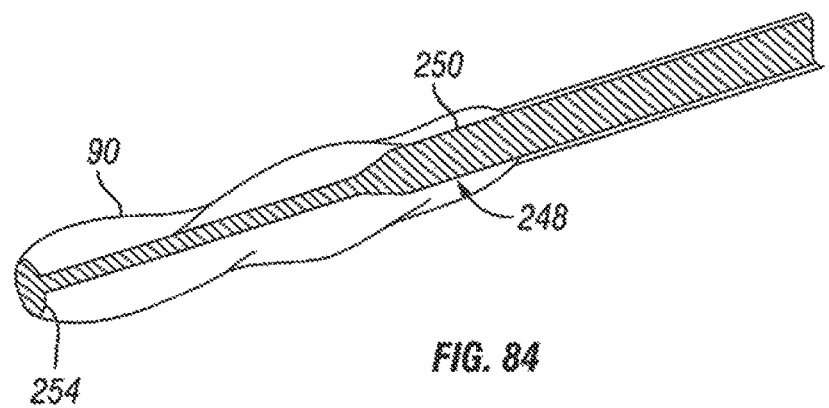

FIGS. 83-84 illustrate an alternate embodiment of the containment assembly 88 that can be used in accordance with one embodiment of the present invention. In the illustrated embodiment, the containment assembly 88 includes a tubular member 92 having a hub 98 on the proximal end 430. As illustrated, a mandrel assembly 248 may be disposed within the tubular member 92. In an embodiment, the mandrel assembly 248 may be constructed from a material that comprises polytetrafluoroethylene. The mandrel assembly 248 may comprise a stem 250 that extends through the tubular member 92. The mandrel assembly 248 may further comprise a mandrel hub 252 engaging the hub 98 of the tubular member 92. The mandrel assembly 248 may further comprise blunt nose 254 opposite the mandrel hub 252. The blunt nose 254 should reduce and/or prevent puncture of the containment jacket 90. The containment jacket 90 may enclose the blunt nose 254 with the elongated neck 238 of the containment jacket 90 extending along the stem 250. As illustrated by FIG. 84, the containment jacket 90 may be wrapped around the stem 250 of the mandrel assembly 248, in one embodiment. The mandrel assembly 248 may, for example, facilitate insertion of the containment jacket 90 through the cannula 2 (e.g., FIG. 1). After the containment jacket 90 has been inserted into the vertebral body 4 (e.g., FIG. 1), the containment jacket 90 may be unwrapped, as illustrated by FIG. 83.

Figure 85:
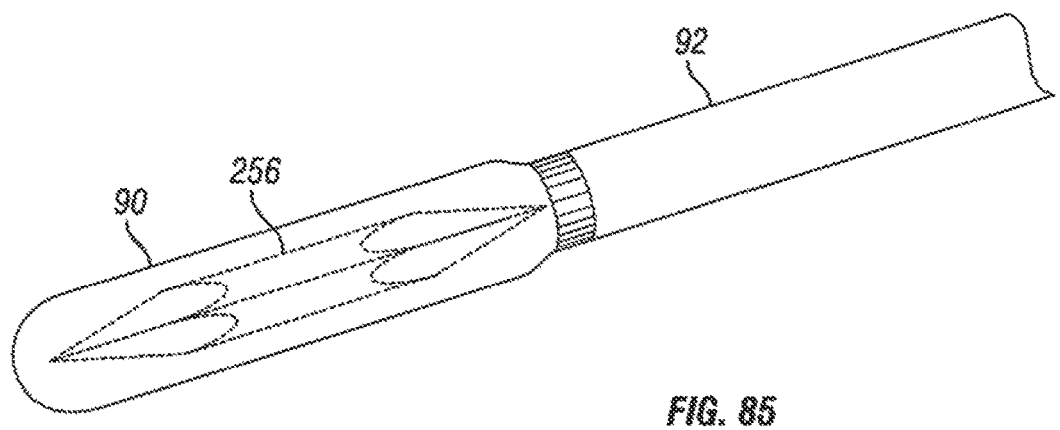
FIGS. 85-86 illustrate a containment jacket in accordance with one embodiment of the present invention.
Figure 86:
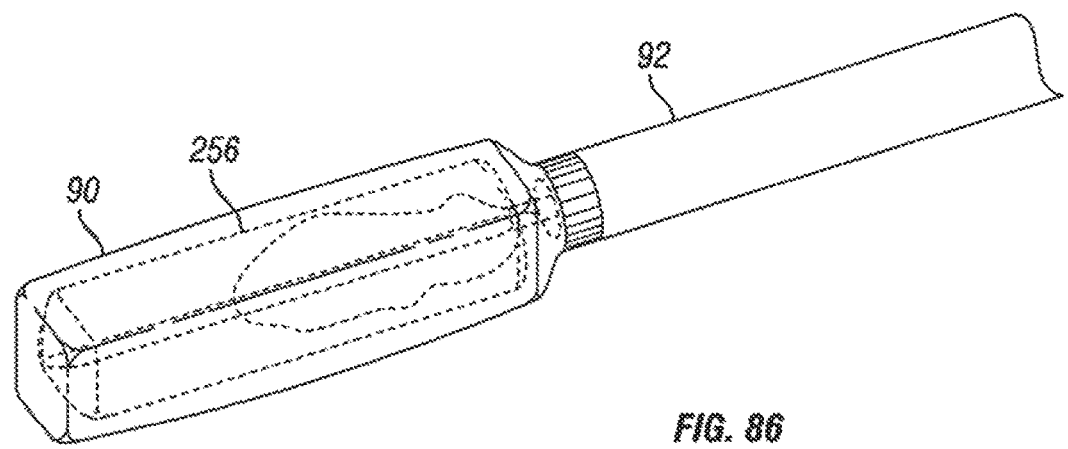

FIGS. 85-86 an embodiment of a containment jacket 90 that may be used in accordance with embodiments of the present invention. As illustrated, the containment jacket 90 may be attached to tubular member 92. In an embodiment, the containment jacket 90 may be configured to a have pre-determined geometrical configuration when in an expanded state. For example, the containment jacket 90 may have a rectangular cross-section in an expanded state, as shown by FIG. 86. In other embodiments, the containment jacket 90 may be generally cylindrical in shape. In certain embodiments, the containment jacket 90 may be inserted into a disc space. Accordingly, embodiments of the containment jacket 90 may have lordosis and/or convexity to match the end plates of a disc space. In alternative embodiments, the containment jacket 90 may be inserted into a vertebral body 4 (e.g., FIG. 1). It should be understood that the containment jacket 90 may also be inserted into other cavities within a bone as desired for a particular application.

In the embodiment illustrated by FIGS. 85-86, frame 256 may be used, for example, to reinforce the containment jacket 90 and provide the desired geometric configuration. As illustrated, the frame 256 may be disposed within the containment jacket 90. FIG. 86 illustrates the frame 256 in a collapsed state. In an embodiment, the frame 256 may have the property of shape memory such that, when the frame 256 is deployed, the containment jacket 90 expands to a predetermined geometrical configured, as illustrated by FIG. 86. The internal frame 256 may be constructed from a material having the property of shape memory. Examples of suitable material include shape memory alloys, such as alloys of nickel and titanium.

Figure 87:
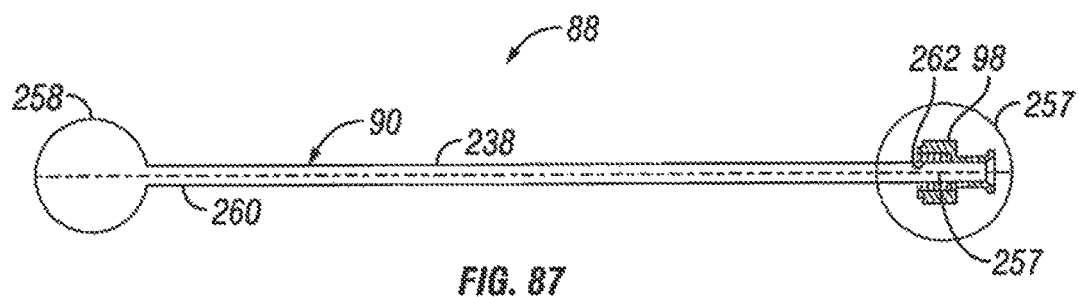
FIGS. 87-88 illustrate a containment assembly in accordance with another embodiment of the present invention.
Figure 88:
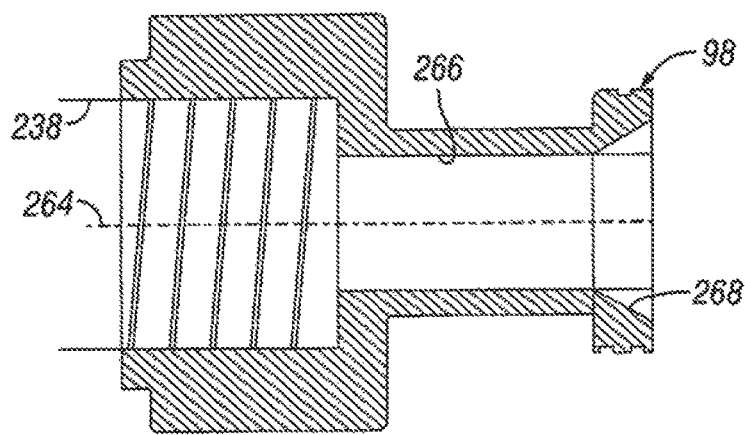

FIGS. 87-88 illustrate a containment assembly 88 in accordance with embodiments of the present invention. FIG. 88 is an exploded view taken along circle 257 of FIG. 87. As illustrated, the containment assembly 88 includes a containment jacket 90 and a hub 98. In the illustrated embodiment, the containment jacket 90 may include an enclosed well 258 having an elongated neck 238 neck extending therefrom. In one embodiment, the ratio of the diameter of the neck 238 to the diameter of the enclosed well 258 is greater than about 1:3, alternatively, greater than about 1:5, and alternatively greater than about 1:7. In the illustrated embodiment, the elongated neck 238 has a distal end 260 connected to the enclosed well 258 and a proximal end 262 connected to the hub 98. While any of a variety of different techniques may be used for connecting the proximal end 262 of the elongated neck 238 to the hub 90, the proximal end 262 and the hub 90 may be adhesively bonded (e.g., Dymax or Loctite UV medical grade), in one embodiment. The containment jacket 90 may have an opening 264 at the proximal end 262. The hub 98 may be configured to allow connection of the containment assembly 88 with other devices that may be used in a medical procedure. In an embodiment, the hub 98 includes a luer lock. As illustrated, the hub 98 may have a through passageway 266 with a tapered throat 268 for allowing easier access of materials/instruments into the containment membrane. While FIG. 87 illustrates the enclosed well 258 of the containment jacket 90 in an expanded state, it should be understood that the enclosed well 258 can be wrapped/folded to enable insertion through a cannula 2 (e.g., FIG. 1) and into a vertebral body 4 (e.g., FIG. 1).

Figure 89:
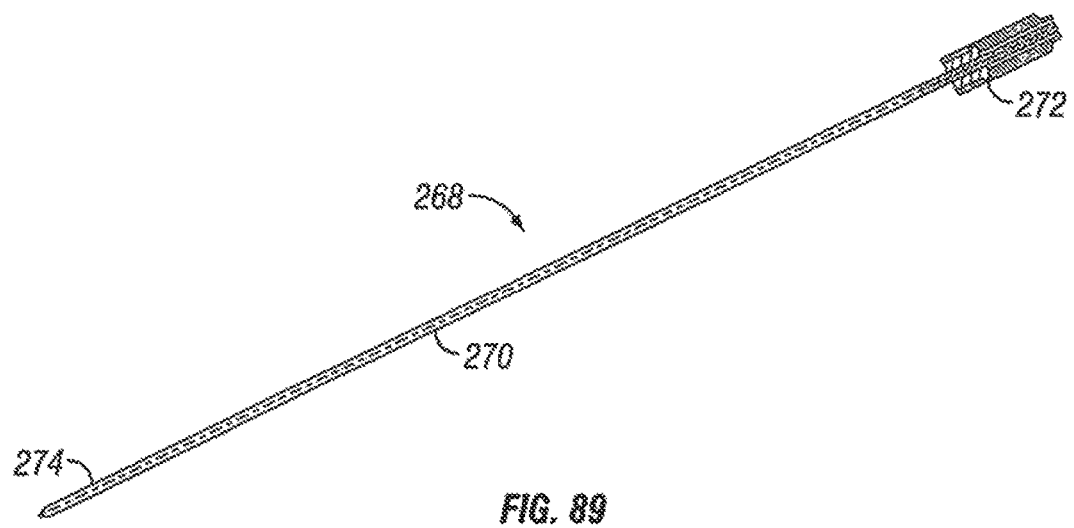
FIG. 89 illustrates an obturator that can be used for insertion of a containment jacket in accordance with one embodiment of the present invention.
Figure 90:
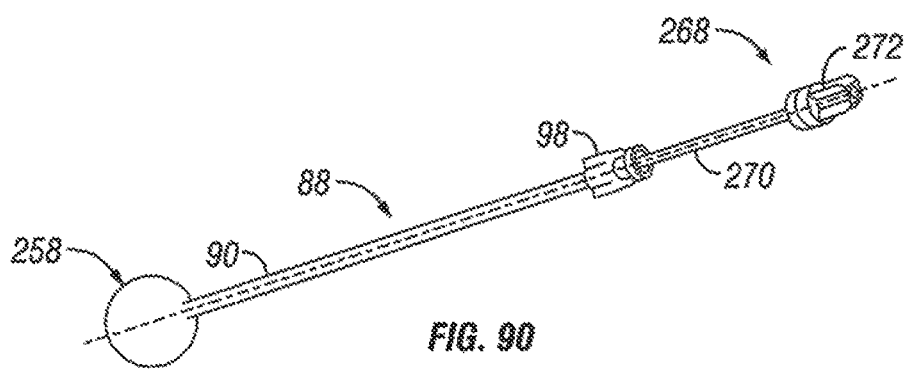
FIG. 90 illustrates insertion of the obturator of FIG. 89 into a containment jacket in accordance with one embodiment of the present invention.

To facilitate insertion of the containment jacket 90 through a cannula 2 (e.g., FIG. 1), any of a variety of suitable devices and techniques may be used. FIGS. 89 and 90 illustrate an obturator device 268 that may be used for insertion of the containment jacket 90 in accordance with embodiments of the present invention. As illustrated, the obturator device 268 may include a stem 270 and an obturator hub 272 at one end of the stem 270. In one embodiment, the obturator hub 272 may be configured to engage the hub 98 of the containment assembly 88. As illustrated, the stem 270 may have a distal end 274. In an embodiment (not illustrated) the enclosed well 258 of the containment jacket 90 may wrap/fold around the distal end 274 of the stem 270 to facilitate insertion of the containment jacket 90 through the cannula 2. In some embodiments, the stem 270 should have sufficient rigidity to push the containment jacket 90 through cannula 2. In some embodiments, the stem 270 may be made from a highly viscous material (e.g., polytetrafluoroethylene, fluorinated ethylene propylene, etc) so that the stem 270 can be inserted through the elongated neck 238 of the containment jacket 90. As best seen on FIG. 90, the stem 270 of the obturator device 268 may be inserted into the containment jacket 90 through the hub 98. The obturator hub 272 may then be attached to the hub 98 of the containment jacket 90.

Containment Jacket—Manufacture Techniques

Those of ordinary skill in the art will appreciate that any of a variety of different techniques may be used to manufacture containment jackets (e.g., containment jacket 90) in accordance with embodiments of the present invention. Examples of suitable techniques dip molding, film welding, and blow molding, among others. Those of ordinary skill in the art will appreciate that dip molding may not be preferred in certain embodiments, such as those in which the neck diameter to well diameter ratio is greater than 1:7. Film welding may be preferred in accordance with embodiments of the present invention. In some embodiments, film extrusion of film welding may be used to provide a film suitable for welding into the shape of a containment jacket 90.

Figure 91:
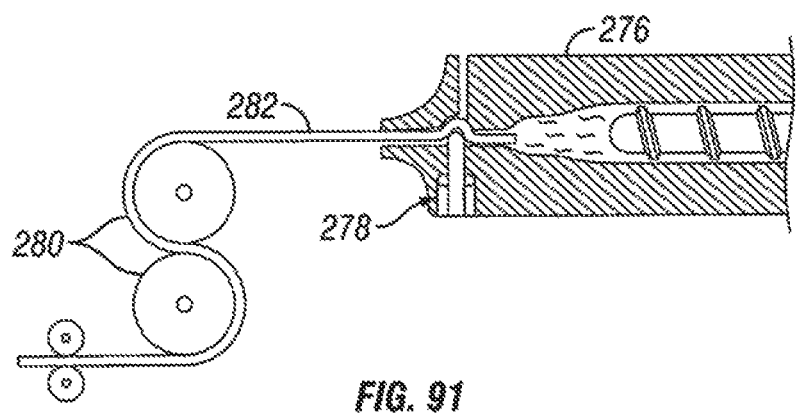
FIGS. 91-95 illustrate various techniques for manufacture of containment jackets in accordance with embodiments of the present invention.
Figure 92:
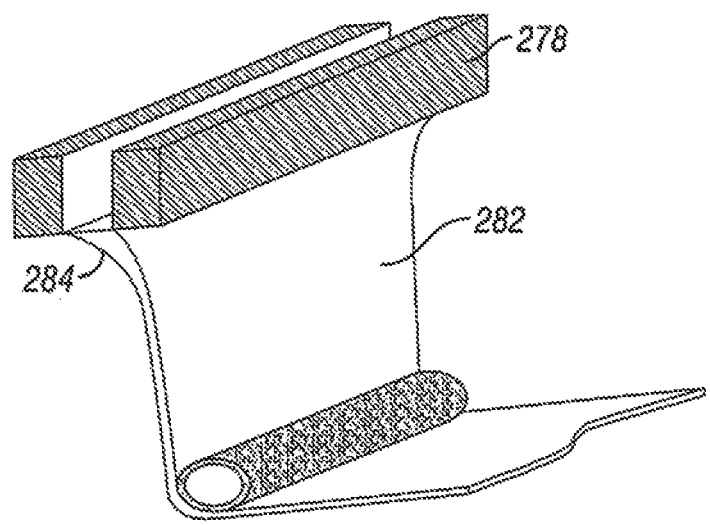

FIG. 91 illustrates an embodiment that uses a film extrusion technique to create film 282. As discussed in more detail below, film welding may then be used to weld the film 282 into the shape of the containment jacket 90. As illustrated, the material (e.g., polymer, additives, etc.) used to create the containment jacket 90 (e.g., FIG. 87) may be melted and conveyed through the extruder 276. The heated material may then be forced through a horizontal slit die 278. Thickness of the film may be controlled as the heated material passes through the die 278. The extruded film exiting the die 278 may be cooled as it passes through the chilled nip rolls 280. Those of ordinary skill in the art will appreciate that the extruded film may be passed onto a carrier material (e.g., polyester film, polyethylene film, paper, etc.) before wrapping around a core. In one embodiment, extrusion temperature may be about 350° F. to about 410° F. FIG. 92 illustrates an alternative embodiment for extrusion of the film commonly referred to as "cast on carrier" in which the extruded film 282 is cast on the carrier material 284 as it exits the die 278.

Figure 93:
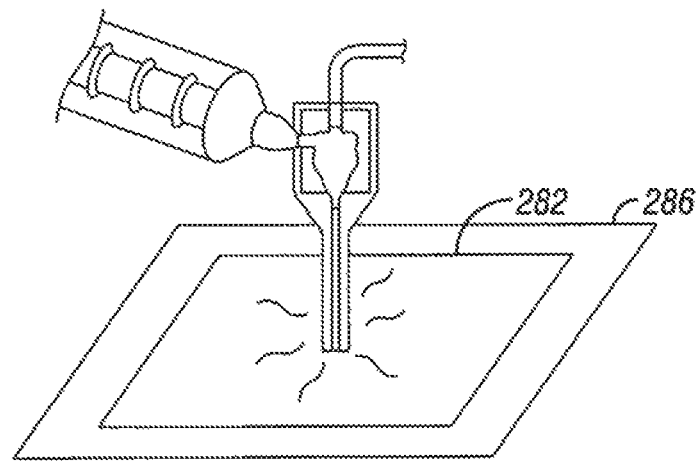

FIG. 93 illustrates an embodiment that uses film casting to create a film 282. As discussed in more detail below, film welding may then be used to weld the film 282 into the shape of the containment jacket 90. In an embodiment, the material used to create the containment jacket (e.g., FIG. 87) may be dissolved in a suitable solvent, such as dimethylformamide or dimethylacetamide. Once dissolved, the solution can be poured onto one or more casting plates 286. Those of ordinary skill in the art will appreciate that the volume of the solution distributed over a specific area of the casting plates 286 will result in a desired film thickness. The solvent may then be allowed to evaporate from the solvent to form the film 286. The film 286 may then be allowed to crystallize, for example, by storing at a temperature of about 86° F. to about 104° F. for several days, which should also reduce the tackiness of the film 286.

In some embodiments, the tackiness of the film 286 may be reduced. In some embodiments, the film tackiness may need to be reduced due to, for example, the soft material (e.g., Bionate® 90A PCU) and/or thin film (e.g., ˜1 mm) that is being used. A number of different techniques may be used to reduce or even potentially eliminate film tackiness. In one embodiment, the rollers and carrier materials used in film extrusion can be roughened to create a matte surface finish on the film 286. The film 286 generally should take on the surface finish of the rollers/carrier, thereby resulting in a matter surface finish, in embodiments where the rollers/carriers are roughened. In one embodiment, the casting plates used in film casting may be roughened (e.g., bead blasted) to have a surface roughness (Ra) of at least 4 micrometers. For the purposes herein, Ra is the arithmetic average of the roughness profile, such as the average of a length of 5 mm. In one embodiment, a surface treatment may be applied to the film 286 to reduce tackiness. For example, a cold gas plasma treatment (e.g., argon, oxygen, hydrogen, nitrogen gas) may be applied to the film 286 to clean its surface while modifying the molecular structure sufficiently with an end resulting in a film 286 with reduced or even no tackiness. In one embodiment, barium sulfate may be added (e.g., less than 30% w/v) to the material (e.g., Bionate® PCU) used to create the containment jacket 90 in either the film extrusion or film casting. It is believed that the barium sulfate should act as a filler producing films with less tackiness. In one embodiment, a Parylene poly(p-xylylene) polymer coating (e.g., —C, —N, —HT) may be applied to the film 286 which deposits a layer of molecules on the surface of the film, resulting in a film 286 with high dry-film lubricity.

Figure 94:
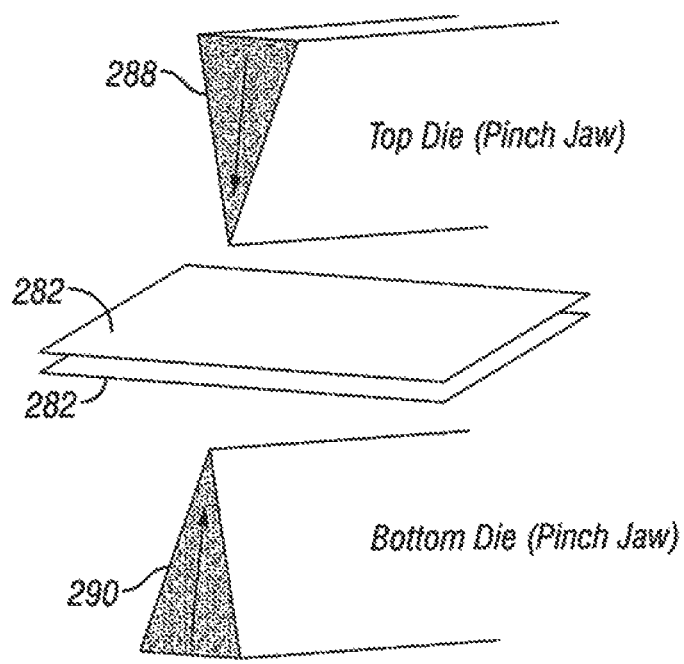

As previously mentioned, film welding may be used in the manufacture of the containment jacket 90 (e.g., FIG. 87) in accordance with embodiments of the present invention. Due to the thin walls of the film (e.g., ˜1 mm), as well as the need to keep the weld lines thin, strong, radiofrequency (RF) weld processing may be used in certain embodiments. Additionally, RF welding processing may be used, in certain embodiments, because materials (e.g., polyurethanes) used for the containment jacket 90 may be poor conductors of electricity. As illustrated by FIG. 94, two films 282 may be layered on top of each other. The upper die 288 and the lower die 290, which act as an electrode, may then be pressed on the films 282 with energy in the form of heat generate at the local joint region under pressure. The upper die 288 and the lower die 290 generally may be in the shape of the final product (e.g., the containment jacket 90). After the energy is stopped, the local melted plastic region cools and re-solidifies resulting in a strong thin weld line.

Figure 95:
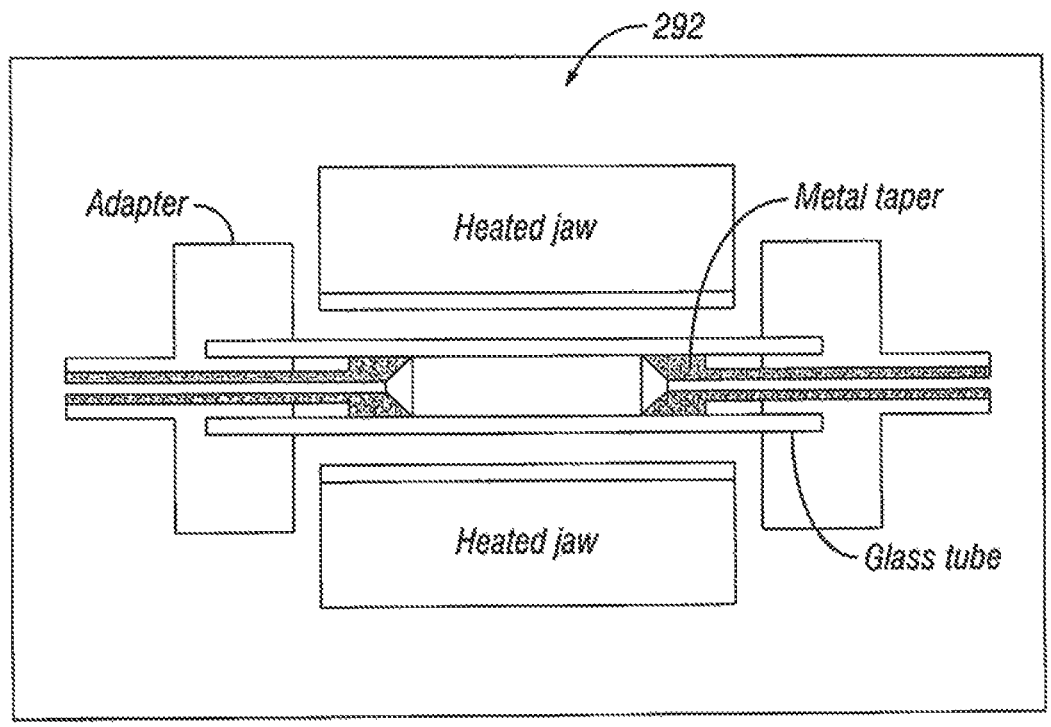

In some embodiments, blow molding may be used in the manufacture of the containment jacket 90 (e.g., FIG. 87). Prior to blow molding, the material (e.g., nylon, PET, polyurethane, etc.) that will be used to construct the containment jacket 90 should first be extruded into a tubing with a specific outside diameter, inside diameter, and length. The tubing may then be inserted into a specific-shaped cavity in a blow molding machine and air is blown into the mold to form the desired shape of the mold using a combination of heat and pressure, for example. An example of a blow molding machine that may be used in one embodiment of the present invention is illustrated by reference number 292 on FIG. 95.

Radiopaque Markers

Figure 96:
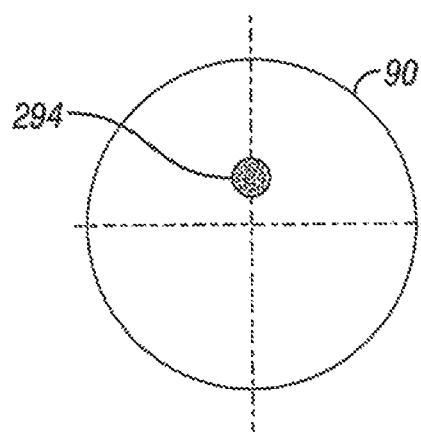
FIG. 96 illustrates a containment jacket with a radiopaque marker in accordance with one embodiment of the present invention.

In some embodiments, radiopaque markers may be used so that the instruments, such as catheter 2 (e.g., FIG. 1), balloon 58 (e.g., FIG. 7), and containment jacket 90 (e.g., FIG. 87), can be visualized using an imaging technique. The radiopaque markers may be used, for example, to ensure the desired placement of the instrument. The radiopaque marker may be checked on the generated image to verify instrument location. In an embodiment, the imaging technique may include fluoroscopy, including both lateral and AP fluoroscopy. In some embodiments, radiopaque markers can be incorporated into the instruments. For example, one or more radiopaque markers may be incorporated into a distal end of the instruments. In one embodiment, one or more radiopaque markers may be incorporated into a distal end of the balloon assembly 50. As illustrated by FIG. 96, embodiments may include incorporation of one or more radiopaque markers 294 into the containment jacket 90.

Those of ordinary skill in the art will appreciate that the radiopaque markers 294 may be in a variety of different shapes (e.g., lines, dots, etc.). A non-limiting example of a suitable radiopaque marker is radiopaque medical ink printing wherein tungsten or other high radiopaque metals loaded in medical grade ink can be printed onto the surface of the containment jacket 90. Another non-limiting example of a suitable radiopaque marker is a piece metal/marker band (e.g., tantalum, platinum/iridium, etc.) that may be bonded to a surface of the instrument. Bonding of the band can be achieved, for example, via a medical grade adhesive (e.g., Dymax or Loctite UV curable medical grade), a drop of a polyurethane (e.g., Bionate® PCU) in dimethylformamide or dimethylacetamide solution, or a drop of molten polyurethane (e.g., Bionate® PCU).

Cement Leakage

Figure 97:
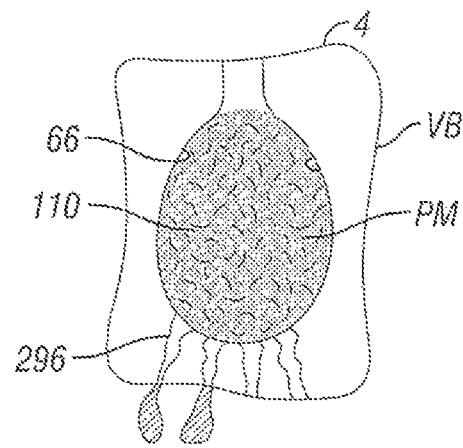
FIGS. 97-98 illustrate techniques for use of bone dust in a vertebral body in accordance with one embodiment of the present invention.
Figure 98:
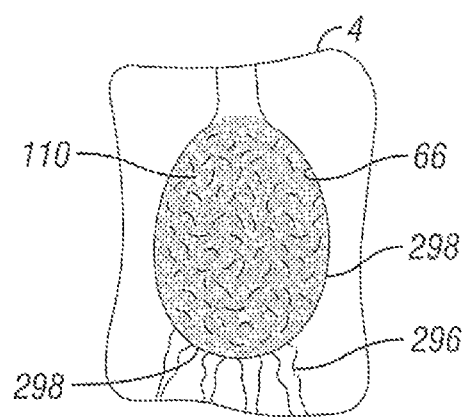

In some embodiments, the filler material 110 may be introduced into the vertebral body 4 without containment in a containment jacket 90. For example, FIGS. 35-38 (described above) disclose introduction of the filler material 110 into the vertebral body 4 without containment. By way of further example, FIGS. 39-42 (described above) also disclose the introduction of the filler material 110 into the vertebral body 4 without containment. However, when filler material 110 is introduced into a cavity 66 in the vertebral body 4 without containment, the filler material 110 can leak through cracks 296 in the vertebral body 4, as illustrated by FIG. 97. To prevent leakage through cracks 296, the cracks 296 may be packed with bone particles 298 (e.g., bone dust, bone morcels), as illustrated by FIG. 98. It is believed that the bone particles 298 in the cracks 296 should provide increased surface tension thereby preventing the filler material 110 from leaking out the cracks 296. While packing bone particles 298 into the cracks 296 may be suitable for treating a variety of different fractures in a vertebral body 4, embodiments of the present technique may be particularly suitable for the treatment of acute fractures in a vertebral body.

Filler Material

The preceding description describes the use of a filler material 110 in accordance with embodiments of the present invention. Those of ordinary skill in the art will appreciate that the filler material 110 may comprise any of a variety of materials that may be utilized to, for example, fill and stabilize the cavity 66 in the vertebral body 4 (e.g., FIG. 8). Examples of suitable materials may include bone cements (e.g. polymethyl methacrylate), human bone graft and synthetic derived bone substitutes.

Additional Treatments

In addition, the preceding description is directed, for example, to treatment of vertebral fractures that includes a containment assembly 88 (e.g., FIG. 13) for cement containment and/or a balloon 58 (e.g., FIG. 37) for maintaining vertebral height. It should be understood that the present technique also may be used in other suitable bone treatments were maintenance of vertebral height and/or cement containment may be desired. By way of example, embodiments of the present invention may be used to treat tibia plateau fractures, distal radius fractures, and cancellous fractures.

Containment Jacket—Double Chamber

Referring again to FIGS. 71-75, a dividing wall 152 may separate the containment jacket 90 into a proximal region 154 (i.e., a proximal chamber) and a distal region 156 (i.e., a distal chamber). As mentioned, the dividing wall 152 of the double-chamber containment jacket 90 may include an opening 158 for providing access to the distal region 156 from the proximal region 158. As further discussed, the containment jacket 90 may be inserted into the created cavity 66, a balloon 58 inserted into the proximal region 154 of the containment jacket 90, and the balloon 58 inflated. Filler material 110 may be introduced into the distal region 156 through the opening 158 in the dividing wall 152 from the exit port 60 of the inner lumen 52 disposed inside the balloon 58. The balloon 58 may then be deflated and removed from the proximal region 154, before or after the filler material 110 in the distal region has been allowed to cure. Filler material 110 may then be introduced into the proximal region 154 previously occupied by the balloon 58, and allowed to cure.

Figure 99:
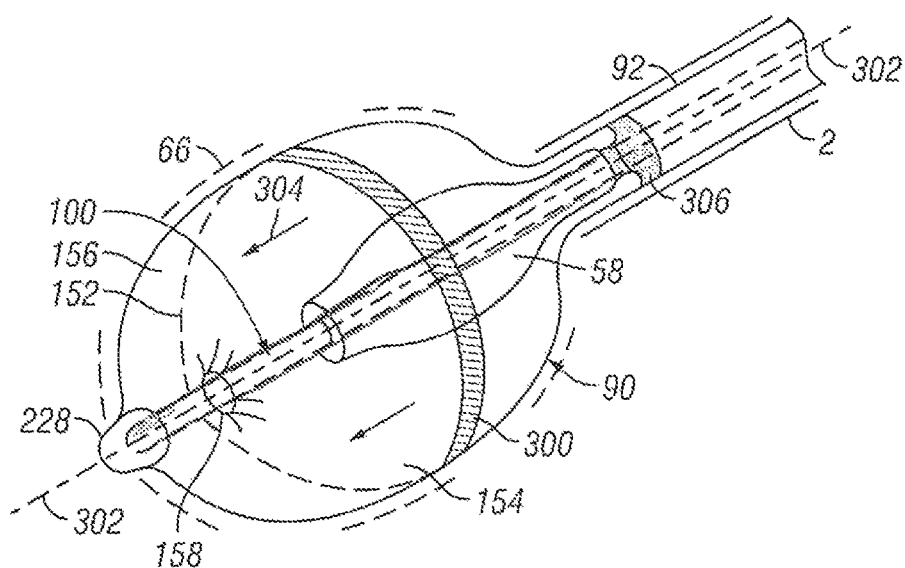
FIGS. 99-100 illustrate an exemplary double-chamber containment jacket 90 in accordance with one embodiment of the present invention.
Figure 100:
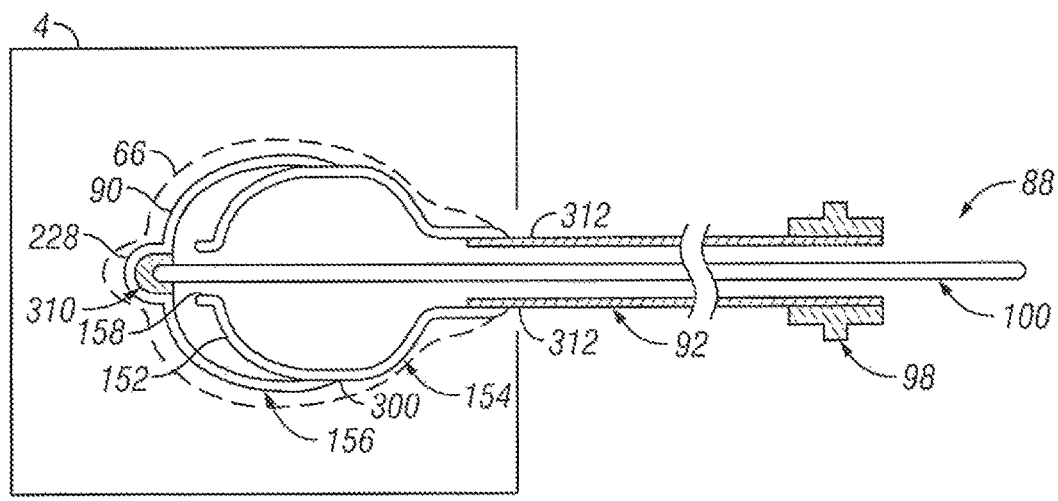

FIGS. 99-100 illustrate an exemplary double-chamber containment jacket 90. FIG. 99 shows the proximal region 154 (i.e., proximal chamber) and a distal region 156 (i.e., distal chamber) separated by the dividing wall 152. In construction of the containment jacket 90, a weld zone 300 may encompass the intersections 232 and 234 shown in FIGS. 71-72. Moreover, the containment jacket 90 may be coupled to the distal end of a tubular member 92, such as via additional welding, i.e., welding of the third layer 210 and/or fourth layer 212 (see FIGS. 68-72) to tubular member 92.

In treatment, a directing device such as a mandrel or guide wire 100, shown straddling reference center line 302 in the illustrated embodiment of FIG. 99, may be situated in the tubular member 92 and used to place the containment jacket 90 through a cannula 2 into the previously created cavity 66 (partially illustrated). In certain embodiments, the guide wire 100 (e.g., a K-wire) may extend through an opening 158 of the dividing wall 152. The distal end of the guide wire 100 may dock in a nipple 228 of the containment jacket 90, for example.

Further, as discussed in previous embodiments, an inflatable bone tamp or balloon 58 may be inserted into the containment jacket 90. The balloon 58 disposed around an inner lumen 52 (not shown) of a catheter or bone tamp, for example, may be inserted through the tubular member 92 over (around) the guide wire 100. In FIG. 99, the balloon 58 is depicted as being inserted into the proximal region 154, with directional movement of the balloon 58 indicated by arrows 304. The distal end of the balloon 58 including an inner lumen 52 (not illustrated) within the balloon 58 may ultimately rest at the opening 158 of the dividing wall 152. Of course, in certain embodiments, while the balloon 58 may generally reside in the proximal region 154, the inner lumen 52 (not illustrated) may extend through the opening 158 into the distal region 156.

FIG. 100 illustrates a cross-section of a containment assembly 88 having the double-chamber containment jacket 90 and tubular member 92 of FIG. 99, but without the inserted balloon 58 which is omitted for clarity. The containment assembly 88 may include a hub 98 (and a luer fitting 138 not shown) at the proximal end of the tubular member 92 for receiving a balloon assembly 58 (not illustrated), for example. Again, in contrast to FIG. 99, a balloon 58 is not inserted into the containment jacket 90.

In FIG. 100, the guide wire 100 is inserted into the tubular member 92 to guide the containment jacket 90 through the cannula 2 (FIG. 99) into the cavity 66 (FIG. 99). In this example, the distal end of the guide wire 100 rests in a docking tip 310 of the nipple 228 of the containment jacket 90. The docking tip 310 may be polycarbonate-urethane (PCU), for example, or other material. Further, the containment jacket 90 may be a PCU film, for example, or other material. As indicate above, all or portions of the containment jacket 90 may be coated with a coating material, such as polyxylylene or poly para-xylene polymer, i.e., a Parylene (e.g., Paraylene C). Of course, the containment jacket 90 may instead be coated with other coating materials, such materials generally biocompatible, and optionally providing for low friction and/or chemical resistance, for instance. Moreover, in addition to the weld zone 300, the containment jacket 90 may also have a weld zone 312, for example, where layer(s) of the containment jacket 90 intersect or meet the tubular member 92, such as at intersections 232 and 234 (see FIGS. 71-72) previously mentioned.

Figure 101:
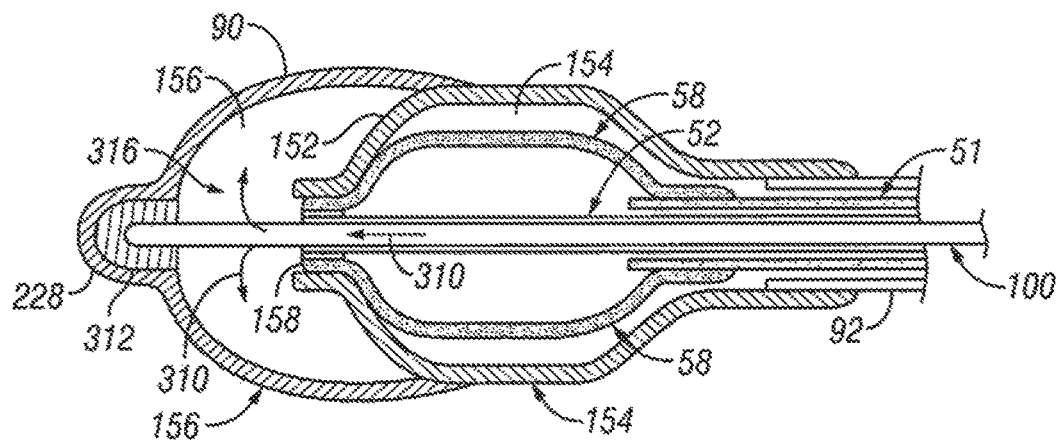
FIG. 101 illustrates the double-chamber containment jacket 90 of FIGS. 99-100 having a distal tip in accordance with one embodiment of the present invention.
Figure 102:
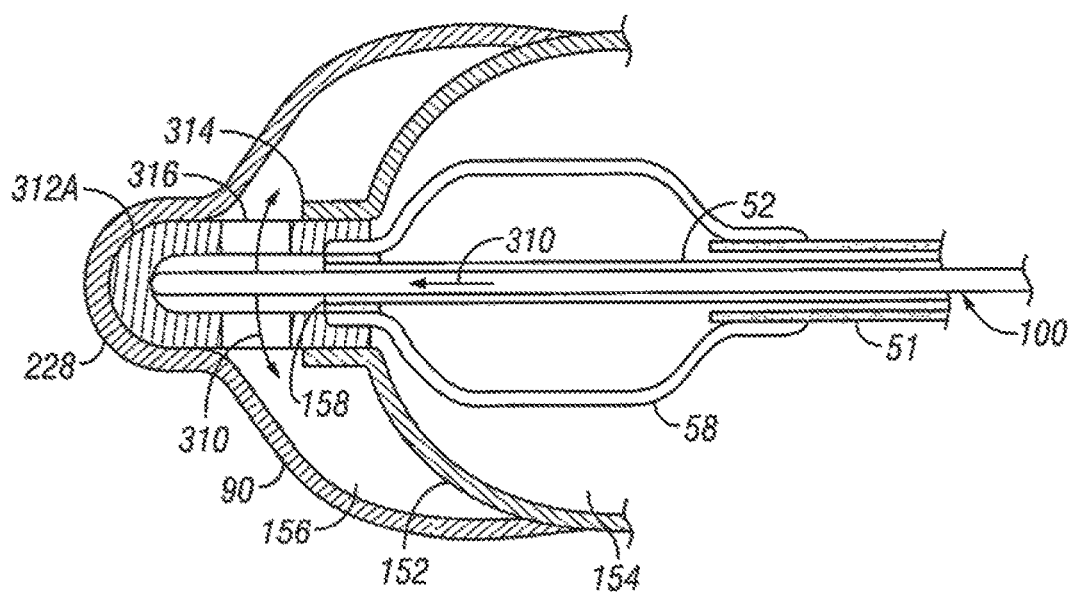
FIG. 102 illustrates the double-chamber containment jacket 90 of FIGS. 99-100 having an alternate distal tip in accordance with another embodiment of the present invention.

FIGS. 101 and 102 illustrate a double-chamber containment jacket 90. FIG. 101 illustrates the containment jacket 90 disposed at the distal end of a tubular member 92. For clarity, FIG. 102 illustrates the containment jacket 90 without the tubular member 92. Further, as discussed below, FIG. 102 depicts the containment jacket 90 having an alternative distal docking tip 312A. As mentioned, in treatment, the containment jacket 90 may be inserted through an access cannula 2 (not illustrated) into a pre-created cavity 66 (not illustrated) of a vertebral bone 4. A guide wire 100 or other guiding device may place the containment jacket 90 into the cavity 66.

A balloon 58 (i.e., inflatable bone tamp) is inserted through the tubular member 92 into the proximal region 154 of the containment jacket 90. In one example, the balloon 58 is slid over the guide wire 100 inside the tubular member 92.

The balloon 58 is attached to the distal end of an outer tubular member or catheter 51 which surrounds an inner bore or inner lumen 52, for example. In one example, the catheter 51 (or inflatable bone tamp) and inner lumen 52 are slid over the guide wire 100 [see FIG. 103 (2)] to place the balloon into the containment jacket 90. The discharge of the inner lumen 52 may reside at the opening 158 or extend through the opening 158.

In alternate embodiments, the guide wire 100 is removed from the tubular member 92 and placed inside the inner lumen 52 to guide and position placement of the balloon 58 into the containment jacket 90. In yet another alternate embodiment, the guide wire 100 guides an assemblage of the containment jacket 90 and balloon 58 into the cavity 66.

As indicated, the guide wire 100 may dock in the docking tip 312 (FIG. 101) or in an alternate docking tip 312A (FIG. 102), at the nipple 228 of the containment jacket 90. The alternate docking tip 312A (FIG. 102) includes an extension 314 as an internal support in the containment jacket 90. For example, the extension 314 may reduce the occurrence of the distal chamber 156 of the containment jacket 90 collapsing on and clinging to the dividing wall 152.

In the illustrated embodiment of FIG. 102, the extension 314 includes a flow path 316 for filler material (e.g., bone cement) to discharge from the inner lumen 52 into the distal chamber 156. Indeed, in the embodiments illustrated respectively in both FIGS. 1 and 2, the guide wire 100 may be removed from the inner lumen 52, and bone cement (e.g., liquid bone cement) injected into the containment jacket 90 via the inner lumen 52, as noted by flow arrows 310. The discharge of the inner lumen 52 is depicted as positioned at the opening 158 in FIGS. 101-102, but also may be routed through the opening 158 into the distal region 156. Lastly, it should be noted that the containment jacket 90 may be evacuated of air and moisture via the tubular member 92 or catheter 51. Further, an inflation medium may be injected into the balloon 58 using the catheter 51.

Figure 103:
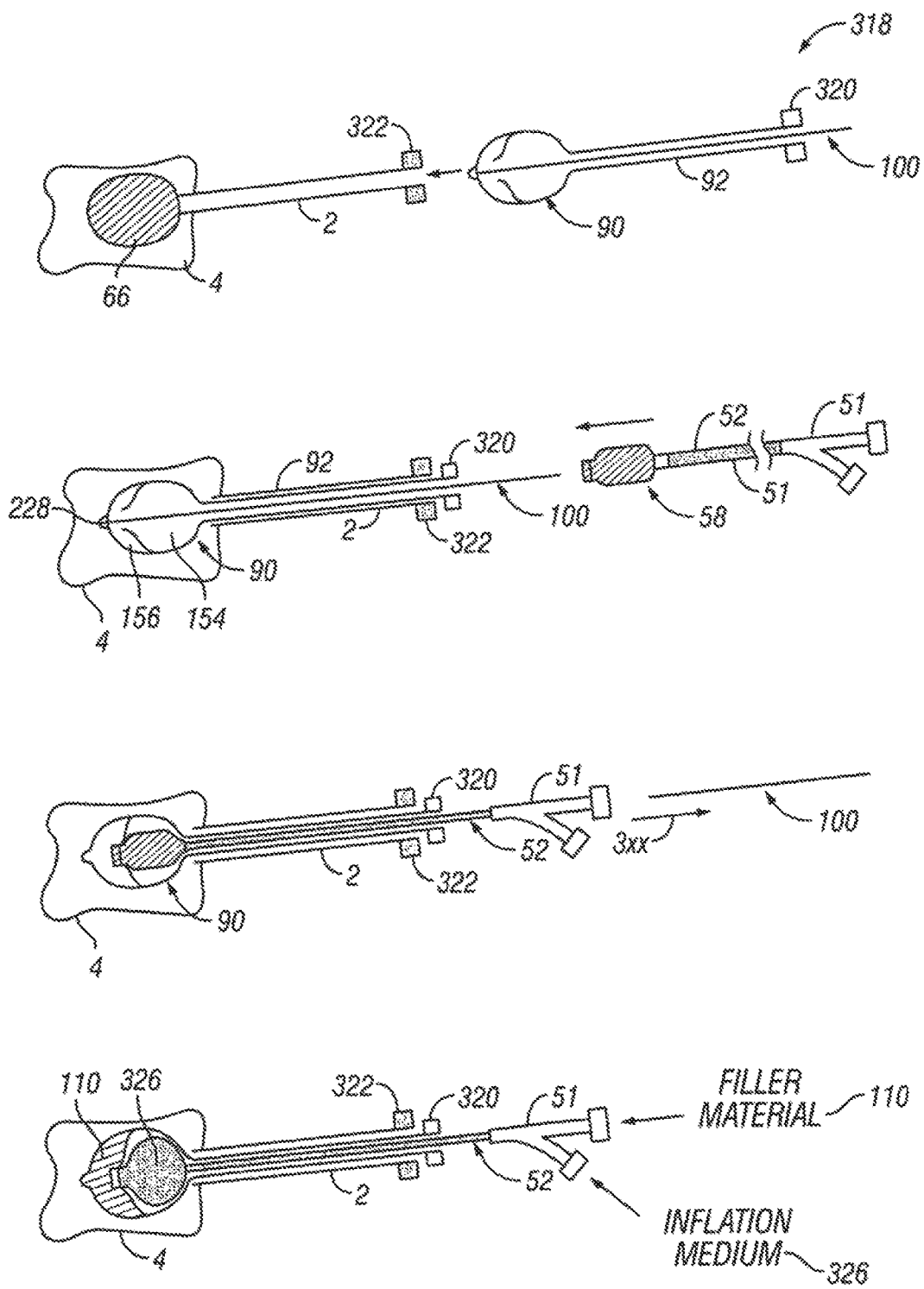
FIG. 103 illustrates actions (1)-(4) of a treatment implementation employing a double-chamber containment jacket in accordance with an embodiment of the present invention.

FIG. 103 illustrates some actions (1)-(4) of an exemplary treatment implementation 318. In action (1), a containment jacket 90 at the distal end of a tubular member 92 is placed into a cavity 66 of the vertebral bone 4. In this example, a guide wire 100 is used to place the containment jacket 90 through an access cannula 2 into the pre-created cavity 66. A containment assembly hub 320 docks on the cannula hub 322. Of course, the hubs 320 and 322 are depicted as simplified representations, and may include various configurations and fittings, and so forth.

In action (2), a balloon 58 (at the distal end of a catheter 51 having an inner lumen 52) or inflatable bone tamp is placed through the annular member 92 and slid over the guide wire 100 into the proximal region of the containment jacket 90. In one example, a stylet may be removed from the balloon 58 and catheter 51 or inflatable bone tamp prior to sliding the balloon 58 and catheter 51 over the guide wire 100. A catheter hub or fitting (not illustrated) may dock with the containment assembly hub 320.

In action (3), the guide wire 100 is removed. In action (4), filler material 110 (e.g., bone cement, polymethyl methacrylate, PMMA, etc.), is delivered via the catheter 51 through the inner lumen 52 into the distal region 156 (distal chamber) of the containment jacket 90. An exemplary amount of bone cement as the filler material 110 so injected is 1 cubic centimeter, for instance. Then, the balloon 58 disposed in the proximal region 156 (proximal chamber) is inflated with an inflation medium 326 while the filler material 110 (e.g., bone cement) cures in the distal region 154. The inflation medium may be injected, for example, through the annulus between the inside diameter of the outer wall of the catheter 51 and the outside diameter of the inner lumen 52 of the catheter 51. Subsequent actions not illustrated may include deflating and removing the balloon 58 and catheter 51, and filling the proximal region 154 with filler material 110 using the annular member 92 for access, and one of various filling devices discussed previously, for instance. An exemplary amount of filler material 110 put into the proximal region 154 may be 2-4 cubic centimeters according to the size of the cavity 66, for example.

Figure 104:
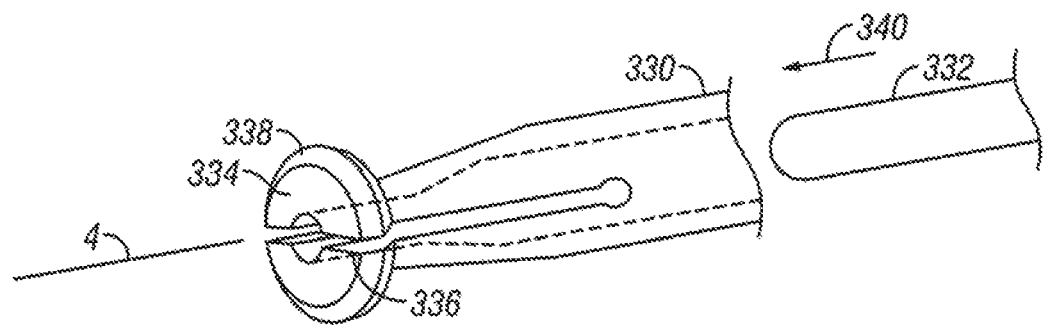
FIGS. 104-106 illustrate a cutting device 330 in accordance with an embodiment of the present invention.
Figure 105:
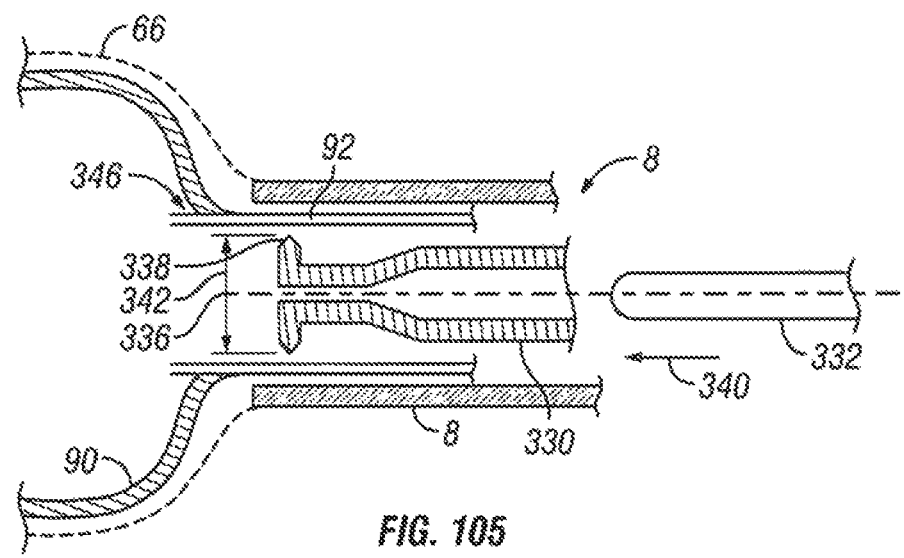
Figure 106:
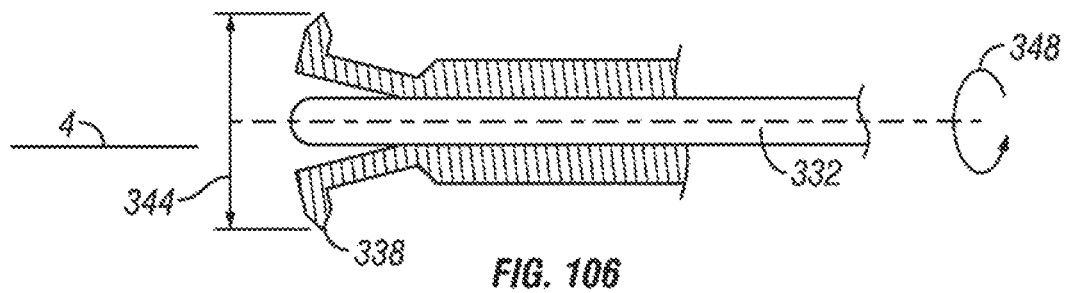

FIGS. 104-106 illustrate an exemplary cutting device 330 that might be employed as the cutting device 162 in FIG. 33 and in other implementations of a cutting device in treatment of a vertebral body 4. The cutting device 330 illustrated in FIGS. 104-106 may be used to cut the containment jacket 90 (at a neck region) from the annular member 92, so to leave the containment jacket 90 in place in the created cavity 66 of the vertebral bone 4.

FIG. 104 is a perspective view of the cutting device 330. The illustrated pusher rod 332 or other apparatus may be inserted into the cutting device 330 to push apart the face 334 (at the gap 336) and thus push apart halves of the cutting edge 338, in this example. In the illustrated embodiment, the insertion direction of the pusher rod 332 is indicated by arrow 340.

FIG. 105 illustrates the containment jacket 90 disposed in the created cavity 66 of the vertebral bone 4. In this example, the containment jacket 90 is coupled to the annular member 92 residing in the access cannula 8. FIG. 105 depicts the cutting device 330 inserted into the annular member 92 in the access cannula 8.

FIG. 106 illustrates the pusher rod 332 inserted into the interior of the cutting device 330, increasing the diameter of the cutting edge 338 from a first relaxed diameter 342 (FIG. 105) to a second expanded diameter 344 (FIG. 106). The cutting edge 338 at its second expanded diameter 344 engages the inner diameter or inner surface of the annular member 92. Such engagement cuts the annular member 92 to detach the containment jacket 90. Thus, the annular member 92 may be removed, leaving the containment jacket 90 in the cavity 66 of the vertebral body 4. Accordingly, the containment jacket 90 containing the filler material 110 may be left within the vertebral body 4. The cut may be made generally at a neck region 346, for example, where the containment jacket 90 meets the annular member 92. In this example, the pusher bar 332 or other inserted apparatus employed may be rotated so to turn the cutting device 330 and its expanded cutting edge 338 against the inner surface of the annular member 92.

Figure 107:
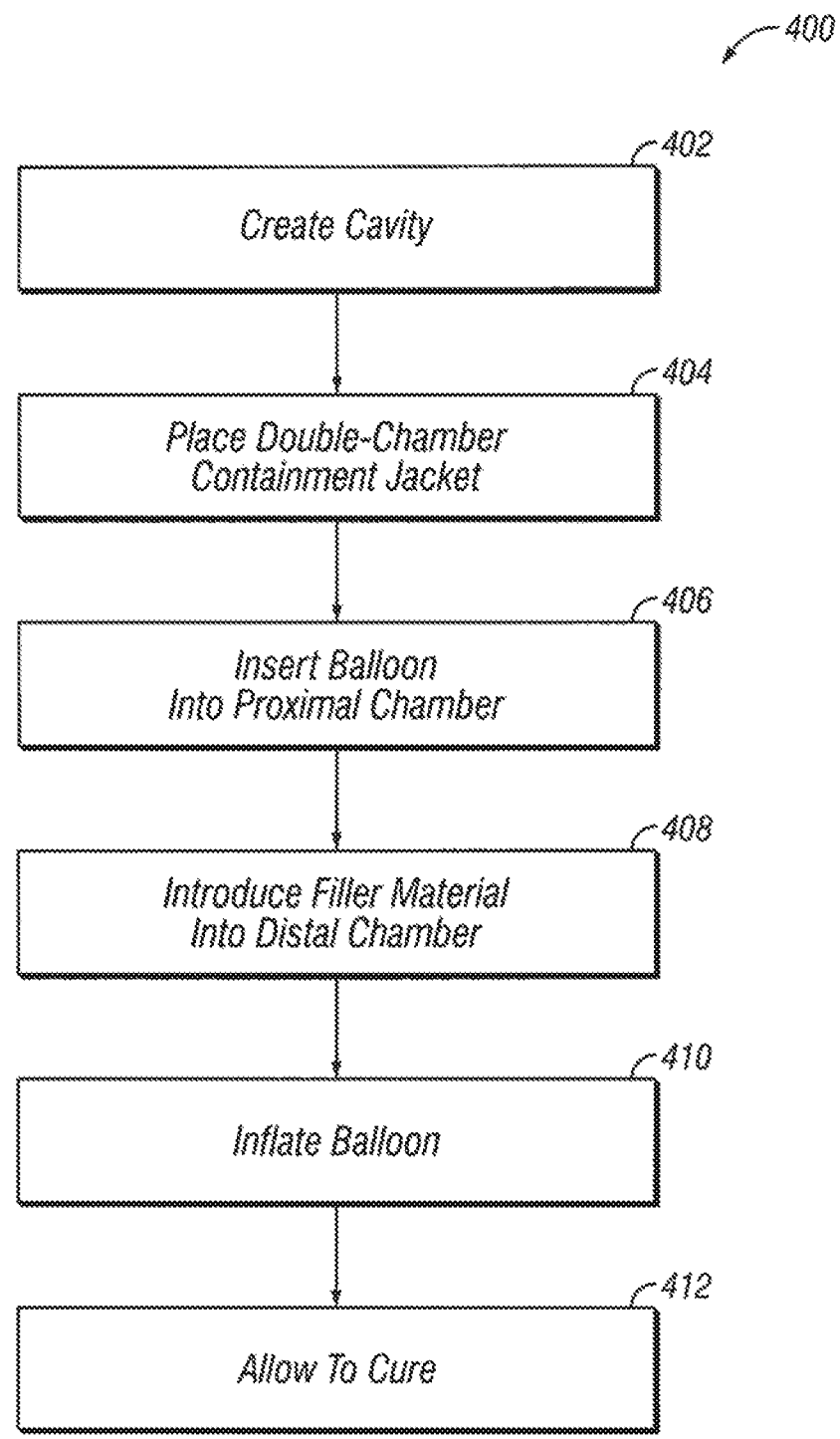
FIGS. 107-108 are a block flow diagram of a method of treating a bone with a double-chamber containment jacket in accordance with an embodiment of the present invention.

FIG. 107 is a method 400-1 for treating a bone, such as a vertebral body. Initially, a cavity is created (block 402) in the bone. As discussed, a cavity 66 may be created (block 402) in a vertebral body 4, for example, in a variety of ways. Moreover, an access cannula 2 may be employed. After cavity creation, a containment enclosure such as a double-chamber containment jacket 90 is placed (block 404) into the cavity 66. A guiding device or guide wire 100 may be used to place (block 404) the containment jacket 90 through the access cannula 2 into the cavity 66, for example. To so use the guide wire 100, the guide wire 100 may be inserted into a containment conduit or tubular member 92 coupled to the containment jacket 90, and the guide wire 100 docked in a nose or distal portion (docking tip) of the containment jacket 90.

A balloon 58 (e.g., of an inflatable bone tamp) is inserted (block 406) into the proximal region or proximal chamber of the containment jacket 90. For instance, an inner lumen 52 within the balloon 58 may be slid over the guide wire 100 in the tubular member 92 into the proximal chamber 154. The discharge portion of the inner lumen 52 (for injecting filler material isolated from the balloon 58, for example) may reside in the proximal region 154 at an opening 158 in the dividing wall 152 between the proximal chamber 154 and the distal chamber 156. In certain embodiments, the inner lumen 52 may extend through the opening 158.

Filler material such as bone cement is introduced (block 408) into the distal chamber 156, such as via the inflatable bone tamp and/or a catheter, for example. The guide wire 100 may be removed from the inner lumen 52 and containment assembly prior to introducing (block 408) the filler material 110 into the distal chamber 156. The balloon 58 residing in the proximal chamber 154 is inflated (block 410) via the inflatable bone tamp or catheter, for example, and the filler material 110 in the distal chamber 156 allowed (block 412) to cure.

Figure 108:
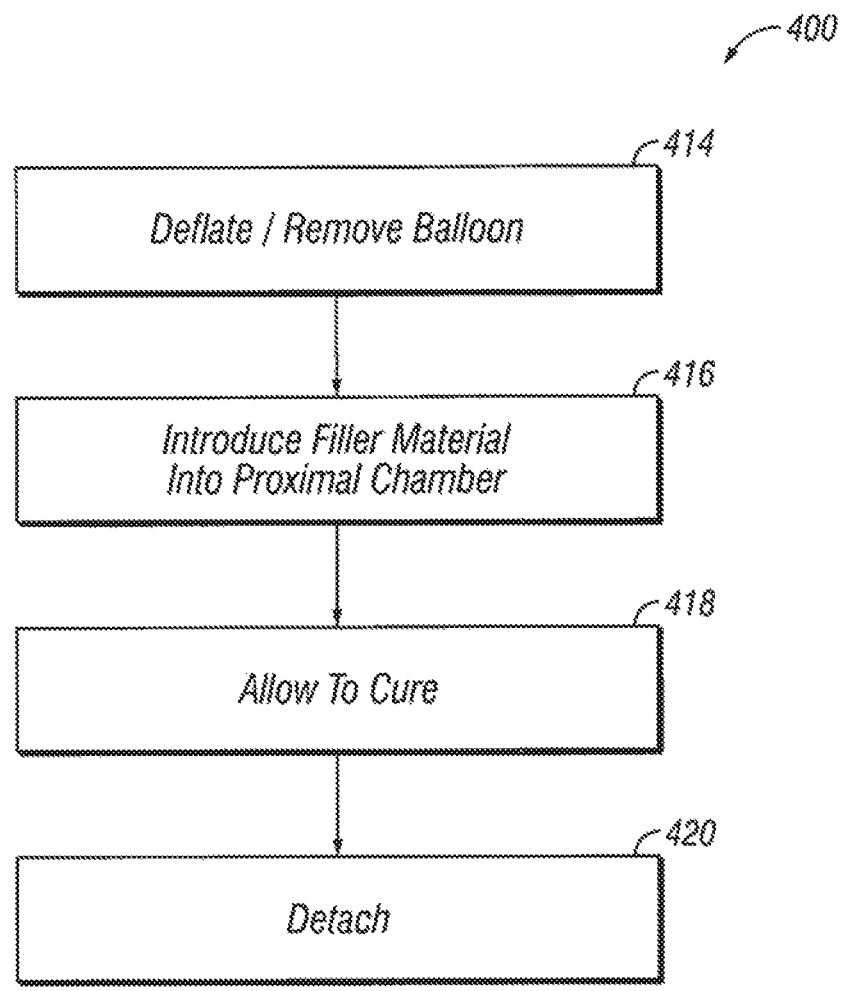

FIG. 108 is a method 400-2 that continues from the method 400-1 of FIG. 107. The balloon 58 is deflated and removed (block 414) from the proximal chamber 154 of the containment jacket 90. Additional filler material 110 is introduced into the proximal chamber 154, and the filler material 110 allowed to cure. Further, as discussed, the containment jacket 90 may be detached from the containment assembly (i.e., from the tubular member 92) and remain in the cavity 66 for treatment of the vertebral bone 4. To detach the containment jacket 90, a cutting device 162 or 330 may be inserted into the tubular member 92 to cut the neck region at the interface of the containment jacket 90 and the upstream containment conduit or tubular member 92.

Double-Chamber Containment Jacket—Example Implementation

In a particular example not meant to limit the present techniques but given as merely exemplary, a vertebral body 4 is treated via a surgical technique for height restoration. A CONTAIN™ assembly having a containment enclosure (e.g., containment jacket 90) having two chambers and coupled to an upstream containment conduit or tubular member 82 is employed. To treat the vertebral body 4 or bone, the containment jacket 90 is inserted through an access cannula 2 by pushing a pre-assembled guide wire 100 (e.g., a K-wire) until bottomed out inside the created cavity 66 in the vertebral body 4. Then, a bone tamp is slide over the guide wire 100 and inserted into the CONTAIN™ assembly until docked in the distal tip (e.g., nipple 228) of the containment jacket 90. Subsequently, while holding the bone tamp, the guide wire 100 is removed through the bone tamp. Further, the distal chamber 156 of the containment jacket 90 is de-aerated by attaching a Vaklock syringe to a stylet valve on the bone tamp and pulling a vacuum.

Next, 0.5 cubic centimeter (cc) of a filler material 110 (e.g., bone cement) is injected through the bone tamp and into the distal chamber 156 of the containment jacket 190. The bone tamp may be pulled proximal by about 2 millimeters (mm) prior to injection of the filler material 110 to ensure that the tip of the bone tamp is not pressed against the distal wall of the containment jacket 90 during injection of the filler material 110 (e.g., in the case where the inner tube or inner lumen of the bone tamp may extend into the distal chamber). After injection of the filler material 110, the filler material 110 is allowed to partially cure for about 2-3 minutes. Then, the bone tamp (i.e., a balloon 58 of the bone tamp in the proximal chamber 158) is inflated to about 3 cc, and the cement in the distal chamber 156 allowed to substantially or fully cure. The bone tamp is deflated and removed from the vertebral body 4 through the cannula 2. The proximal chamber 158 of the containment jacket 90 is then backfilled with filler material 110.

Double-Chamber Containment Jacket—Alternate Implementation

In an alternate implementation, a one-step fill may be employed with the CONTAIN™ assembly having the double-chamber containment jacket 90. The containment jacket 90 may be inserted through the cannula 2 via a guide wire 100 (e.g., K-Wire) into the created cavity 66 in the vertebral body 4. The alternate implementation may include the following actions. Insert a filler device over the guide wire 100 into the containment jacket 90, and then remove the guide wire 100. Fill the filler device with filler material 110 (e.g., bone cement) and insert fully such that the tip is docked into the distal chamber 156 of the containment jacket 90. Dispense filler material 110 (e.g., about 0.2 cc) into the distal chamber 156 of the containment jacket 90 by pressing a plunger through the filler device. Remove the filler device. Back fill the proximal chamber of the containment jacket 90 with the filler material 110 using the filler device connected to a cement gun or other filling instrument.

While it is apparent that the invention disclosed herein is well calculated to fulfill the objects stated above, it will be appreciated that numerous modifications and embodiments may be devised by those skilled in the art.

What is claimed is:

1. A method for treating bone, comprising:
creating a cavity in the bone;
placing a containment jacket into the cavity, the containment jacket coupled to an annular member;
introducing filler material into the containment jacket;
inserting a cutting device into the annular member, the cutting device including a cutting edge, wherein a pusher rod is configured to enter into the cutting device at a proximal end of the cutting device, the proximal end having a proximal diameter, and wherein the cutting edge is defined by halves and a gap disposed between the halves; and
moving the pusher rod from the proximal end to a distal end of the cutting device to increase a diameter of the gap from a first relaxed diameter to a second expanded diameter such that the cutting edge engages an inner surface of the annular member, thereby detaching the containment jacket from the annular member, wherein the second expanded diameter of the gap is greater than the proximal diameter.

2. The method of claim 1 further comprising rotating the pusher rod such that the cutting edge is rotated.

3. The method of claim 1, wherein the cutting edge extends around a face of the cutting device, the face being defined by the halves and the gap, and by moving the pusher rod distally into the cutting device, the pusher rod pushes apart the face at the gap, thereby pushing apart the halves of the cutting edge.

4. The method of claim 1 further comprising removing the annular member, thereby leaving the containment jacket in the cavity.

5. The method of claim 1 further comprising, before introducing filler material into the containment jacket, inflating at least a portion of the containment jacket with a balloon.

6. The method of claim 5, wherein inserting the balloon comprises sliding the balloon over a guide wire.

7. The method of claim 1, wherein placing the containment jacket comprises using a guide wire to place the containment jacket into the cavity.

8. The method of claim 7, wherein the containment jacket is coupled to a distal portion of a containment conduit, and wherein using the guide wire comprises situating the guide wire in the containment conduit.

9. The method of claim 8, wherein a distal part of the guide wire extends through the containment conduit and in a docking tip of the containment jacket.

10. The method of claim 1 further comprising inserting the annular member through an access cannula.

11. The method of claim 1, wherein the bone is a vertebral body, and wherein the cavity is created in the vertebral body through a pedicle.

12. A method for treating bone, comprising:
creating a cavity in the bone;
placing a containment jacket into the cavity, the containment jacket coupled to an annular member;
introducing filler material into the containment jacket;
inserting a cutting device into the annular member, the cutting device including a proximal end and a distal end, wherein the distal end comprises a cutting edge extending around a face of the cutting device, the face being separated into two halves by a gap; and
inserting a pusher rod distally into the cutting device to increase a diameter of the gap from a first relaxed diameter to a second expanded diameter such that the pusher rod pushes apart the face at the gap, thereby pushing apart the two halves of the cutting edge to engage an inner surface of the annular member, and detaching the containment jacket from the annular member, wherein the second expanded diameter of the gap is greater than a proximal diameter of the cutting device at the proximal end.

13. The method of claim 12 further comprising rotating the cutting edge.

14. The method of claim 12, wherein a guide wire is inserted into the annular member, and the guide wire is docked in a nose of the containment jacket.

15. The method of claim 12 further comprising, before introducing filler material into the containment jacket, inflating at least a portion of the containment jacket with a balloon.

16. The method of claim 12 further comprising removing the annular member, thereby leaving the containment jacket in the cavity.

17. The method of claim 12, wherein the bone is a vertebral body, and wherein the cavity is created in the vertebral body through a pedicle.

18. The method of claim 12, wherein the filler material is bone cement, and the bone cement is allowed to cure before inserting the cutting device into the annular member.

19. A method for treating bone, comprising:
creating a cavity in the bone;
placing a containment jacket into the cavity, the containment jacket coupled to an annular member;
inflating the containment jacket;
inserting a cutting device into the annular member, the cutting device including a proximal end and a distal end, wherein the distal end comprises a cutting edge extending around a face of the cutting device, the face being separated into two halves by a gap; and
inserting a pusher rod distally into the cutting device to increase a distance between the two halves such that the pusher rod pushes apart the face at the gap, thereby pushing apart the two halves of the cutting edge to engage an inner surface of the annular member, and detaching the containment jacket from the annular member, wherein the distance between the two halves is configured to extend to a distance greater than a proximal diameter at the proximal end.

20. The method of claim 19, wherein the bone is a vertebral body, and wherein the cavity is created in the vertebral body through a pedicle.

* * * * *